(12) United States Patent
Stadler et al.

(10) Patent No.: US 11,253,178 B2
(45) Date of Patent: Feb. 22, 2022

(54) NONINVASIVE ASSESSMENT OF CARDIAC RESYNCHRONIZATION THERAPY

(71) Applicant: Medtronic, Inc., Minneapolis, MN (US)

(72) Inventors: Robert W. Stadler, Shoreview, MN (US); Subham Ghosh, Blaine, MN (US)

(73) Assignee: Medtronic, Inc., Minneapolis, MN (US)

( * ) Notice: Subject to any disclaimer, the term of this patent is extended or adjusted under 35 U.S.C. 154(b) by 917 days.

(21) Appl. No.: 15/643,172

(22) Filed: Jul. 6, 2017

(65) Prior Publication Data

US 2017/0303840 A1    Oct. 26, 2017

Related U.S. Application Data

(63) Continuation-in-part of application No. 15/009,817, filed on Jan. 28, 2016, now abandoned.
(Continued)

(51) Int. Cl.
*A61B 5/02* (2006.01)
*A61B 5/15* (2006.01)
(Continued)

(52) U.S. Cl.
CPC .......... *A61B 5/150053* (2013.01); *A61B 5/02* (2013.01); *A61B 5/1107* (2013.01);
(Continued)

(58) Field of Classification Search
CPC .............. A61B 2505/05; A61B 5/0053; A61B 5/04085; A61B 5/04286; A61B 5/0472;
(Continued)

(56) References Cited

U.S. PATENT DOCUMENTS 4,233,987 A    11/1980    Feingold
4,402,323 A     9/1983    White
(Continued)

FOREIGN PATENT DOCUMENTS

CN    1043621 A    7/1990
CN    1253761 A    5/2000
(Continued)

OTHER PUBLICATIONS

Livneh et al., "Extracorporeal acute cardiac pacing by high intensity focused utlrasound", Progress in Biophysics and Molecular Biology, 115, 2014 (Year: 2014).*
(Continued)

*Primary Examiner* — Christopher L Cook
(74) *Attorney, Agent, or Firm* — Mueting Raasch Group

(57) ABSTRACT

Systems, methods, and interfaces are described herein for noninvasively determining an optimal coronary sinus branch to cannulate for a medical electrical lead. One exemplary method involves applying an electrode apparatus having a plurality of electrodes to a torso of a patient. One of a right ventricular (RV) lead is introduced to a right ventricle or a right atrial (RA) lead is introduced to a right atrium. Noninvasively ultrasonic energy is introduced to a target tissue selected from a set of target tissues. In response to delivering ultrasonic energy to the cardiac tissue, a processing unit receives a torso-surface potential signal from each of a plurality of electrodes distributed on a torso of a patient for the target tissue. Signals are sensed from one of the RA lead and the RV lead in response to delivering ultrasonic energy. For at least a subset of the plurality of electrodes, calculating, with the processing unit, a torso-surface activation time based on the signal sensed from the electrode. Determining whether the tissue site or the another tissue site provides optimal cardiac resynchronization.

12 Claims, 25 Drawing Sheets

Related U.S. Application Data

(60) Provisional application No. 62/359,053, filed on Jul. 6, 2016, provisional application No. 62/109,106, filed on Jan. 29, 2015.

(51) Int. Cl.

| | | |
|---|---|---|
| A61B 5/00 | (2006.01) | |
| A61N 1/362 | (2006.01) | |
| A61N 7/02 | (2006.01) | |
| A61B 5/11 | (2006.01) | |
| A61B 5/282 | (2021.01) | |
| A61B 5/366 | (2021.01) | |
| A61N 7/00 | (2006.01) | |
| A61B 5/30 | (2021.01) | |

(52) U.S. Cl.
CPC .............. *A61B 5/282* (2021.01); *A61B 5/366* (2021.01); *A61B 5/4848* (2013.01); *A61B 5/4884* (2013.01); *A61B 5/743* (2013.01); *A61N 1/362* (2013.01); *A61N 7/02* (2013.01); *A61B 5/0048* (2013.01); *A61B 5/0053* (2013.01); *A61B 5/150068* (2013.01); *A61B 5/303* (2021.01); *A61B 2505/05* (2013.01); *A61N 1/3627* (2013.01); *A61N 2007/0026* (2013.01)

(58) Field of Classification Search
CPC ..... A61B 5/1107; A61B 5/4848; A61B 5/743; A61B 5/0048; A61B 5/02; A61B 5/150053; A61B 5/150068; A61N 1/362; A61N 1/3627; A61N 2007/0026; A61N 7/02; A61N 2007/0004; A61N 2007/0056; A61N 7/00

See application file for complete search history.

(56) References Cited

U.S. PATENT DOCUMENTS

| | | |
|---|---|---|
| 4,428,378 A | 1/1984 | Anderson et al. |
| 4,497,326 A | 2/1985 | Curry |
| 4,566,456 A | 1/1986 | Koning et al. |
| 4,593,702 A | 6/1986 | Kepski |
| 4,674,511 A | 6/1987 | Cartmell |
| 4,763,660 A | 8/1988 | Kroll et al. |
| 4,777,955 A | 10/1988 | Brayten et al. |
| 4,787,389 A | 11/1988 | Tarjan |
| 4,979,507 A | 12/1990 | Heinz et al. |
| 5,052,388 A | 10/1991 | Sivula et al. |
| 5,054,496 A | 10/1991 | Wen et al. |
| 5,311,873 A | 5/1994 | Savard et al. |
| 5,331,960 A | 7/1994 | Lavine |
| 5,334,220 A | 8/1994 | Sholder |
| 5,443,492 A | 8/1995 | Stokes et al. |
| 5,485,849 A | 1/1996 | Panescu et al. |
| 5,514,163 A | 5/1996 | Markowitz et al. |
| 5,552,645 A | 9/1996 | Weng |
| 5,628,778 A | 5/1997 | Kruse et al. |
| 5,671,752 A | 9/1997 | Sinderby et al. |
| 5,683,429 A | 11/1997 | Mehra |
| 5,683,432 A | 11/1997 | Goedeke et al. |
| 5,687,737 A | 11/1997 | Branham et al. |
| 5,810,740 A | 9/1998 | Paisner |
| 5,876,336 A | 3/1999 | Swanson et al. |
| 5,891,045 A | 4/1999 | Albrecht et al. |
| 5,922,014 A | 7/1999 | Warman et al. |
| 6,055,448 A | 4/2000 | Anderson et al. |
| 6,128,535 A | 10/2000 | Maarse et al. |
| 6,141,588 A | 10/2000 | Cox et al. |
| 6,187,032 B1 | 2/2001 | Ohyu et al. |
| 6,205,357 B1 | 3/2001 | Ideker et al. |
| 6,226,542 B1 | 5/2001 | Reisfeld |
| 6,236,883 B1 | 5/2001 | Ciaccio et al. |
| 6,243,603 B1 | 6/2001 | Ideker et al. |
| 6,246,898 B1 | 6/2001 | Vesely et al. |
| 6,301,496 B1 | 10/2001 | Reisfeld |
| 6,311,089 B1 | 10/2001 | Mann et al. |
| 6,330,476 B1 | 12/2001 | Ben-Haim et al. |
| 6,358,214 B1 | 3/2002 | Tereschouk |
| 6,377,856 B1 | 4/2002 | Carson |
| 6,381,493 B1 | 4/2002 | Stadler et al. |
| 6,393,316 B1 | 5/2002 | Gillberg et al. |
| 6,418,346 B1 | 7/2002 | Nelson et al. |
| 6,439,236 B1 | 8/2002 | Porter et al. |
| 6,442,433 B1 | 8/2002 | Linberg |
| 6,456,867 B2 | 9/2002 | Reisfeld |
| 6,473,638 B2 | 10/2002 | Ferek-Petric |
| 6,480,745 B2 | 11/2002 | Nelson et al. |
| 6,484,118 B1 | 11/2002 | Govari |
| 6,507,756 B1 | 1/2003 | Heynen et al. |
| 6,532,379 B2 | 3/2003 | Stratbucker |
| 6,584,343 B1 | 6/2003 | Ransbury et al. |
| 6,599,250 B2 | 7/2003 | Webb et al. |
| 6,625,482 B1 | 9/2003 | Panescu et al. |
| 6,640,136 B1 | 10/2003 | Helland et al. |
| 6,650,927 B1 | 11/2003 | Keidar |
| 6,766,189 B2 | 7/2004 | Yu et al. |
| 6,772,004 B2 | 8/2004 | Rudy |
| 6,804,555 B2 | 10/2004 | Warkentin |
| 6,847,836 B1 | 1/2005 | Sujdak |
| 6,856,830 B2 | 2/2005 | He |
| 6,882,882 B2 | 4/2005 | Struble et al. |
| 6,885,889 B2 | 4/2005 | Chinchoy |
| 6,915,149 B2 | 7/2005 | Ben-Haim |
| 6,968,237 B2 | 11/2005 | Doan et al. |
| 6,975,900 B2 | 12/2005 | Rudy et al. |
| 6,978,184 B1 | 12/2005 | Marcus et al. |
| 6,980,675 B2 | 12/2005 | Evron et al. |
| 7,016,719 B2 | 3/2006 | Rudy et al. |
| 7,031,777 B2 | 4/2006 | Hine et al. |
| 7,058,443 B2 | 6/2006 | Struble |
| 7,062,315 B2 | 6/2006 | Koyrakh et al. |
| 7,092,759 B2 | 8/2006 | Nehls et al. |
| 7,142,922 B2 | 11/2006 | Spinelli et al. |
| 7,184,835 B2 | 2/2007 | Kramer et al. |
| 7,215,998 B2 | 5/2007 | Wesselink et al. |
| 7,286,866 B2 | 10/2007 | Okerlund et al. |
| 7,308,297 B2 | 12/2007 | Reddy et al. |
| 7,308,299 B2 | 12/2007 | Burrell et al. |
| 7,313,444 B2 | 12/2007 | Pianca et al. |
| 7,321,677 B2 | 1/2008 | Evron et al. |
| 7,346,381 B2 | 3/2008 | Okerlund et al. |
| 7,398,116 B2 | 7/2008 | Edwards |
| 7,426,412 B1 | 9/2008 | Schecter |
| 7,454,248 B2 | 11/2008 | Burrell et al. |
| 7,499,743 B2 | 3/2009 | Vass et al. |
| 7,509,170 B2 | 3/2009 | Zhang et al. |
| 7,565,190 B2 | 7/2009 | Okerlund et al. |
| 7,587,074 B2 | 9/2009 | Zarkh et al. |
| 7,599,730 B2 | 10/2009 | Hunter et al. |
| 7,610,088 B2 | 10/2009 | Chinchoy |
| 7,613,500 B2 | 11/2009 | Vass et al. |
| 7,616,993 B2 | 11/2009 | Müssig et al. |
| 7,664,550 B2 | 2/2010 | Eick et al. |
| 7,684,863 B2 | 3/2010 | Parikh et al. |
| 7,742,629 B2 | 6/2010 | Zarkh et al. |
| 7,747,047 B2 | 6/2010 | Okerlund et al. |
| 7,751,882 B1 | 7/2010 | Helland et al. |
| 7,769,451 B2 | 8/2010 | Yang et al. |
| 7,778,685 B2 | 8/2010 | Evron et al. |
| 7,778,686 B2 | 8/2010 | Vass et al. |
| 7,787,951 B1 | 8/2010 | Min |
| 7,813,785 B2 | 10/2010 | Okerlund et al. |
| 7,818,040 B2 | 10/2010 | Spear et al. |
| 7,848,807 B2 | 12/2010 | Wang |
| 7,860,580 B2 | 12/2010 | Falk et al. |
| 7,894,889 B2 | 2/2011 | Zhang |
| 7,912,544 B1 | 3/2011 | Min et al. |
| 7,917,214 B1 | 3/2011 | Gill et al. |
| 7,941,213 B2 | 5/2011 | Markowitz et al. |
| 7,953,475 B2 | 5/2011 | Harlev et al. |
| 7,953,482 B2 | 5/2011 | Hess |

(56) References Cited

U.S. PATENT DOCUMENTS

| | | |
|---|---|---|
| 7,983,743 B2 | 7/2011 | Rudy et al. |
| 7,996,063 B2 | 8/2011 | Vass et al. |
| 7,996,070 B2 | 8/2011 | van Dam et al. |
| 8,010,194 B2 | 8/2011 | Muller |
| 8,019,402 B1 | 9/2011 | Kryzpow et al. |
| 8,019,409 B2 | 9/2011 | Rosenberg et al. |
| 8,032,229 B2 | 10/2011 | Gerber et al. |
| 8,036,743 B2 | 10/2011 | Savage et al. |
| 8,060,185 B2 | 11/2011 | Hunter et al. |
| 8,150,513 B2 | 4/2012 | Chinchoy |
| 8,160,700 B1 | 4/2012 | Ryu et al. |
| 8,175,703 B2 | 5/2012 | Dong et al. |
| 8,180,428 B2 | 5/2012 | Kaiser et al. |
| 8,195,292 B2 | 6/2012 | Rosenberg et al. |
| 8,213,693 B1 | 7/2012 | Li |
| 8,214,041 B2 | 7/2012 | Van Gelder et al. |
| 8,265,738 B1 | 9/2012 | Min et al. |
| 8,285,377 B2 | 10/2012 | Rosenberg et al. |
| 8,295,943 B2 | 10/2012 | Eggen et al. |
| 8,326,419 B2 | 12/2012 | Rosenberg et al. |
| 8,332,030 B2 | 12/2012 | Hess et al. |
| 8,380,308 B2 | 2/2013 | Rosenberg et al. |
| 8,401,616 B2 | 3/2013 | Verard et al. |
| 8,478,388 B2 | 7/2013 | Nguyen et al. |
| 8,509,896 B2 | 8/2013 | Doerr et al. |
| 8,527,051 B1 | 9/2013 | Hedberg et al. |
| 8,583,230 B2 | 11/2013 | Ryu et al. |
| 8,615,298 B2 | 12/2013 | Ghosh et al. |
| 8,617,082 B2 | 12/2013 | Zhang et al. |
| 8,620,433 B2 | 12/2013 | Ghosh et al. |
| 8,639,333 B2 | 1/2014 | Stadler et al. |
| 8,694,099 B2 | 4/2014 | Ghosh et al. |
| 8,738,132 B1 | 5/2014 | Ghosh et al. |
| 8,744,576 B2 | 6/2014 | Munsterman et al. |
| 8,768,465 B2 | 7/2014 | Ghosh et al. |
| 8,805,504 B2 | 8/2014 | Sweeney |
| 8,972,228 B2 | 3/2015 | Ghosh et al. |
| 9,037,238 B2 | 5/2015 | Stadler et al. |
| 9,155,897 B2 | 10/2015 | Ghosh et al. |
| 9,199,087 B2 | 12/2015 | Stadler et al. |
| 9,265,951 B2 | 2/2016 | Sweeney |
| 9,265,954 B2 | 2/2016 | Ghosh |
| 9,265,955 B2 | 2/2016 | Ghosh |
| 9,278,219 B2 | 3/2016 | Ghosh |
| 9,278,220 B2 | 3/2016 | Ghosh |
| 9,282,907 B2 | 3/2016 | Ghosh |
| 9,320,446 B2 | 4/2016 | Gillberg et al. |
| 2002/0072682 A1 | 6/2002 | Hopman et al. |
| 2002/0087089 A1 | 7/2002 | Ben-Haim |
| 2002/0143264 A1 | 10/2002 | Ding et al. |
| 2002/0161307 A1 | 10/2002 | Yu et al. |
| 2002/0169484 A1 | 11/2002 | Mathis et al. |
| 2003/0018277 A1 | 1/2003 | He |
| 2003/0050670 A1 | 3/2003 | Spinelli et al. |
| 2003/0105495 A1 | 6/2003 | Yu et al. |
| 2003/0236466 A1 | 12/2003 | Tarjan et al. |
| 2004/0015081 A1 | 1/2004 | Kramer et al. |
| 2004/0059237 A1 | 3/2004 | Narayan et al. |
| 2004/0097806 A1 | 5/2004 | Hunter et al. |
| 2004/0102812 A1 | 5/2004 | Yonce et al. |
| 2004/0122479 A1 | 6/2004 | Spinelli et al. |
| 2004/0162496 A1 | 8/2004 | Yu et al. |
| 2004/0172078 A1 | 9/2004 | Chinchoy |
| 2004/0172079 A1 | 9/2004 | Chinchoy |
| 2004/0193223 A1 | 9/2004 | Kramer et al. |
| 2004/0215245 A1 | 10/2004 | Stahmann et al. |
| 2004/0215252 A1 | 10/2004 | Verbeek et al. |
| 2004/0220635 A1 | 11/2004 | Burnes |
| 2004/0267321 A1 | 12/2004 | Boileau et al. |
| 2005/0008210 A1 | 1/2005 | Evron et al. |
| 2005/0027320 A1 | 2/2005 | Nehls et al. |
| 2005/0090870 A1 | 4/2005 | Hine et al. |
| 2005/0096522 A1 | 5/2005 | Reddy et al. |
| 2005/0107839 A1 | 5/2005 | Sanders |
| 2005/0149138 A1 | 7/2005 | Min et al. |
| 2006/0074285 A1 | 4/2006 | Zarkh et al. |
| 2006/0136004 A1 | 6/2006 | Cowan et al. |
| 2006/0224198 A1 | 10/2006 | Dong et al. |
| 2006/0235478 A1 | 10/2006 | Van Gelder et al. |
| 2006/0253162 A1 | 11/2006 | Zhang et al. |
| 2007/0142871 A1 | 6/2007 | Libbus et al. |
| 2007/0232943 A1 | 10/2007 | Harel et al. |
| 2007/0250129 A1 | 10/2007 | Van Oort |
| 2007/0265508 A1 | 11/2007 | Sheikhzadeh-Nadjar et al. |
| 2008/0021336 A1 | 1/2008 | Dobak et al. |
| 2008/0058656 A1 | 3/2008 | Costello et al. |
| 2008/0119903 A1 | 5/2008 | Arcot-Krishnamurthy et al. |
| 2008/0140143 A1 | 6/2008 | Ettori et al. |
| 2008/0146954 A1 | 6/2008 | Bojovic et al. |
| 2008/0242976 A1 | 10/2008 | Robertson et al. |
| 2008/0269818 A1 | 10/2008 | Sullivan et al. |
| 2008/0269823 A1 | 10/2008 | Burnes et al. |
| 2008/0281195 A1 | 11/2008 | Heimdal |
| 2008/0306567 A1 | 12/2008 | Park et al. |
| 2008/0306568 A1 | 12/2008 | Ding et al. |
| 2009/0005832 A1 | 1/2009 | Zhu et al. |
| 2009/0036947 A1 | 2/2009 | Westlund et al. |
| 2009/0043352 A1 | 2/2009 | Brooke et al. |
| 2009/0048528 A1 | 2/2009 | Hopenfeld et al. |
| 2009/0053102 A2 | 2/2009 | Rudy et al. |
| 2009/0054941 A1 | 2/2009 | Eggen et al. |
| 2009/0054946 A1 | 2/2009 | Sommer et al. |
| 2009/0084382 A1 | 4/2009 | Jalde et al. |
| 2009/0093857 A1 | 4/2009 | Markowitz et al. |
| 2009/0099468 A1 | 4/2009 | Thiagalingam et al. |
| 2009/0099469 A1 | 4/2009 | Flores |
| 2009/0099619 A1 | 4/2009 | Lessmeier et al. |
| 2009/0112109 A1 | 4/2009 | Kuklik et al. |
| 2009/0143838 A1 | 6/2009 | Libbus et al. |
| 2009/0157134 A1 | 6/2009 | Ziglio et al. |
| 2009/0157136 A1 | 6/2009 | Yang et al. |
| 2009/0198298 A1 | 8/2009 | Kaiser et al. |
| 2009/0216112 A1 | 8/2009 | Assis et al. |
| 2009/0232448 A1 | 9/2009 | Barmash et al. |
| 2009/0234414 A1 | 9/2009 | Sambelashvili et al. |
| 2009/0254140 A1 | 10/2009 | Rosenberg et al. |
| 2009/0270729 A1 | 10/2009 | Corbucci et al. |
| 2009/0270937 A1 | 10/2009 | Yonce et al. |
| 2009/0299201 A1 | 12/2009 | Gunderson |
| 2009/0299423 A1 | 12/2009 | Min |
| 2009/0306732 A1 | 12/2009 | Rosenberg et al. |
| 2009/0318995 A1 | 12/2009 | Keel et al. |
| 2010/0022873 A1 | 1/2010 | Hunter et al. |
| 2010/0049063 A1 | 2/2010 | Dobak, III |
| 2010/0069987 A1 | 3/2010 | Min et al. |
| 2010/0087888 A1 | 4/2010 | Maskara |
| 2010/0094149 A1 | 4/2010 | Kohut et al. |
| 2010/0113954 A1 | 5/2010 | Zhou |
| 2010/0114229 A1 | 5/2010 | Chinchoy |
| 2010/0121403 A1 | 5/2010 | Schecter et al. |
| 2010/0145405 A1 | 6/2010 | Min |
| 2010/0174137 A1 | 7/2010 | Shim |
| 2010/0198292 A1 | 8/2010 | Honeck et al. |
| 2010/0228138 A1 | 9/2010 | Chen |
| 2010/0234916 A1 | 9/2010 | Turcott et al. |
| 2010/0249622 A1 | 9/2010 | Olson |
| 2010/0254583 A1 | 10/2010 | Chan et al. |
| 2010/0268059 A1 | 10/2010 | Ryu et al. |
| 2011/0004111 A1 | 1/2011 | Gill et al. |
| 2011/0004264 A1 | 1/2011 | Siejko et al. |
| 2011/0022112 A1 | 1/2011 | Min |
| 2011/0054286 A1 | 3/2011 | Crosby |
| 2011/0054559 A1 | 3/2011 | Rosenberg et al. |
| 2011/0054560 A1 | 3/2011 | Rosenberg et al. |
| 2011/0075896 A1 | 3/2011 | Matsumoto |
| 2011/0092809 A1 | 4/2011 | Nguyen et al. |
| 2011/0112398 A1 | 5/2011 | Zarkh et al. |
| 2011/0118803 A1 | 5/2011 | Hou et al. |
| 2011/0137369 A1 | 6/2011 | Ryu et al. |
| 2011/0144510 A1 | 6/2011 | Ryu et al. |
| 2011/0172728 A1 | 7/2011 | Wang |
| 2011/0190615 A1 | 8/2011 | Phillips et al. |
| 2011/0201915 A1 | 8/2011 | Gogin et al. |
| 2011/0213260 A1 | 9/2011 | Keel et al. |

(56) References Cited

U.S. PATENT DOCUMENTS

| | | |
|---|---|---|
| 2011/0319954 A1 | 12/2011 | Niazi et al. |
| 2012/0004567 A1 | 1/2012 | Eberle et al. |
| 2012/0101543 A1 | 4/2012 | Demmer et al. |
| 2012/0101546 A1 | 4/2012 | Stadler et al. |
| 2012/0203090 A1 | 8/2012 | Min |
| 2012/0253419 A1 | 10/2012 | Rosenberg et al. |
| 2012/0283587 A1 | 11/2012 | Ghosh et al. |
| 2012/0284003 A1 | 11/2012 | Ghosh et al. |
| 2012/0296387 A1 | 11/2012 | Zhang et al. |
| 2012/0296388 A1 | 11/2012 | Zhang et al. |
| 2012/0302904 A1 | 11/2012 | Lian et al. |
| 2012/0303084 A1 | 11/2012 | Kleckner et al. |
| 2012/0310297 A1 | 12/2012 | Sweeney |
| 2012/0330179 A1 | 12/2012 | Yuk et al. |
| 2013/0006332 A1 | 1/2013 | Sommer et al. |
| 2013/0018250 A1 | 1/2013 | Caprio et al. |
| 2013/0018251 A1 | 1/2013 | Caprio et al. |
| 2013/0030491 A1 | 1/2013 | Stadler et al. |
| 2013/0060298 A1 | 3/2013 | Splett et al. |
| 2013/0072790 A1 | 3/2013 | Ludwig et al. |
| 2013/0096446 A1 | 4/2013 | Michael et al. |
| 2013/0116739 A1 | 5/2013 | Brada et al. |
| 2013/0131529 A1 | 5/2013 | Jia et al. |
| 2013/0131749 A1 | 5/2013 | Sheldon et al. |
| 2013/0131751 A1 | 5/2013 | Stadler et al. |
| 2013/0136035 A1 | 5/2013 | Bange et al. |
| 2013/0150913 A1 | 6/2013 | Bornzin et al. |
| 2013/0165983 A1 | 6/2013 | Ghosh et al. |
| 2013/0165988 A1 | 6/2013 | Ghosh |
| 2013/0184697 A1* | 7/2013 | Han .................. A61B 18/18 606/33 |
| 2013/0261471 A1 | 10/2013 | Saha et al. |
| 2013/0261688 A1 | 10/2013 | Dong et al. |
| 2013/0289640 A1 | 10/2013 | Zhang et al. |
| 2013/0296726 A1 | 11/2013 | Niebauer et al. |
| 2013/0304407 A1 | 11/2013 | George et al. |
| 2013/0324828 A1 | 12/2013 | Nishiwaki et al. |
| 2014/0005563 A1 | 1/2014 | Ramanathan et al. |
| 2014/0018872 A1 | 1/2014 | Siejko et al. |
| 2014/0135866 A1* | 5/2014 | Ramanathan ....... G06F 19/3481 607/18 |
| 2014/0135867 A1 | 5/2014 | Demmer et al. |
| 2014/0163633 A1 | 6/2014 | Ghosh et al. |
| 2014/0222099 A1 | 8/2014 | Sweeney |
| 2014/0236252 A1 | 8/2014 | Ghosh et al. |
| 2014/0276125 A1 | 9/2014 | Hou et al. |
| 2014/0277233 A1 | 9/2014 | Ghosh |
| 2014/0323882 A1 | 10/2014 | Ghosh et al. |
| 2014/0323892 A1 | 10/2014 | Ghosh et al. |
| 2014/0323893 A1 | 10/2014 | Ghosh et al. |
| 2014/0371807 A1 | 12/2014 | Ghosh et al. |
| 2014/0371808 A1 | 12/2014 | Ghosh et al. |
| 2014/0371832 A1 | 12/2014 | Ghosh et al. |
| 2014/0371833 A1 | 12/2014 | Ghosh et al. |
| 2015/0032016 A1 | 1/2015 | Ghosh |
| 2015/0032171 A1 | 1/2015 | Ghosh |
| 2015/0032172 A1 | 1/2015 | Ghosh |
| 2015/0032173 A1 | 1/2015 | Ghosh |
| 2015/0045849 A1 | 2/2015 | Ghosh et al. |
| 2015/0142069 A1 | 5/2015 | Sambelashvili |
| 2015/0157225 A1 | 6/2015 | Gillberg et al. |
| 2015/0157231 A1 | 6/2015 | Gillberg et al. |
| 2015/0157232 A1 | 6/2015 | Gillberg et al. |
| 2015/0157865 A1 | 6/2015 | Gillberg et al. |
| 2015/0216434 A1 | 8/2015 | Ghosh et al. |
| 2015/0265840 A1 | 9/2015 | Ghosh et al. |
| 2016/0030747 A1 | 2/2016 | Thakur et al. |
| 2016/0030751 A1 | 2/2016 | Ghosh et al. |
| 2016/0045737 A1 | 2/2016 | Ghosh et al. |
| 2016/0045738 A1 | 2/2016 | Ghosh et al. |
| 2016/0045744 A1 | 2/2016 | Gillberg et al. |
| 2016/0184590 A1 | 6/2016 | Gosh |

FOREIGN PATENT DOCUMENTS

| | | |
|---|---|---|
| CN | 1878595 A | 12/2006 |
| CN | 101073502 A | 11/2007 |
| CN | 103202727 A | 7/2013 |
| EP | 1 072 284 A2 | 1/2001 |
| EP | 1 504 713 A1 | 2/2005 |
| EP | 2 016 976 A1 | 1/2009 |
| EP | 2 391 270 A1 | 7/2011 |
| EP | 1 925 337 B1 | 3/2012 |
| EP | 2 436 309 A2 | 4/2012 |
| EP | 2 435 132 B1 | 8/2013 |
| WO | WO 1998/026712 A1 | 6/1998 |
| WO | WO 1999/006112 A1 | 2/1999 |
| WO | WO 2000/045700 A1 | 8/2000 |
| WO | WO 2001/067950 A1 | 9/2001 |
| WO | WO 2003/070323 A1 | 8/2003 |
| WO | WO 2005/056108 A2 | 6/2005 |
| WO | WO 2006/069215 A2 | 6/2006 |
| WO | WO 2006/105474 A2 | 10/2006 |
| WO | WO 2006/115777 A1 | 11/2006 |
| WO | WO 2006/117773 A1 | 11/2006 |
| WO | WO 2007/013994 A2 | 2/2007 |
| WO | WO 2007/027940 A2 | 3/2007 |
| WO | WO 2007/013994 A3 | 4/2007 |
| WO | WO 2007/027940 A3 | 6/2007 |
| WO | WO 2007/139456 A1 | 12/2007 |
| WO | WO 2008/151077 A2 | 12/2008 |
| WO | WO 2006/069215 A3 | 6/2009 |
| WO | WO 2009/079344 A1 | 6/2009 |
| WO | WO 2009/139911 A2 | 11/2009 |
| WO | WO 2009/148429 A1 | 12/2009 |
| WO | WO 2010/019494 A1 | 2/2010 |
| WO | WO 2010/071520 A1 | 6/2010 |
| WO | WO 2010/088040 A1 | 8/2010 |
| WO | WO 2010/088485 A1 | 8/2010 |
| WO | WO 2011/070166 A1 | 6/2011 |
| WO | WO 2011/090622 A1 | 7/2011 |
| WO | WO 2011/099992 A1 | 8/2011 |
| WO | WO 2012/037471 A2 | 3/2012 |
| WO | WO 2012/037471 A3 | 6/2012 |
| WO | WO 2012/106297 A2 | 8/2012 |
| WO | WO 2012/106297 A3 | 8/2012 |
| WO | WO 2012/109618 A2 | 8/2012 |
| WO | WO 2012/110940 A1 | 8/2012 |
| WO | WO 2012/109618 A3 | 11/2012 |
| WO | WO 2012/151364 A1 | 11/2012 |
| WO | WO 2012/151389 A1 | 11/2012 |
| WO | WO 2013/006724 A2 | 1/2013 |
| WO | WO 2013/010165 A1 | 1/2013 |
| WO | WO 2013/010184 A1 | 1/2013 |
| WO | WO 2013/006724 A3 | 4/2013 |
| WO | WO 2014/179454 A1 | 11/2014 |
| WO | WO 2014/179459 A2 | 11/2014 |
| WO | WO 2014/179459 A3 | 1/2015 |
| WO | WO 2015/013271 A1 | 1/2015 |
| WO | WO 2015/013493 A1 | 1/2015 |
| WO | WO 2015/013574 A1 | 1/2015 |

OTHER PUBLICATIONS

Anatomy and PHysiology: Chapter 19. "The cardiovascular system: The heart", accessed online at https://opentextbc.ca/anatomyandphysiology/chapter/19-3-cardiac-cycle/ (Year: 2013).*

(PCT/US2016/015738) PCT Notification of Transmittal of the International Search Report and the Written Opinion of the International Searching Authority, dated Apr. 22, 2016, 15 pages.

Biffi et al., "Occurrence of Phrenic Nerve Stimulation in Cardiac Resynchronization Therapy Patients: the Role of Left Ventricular Lead Type and Placement Site," *Europace*, 2013; 15:77-82.

Botker MD, PhD., et al., "Electromechanical Mapping for Detection of Myocardial Viability in Patients with ischemia Cardiomyopathy," Circulation, Mar. 2001; vol. 103, No. 12, pp. 1631-1637.

"CardioGuide System Enables Real-Time Navigation of Left Ventricular Leads During Medtronic CRT Implants," Press Release, Apr. 9, 2013, Medtronic, Inc., 2 pgs.

(56) References Cited

OTHER PUBLICATIONS

Cuculich, P.S., et al., "The Electrophysiological Cardiac Ventricular Substrate in Patients After Myocardial Infection" *J. Am. Coll. Cardiol.* 2011; 58:1893-1902.
Czerwinska et al., "Method of Segmentation of Thorax Organs Images Applied to Modeling the Cardiac Electrical Field," *Engineering in Medicine and Biology Society*, Proceedings of the 22nd Annual International Conference of the IEEE, vol. 1, 23, Jul. 23, 2000,; pp. 402-405.
Dawoud, F. et al., "Inverse Electrocardiographic Imaging to Assess Electrical Dyssynchrony in Cardiac Resynchronization Therapy Patients," *Computing in Cardiology*, 2012; 3 9:993-996.
Fung et al., Chapter 20, Optimization of Cardiac Resynchronization Therapy, Cardiac Resynchronization Therapy, Second Edition, Copyright 2008, Blackwell Publishing Ltd., pp. 356-373.
Ghosh et al. "Accuracy of Quadratic Versus Linear Interpolation in Noninvasive Electrocardiographic Imaging (ECGI)," *Annuals of Biomedical Engineering*, vol. 33, No. 9. Sep. 2005; pp. 1187-1201.
Ghosh et al. "Application of L1-Norm Regularization to Epicardial Potential Solution of the Inverse Electrocardiography Problem," *Annuals of Biomedical Engineering*, vol. 37, No. 5, May 2009; pp. 902-912.
Ghosh et al., "Cardiac Memory in Patents with Wolff-Parkinson-White Syndrome: Noninvasive Imaging of Activation and Repolarization Before and After Catheter Ablation" *Circulation*, 2008; 118:907-915. Published online Aug. 12, 2008.
Ghosh et al., "Electrophysiological Substrate and Intraventricular LV Dyssynchrony in Non-ischemic Heart Failure Patients Undergoing Cardiac Resynchronization Therapy," *Heart rhythm : the official journal of the Heart Rhythm Society*, 2011; 8(5):692-699.
Gold et al., "Comparison of Stimulation Sites within Left Ventricular Veins on the Acute Hemodynamic Effects of Cardiac Resynchronization Therapy" *Heart Rhythm*, Apr. 2005; 2(4):376-381.
Gulrajani, "The Forward and Inverse Problems of Electrocardiography," *IEEE Engineering in Medicine and Biology*, IEEE Service Center, vol. 17, No. 5, Sep. 1, 1988; pp. 84-101, 122.
Hansen, "Regularization Tools: A Matlab Package for Analysis and Solution of Discrete Ill-Posed Problems," Version 4.1 for Matlab 7.3; Mar. 2008; 128 pages. Retrieved from the Internet: Jun. 19, 2014 http://www.mathworks.com/matlabcentral/fileexchange/52-regtools.
Hayes et al., "Cardiac Resynchronization Therapy and the Relationship of Percent Biventricular Pacing to Symptoms and Survival," *Heart Rhythm*, Sep. 2011; 8(9):1469-1475.
"Heart Failure Management" datasheet [online], Medtronic, Minneapolis, Minnesota, [Last updated on Jun. 3, 2013].Retrieved from the Internet: www.medtronic.com; 9 pages.
Hopenfeld et al., "The Effect of Conductivity on ST—Segment Epicardial Potentials Arising from Subendocardial Ischemia," Annals of Biomedical Eng., Jun. 2005; vol. 33, No. 6, pp. 751-763.
Jia et al., "Electrocardiographic Imaging of Cardiac Resynchronization Therapy in Heart Failure: Observation of Variable Electrophysiologic Responses," *Heart Rhythm*, vol. 3, No. 3; Mar. 1, 2006, pp. 296-310.
Kornreich, "Body Surface Potential Mapping of ST Segment Changes in Acute Myocardial Infarction," *Circulation*, 1993; 87: 773-782.
Medtronic Vitatron Carelink Encore® Programmer Model 29901 Reference Manual, 2013, Medtronic, Inc., Minneapolis, MN.
Lumason™, Brochure, Bracco Diagnostocs. Oct. 2014.
Miri et al., "Applicability of body surface potential map in computerized optimization of biventricular pacing," *Annals of Biomedical Engineering*, vol. 38, No. 3, Mar. 2010, pp. 865-875.
Miri et al., "Comparison of the electrophysiologically based optimization methods with different pacing parameters in patient undergoing resynchronization treatment," *30th Annual International IEEE EMBS Conference*, Aug. 2008, pp. 1741-1744.
Miri et al., "Computerized Optimization of Biventricular Pacing Using Body Surface Potential Map," *31st Annual International Conference of the IEEE EMBS*, Sep. 2009, pp. 2815-2818.
Miri et al., "Efficiency of Timing Delays and Electrode Positions in Optimization of Biventricular Pacing: A Simulation Study," *IEEE Transactions on Biomedical Engineering*, Nov. 2009, pp. 2573-2582.
Modre et al., "Noninvasive Myocardial Activation Time Imaging: A Novel Inverse Algorithm Applied to Clinical ECG Mapping Data" *IEEE Transactions on Biomedical Engineering*, vol. 49; No. 10, Oct. 2002; pp. 1153-1161.
Nash et al., "An Experimental-Computational Framework for Validating in-vivo ECG Inverse Algorithms," International Journal of Bioelectromagnetism, vol. 2, No. 2, Dec. 31, 2000, 9 pp.
Potse et al., "Mathematical Modeling and Simulation of Ventricular Activation Sequences: Implications for Cardiac Resynchronization Therapy," *J. of Cardiovasc. Trans. Res.*, 2012; 5:146-158.
Prinzen et al., "Cardiac Resynchronization Therapy State-of-the-Art of Current Applications, Guidelines, Ongoing Trials, and Areas of Controversy" Circulation, 2013; 128: 2407-2418.
Ryu et al., "Simultaneous Electrical and Mechanical Mapping Using 3D Cardiac Mapping System: Novel Approach for Optimal Cardiac Resynchronization Therapy," *Journal of Cardiovascular Electrophysiology*, Feb. 2010; 21(2):219-22.
Silva et al., "Cardiac Resynchronization Therapy in Pediatric Congenital Heart Disease: Insights from Noninvasive Electrocardiographic Imaging" *Heart Rhythm*, vol. 6, No. 8. Aug. 1, 2009; pp. 1178-1185.
Singh et al., "Left Ventricular Lead Position and Clinical Outcome in the Multicenter Automatic Defibrillator Implantation Trial-Cardiac Resynchronization Therapy (MADIT-CRT) Trial," *Circulation*, 2011; 123:1159-1166.
Sperzel et al., "Intraoperative Characterization of Interventricular Mechanical Dyssynchrony Using Electroanatomic Mapping System—A Feasibility Study," *Journal of Interventional Cardiac Electrophysiology*, Nov. 2012; 35(2):189-96.
Steinhaus BM., "Estimating cardiac transmembrane activation and recovery times from unipolar and bipolar extracellular electrograms : a simulation study," *Circulation Research*, 1989, 64:449-462.
Strik et al., "Electrical and Mechanical Ventricular Activation During Left Bundle Branch Block and Resynchronization," *J. of Cardiovasc. Trans. Res.*, 2012; 5:117-126.
Svendsen et al., "Computational Models of Cardiac Electrical Activation," Chapter 5, Computational Nov. 2010, pp. 73-88.
Sweeney et al., "Analysis of Ventricular Activation Using Surface Electrocardiography to Predict Left Ventricular Reverse Volumetric Remodeling During Cardiac Resynchronization Therapy," *Circulation*, Feb. 9, 2010; 121(5):626-634.
Sweeney et al., QRS Fusion Complex Analysis Using Wave Interference to Predict Reverse Remodeling During Cardiac Resynchronization Therapy, heart Rhythm, 2014, 11:806-813.
Turner et al, "Electrical and Mechanical Components of Dyssynchrony in Heart Failure Patients with Normal QRS Duration and Left Bundle-Branch Block," *Circulation* 2004; 109: 2544-2549.
Van Deursen et al., "Vectorcardiography as a Tool for Wasy Optimization of Cardiac Resynchronization Therapy in Canine LBBB Hearts," *Circulation Arrhythmia and Electrophysiology*, Jun. 1, 2012; 5(3):544-52. Available online Apr. 24, 2012.
Vardas et al., The Task Force for Cardiac Pacing and Cardiac Resynchronization Therapy of the European Society of Cardiology. Developed in Collaboration with the European Heart Rhythm Association, *European Heart Journal*, 2007; 28:2256-2295.
Varma et al., "Placebo CRT," *Journal of Cardiovascular Electrophysiology*, vol. 19, Aug. 2008; p. 878.
Wang et al., "Application of the Method of Fundamental Solutions to Potential-based Inverse Electrocardiography," *Annals of Biomedical Engineering*, Aug. 2006, pp. 1272-1288.
Wellens, MD et al., "The Electrocardiogram 102 Years After Einthoven," Circulation, Feb. 2004; vol. 109, No. 5, pp. 562-564.
Williams et al., "Short-Term Hemodynamic Effects of Cardiac Resynchronization Therapy in Patients With Heart Failure, a Narrow QRS Duration, and No Dyssynchrony," *Circulation*, Oct. 27, 2009; 120: 1687-1694.
Livneh et al., "Extracorporeal Acute Cardiac Pacing by High Intensity Focused Ultrasound", Progress in Biophysics and Molecular Biology, 115, 2014.

(56) References Cited

OTHER PUBLICATIONS

Anatomy and Physiology: Chapter 19: "The Cardiovascular System: The Heart", accessed online at https://opentextbc.ca/anatomyandphysiology/chapter/19-3-cardiac-cycle/, 2013.

* cited by examiner

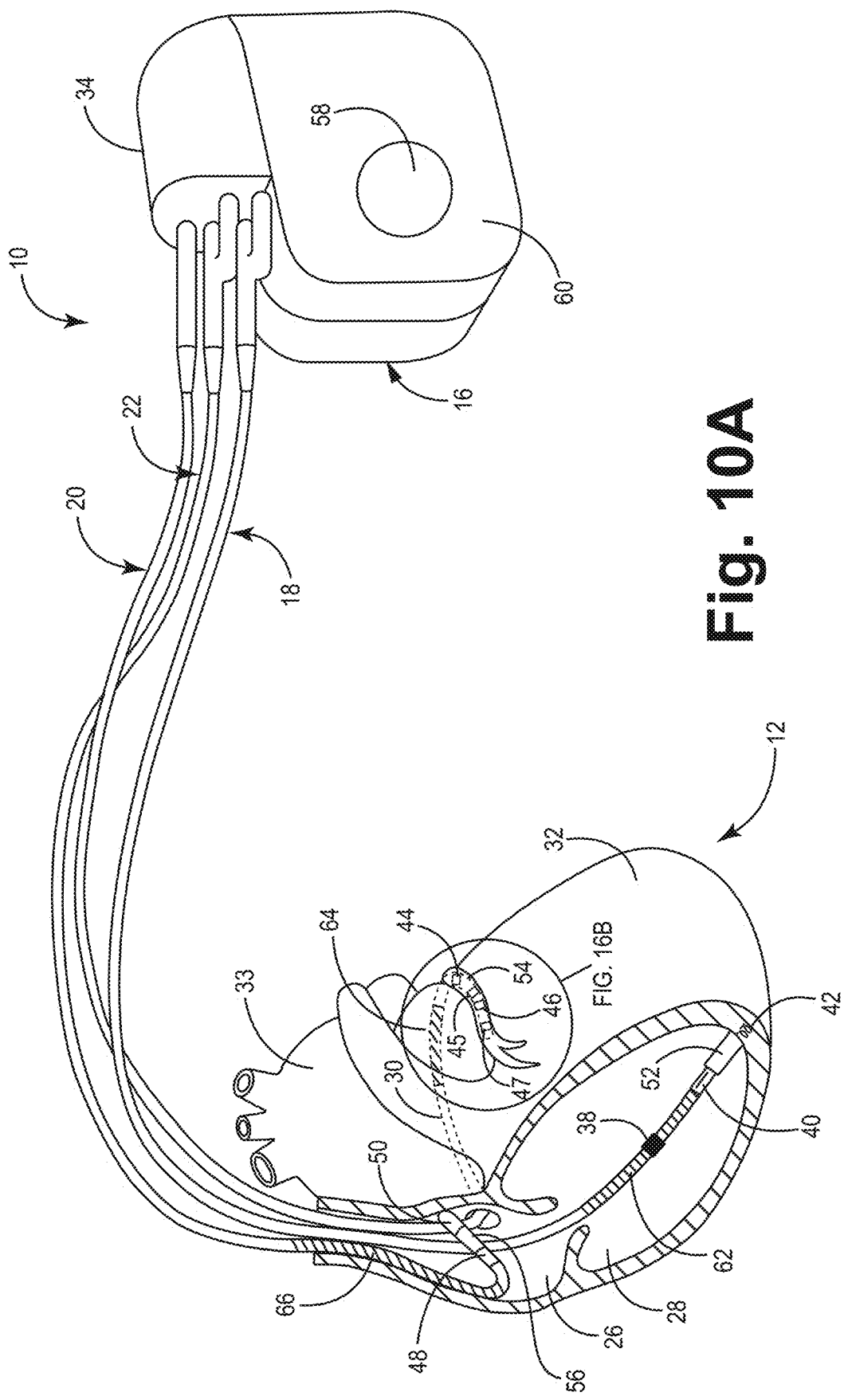

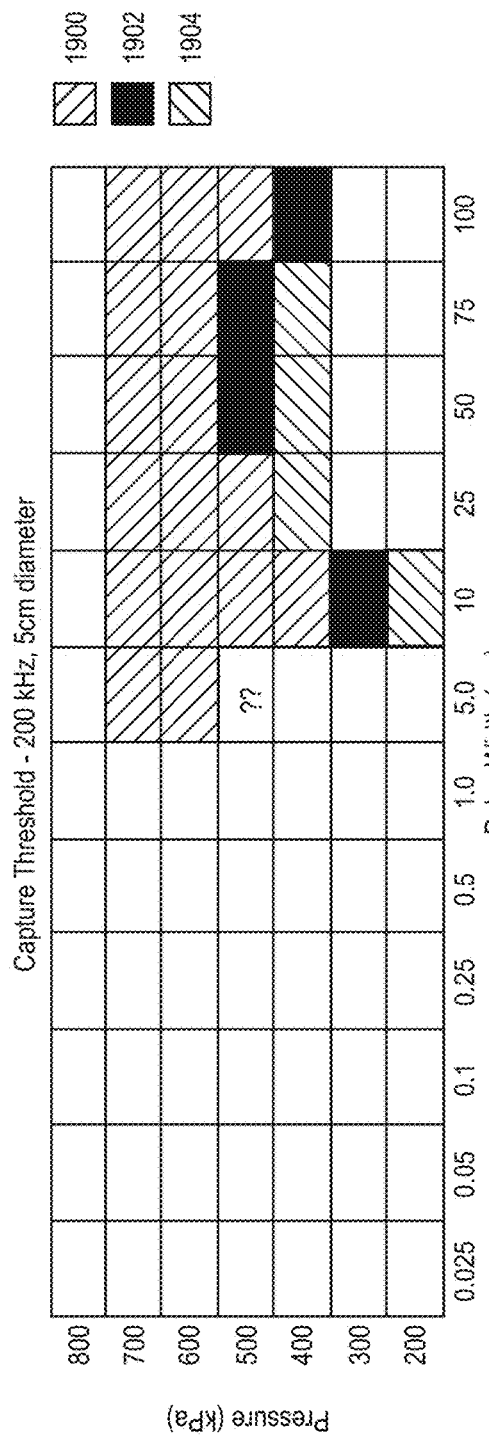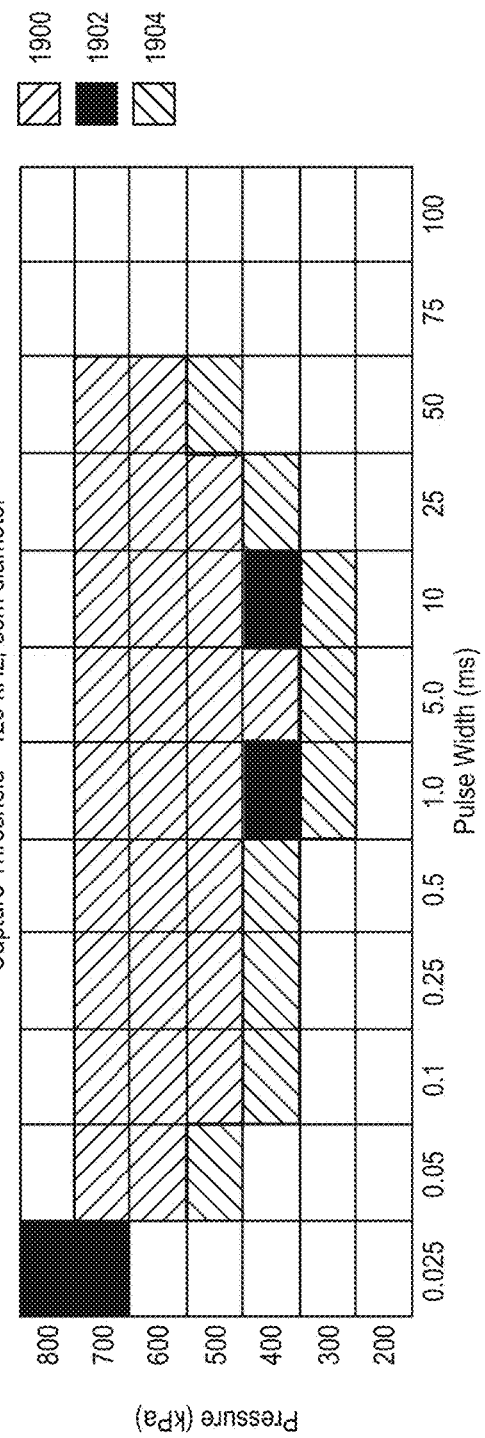

NONINVASIVE ASSESSMENT OF CARDIAC RESYNCHRONIZATION THERAPY

RELATED APPLICATION

This application is a continuation in part of U.S. patent application Ser. No. 15/009,817, filed Jan. 28, 2016 with the same title, which also claims the benefit of U.S. Provisional Application No. 62/109,106, filed on Jan. 29, 2015, both of which are herein incorporated by reference in their entirety. This application further claims the benefit U.S. Provisional Application No. 62/359,053 filed Jul. 6, 2016, which is also incorporated by reference in its entirety.

TECHNICAL FIELD

The present disclosure relates to electrophysiology and, more particularly, to evaluating the electrical activation patterns of the heart.

BACKGROUND

The beat of the heart is controlled by the sinoatrial node, a group of conductive cells located in the right atrium near the entrance of the superior vena cava. The depolarization signal generated by the sinoatrial node activates the atrioventricular node. The atrioventricular node briefly delays the propagation of the depolarization signal, allowing the atria to drain, before passing the depolarization signal to the ventricles of the heart. The coordinated contraction of both ventricles drives the flow of blood through the torso of a patient. In certain circumstances, the conduction of the depolarization signal from the atrioventricular node to the left and right ventricles may be interrupted or slowed. This may result in a dyssynchrony in the contraction of the left and right ventricles, and eventually in heart failure or death.

Cardiac Resynchronization Therapy (CRT) may correct the symptoms of electrical dyssynchrony by providing pacing therapy to one or both ventricles or atria, e.g., by providing pacing to encourage earlier activation of the left or right ventricles. By pacing the contraction of the ventricles, the ventricles may be controlled so that the ventricles contract in synchrony. Patients undergoing CRT have experienced improved ejection fraction, increased exercise capacity, and an improved feeling of well-being. Even though patients can benefit from CRT, some patients are reluctant to incur the expense of implanting an ICD unless a substantial certainty exists that CRT will improve his or her health. It is therefore desirable to develop noninvasive methods or systems to determine whether CRT is beneficial for a patient before undergoing the expense of implanting a medical device.

SUMMARY

In general, the disclosure is directed towards techniques for noninvasively determining whether a patient could benefit from cardiac resynchronization therapy (CRT). The method can comprise non-invasive and/or invasive techniques for determining the best location from which to pace. The best location from which to pace may relate to LV endocardial pacing location, epicardial pacing location or coronary sinus (CS) branch to cannulate when placing a medical electrical lead. Selection of the optimal CS branch can occur prior to and/or during the process of implanting the lead. Generally, the method involves determining the optimal CS branch by sensing the cardiac response to non-invasive pacing pulses delivered by the ultrasound transducer through skin to a target cardiac tissue location. The cardiac response is sensed via the electrode apparatus (e.g. ECG belt etc.) and/or implanted electrodes (e.g. electrodes on a RV lead, subcutaneous electrodes etc.). The maps acquired during the noninvasive response are then matched to maps acquired during actual placement of the lead by the physician. For example, the map, acquired during the noninvasive measurements (i.e. ECG belt only) that provided the most optimal response to the ultrasound pacing pulses from an optimal location is used as a template to match with the maps acquired during real-time placement of the medical electrical lead. Once the previously stored and real-time map(s) are substantially matched, the optimal position of the pacing electrode(s) are properly positioned. Substantially matched maps (or map data) means that 10% or less difference exists between the stored and real-time acquired activation time maps). The physician then attaches the medical electrical lead or other pacing device in its location.

One or more other embodiments relate to adjusting timing of noninvasively pacing cardiac tissue to determine optimal cardiac resynchronization. The electrode apparatus is placed on or around all or a portion of the torso of the patient before delivering pacing pulses to tissue. In particular, the electrodes of electrode apparatus (e.g. ECG belt) may be positioned around a portion or the circumference of a patient, including the posterior, lateral, posterior lateral, and anterior locations of the torso of patient. Signals are acquired from the electrode apparatus (i.e. same signal acquired from the surface ECG (e.g. ECG belt for processing)) thereby allowing the processor to obtain periodic automatic detection of the intrinsic PR interval. Automatic sensing occurs of the p-wave from the ECG signal i.e. same signal that is sent to the ECG belt for processing). The timing of the ultrasound pacing can be adjusted in response sensing of the P-wave. For example, the timing of the ultrasound pacing could be adjusted in the following manner. First, detect a p-wave, then time the ultrasound pace to be PR minus a pre-specified time period (e.g. PR-50 ms, PR-40 ms, PR-30 ms, PR-20 ms etc.) following the P-wave, on successive beats. By timing the ultrasound pacing according to different PR minus a pre-specified time period, the timing of the ultrasound pacing can be evaluated through various degrees of fusion with intrinsic activation. In one or more embodiments, the ultrasonic delivery of pacing pulses can be combined with a 2-D ultrasound imaging phased array. An image can then be collected. The ultrasound transducer could be pointed in the direction for pacing delivery, and then pacing is fired in the desired direction. The image guidance would help to pace in good locations. Additionally or alternatively, the CRT pacing parameter(s) implemented by the implantable medical device can be set or adjusted in response to the P-wave acquired during the process of determining an optimal location of the pacing electrode used to pace cardiac tissue. For example, the timing to deliver pacing pulses may be adjusted using PR intervals, as described herein.

The details of one or more aspects of the disclosure are set forth in the accompanying drawings and the description below. Other features, objects, and advantages will be apparent from the description and drawings, and from the claims.

BRIEF DESCRIPTION OF THE DRAWINGS

FIG. 10A is a diagram of the exemplary IMD of FIG. 15.

FIG. 17A depicts a strength-duration curve, showing cardiac capture occurring at various ultrasound amplitudes and pulse widths in response to ultrasound stimuli being delivered by a transducer probe having a diameter of 5 cm and a frequency of 200 kHz.

FIG. 17B depicts a strength-duration curve, showing cardiac capture occurring at various ultrasound amplitudes and pulse widths in response to stimuli being delivered by an ultrasound transducer probe having a diameter of 3 cm and a frequency of 420 kHz.

DETAILED DESCRIPTION OF EXEMPLARY EMBODIMENTS

Figure 1:
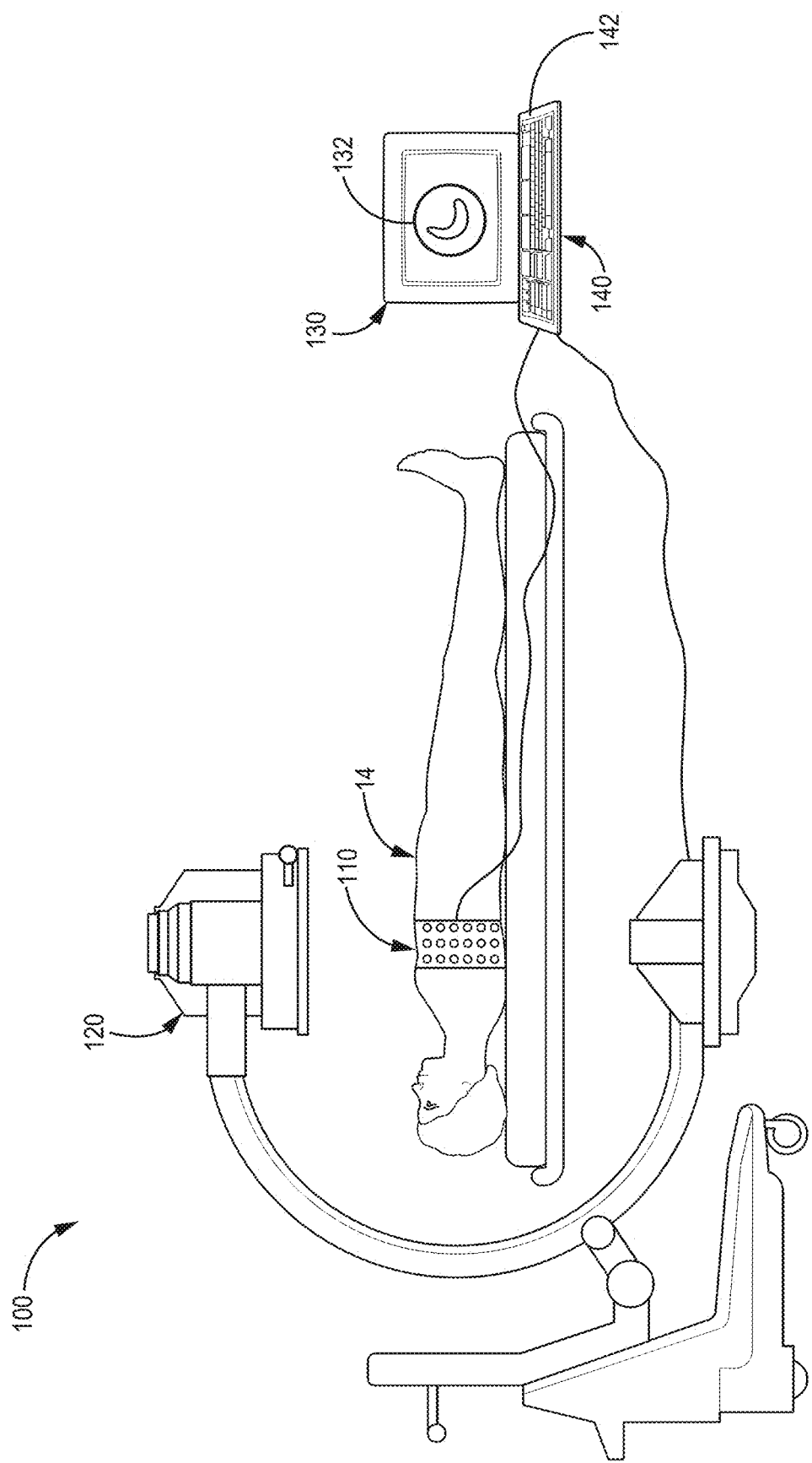
FIG. 1 is a diagram of an exemplary system including electrode apparatus, imaging apparatus, display apparatus, and computing apparatus.

In the following detailed description of illustrative embodiments, reference is made to the accompanying figures of the drawing which form a part hereof, and in which are shown, by way of illustration, specific embodiments which may be practiced. It is to be understood that other embodiments may be utilized and structural changes may be made without departing from (e.g., still falling within) the scope of the disclosure presented hereby.

The effectiveness of the therapy (e.g. CRT) can be performed without implanting a medical device in a patient. Accordingly, the present disclosure can provide some assurance to certain patients that they are indeed candidates for CRT. Additionally, the present disclosure may be useful in eliminating patients that may not find CRT to be helpful. Since the present disclosure is able to determine the effectiveness of CRT without implanting a device, cost savings will be achieved by the responsible party who pays for the services and devices such as patients, hospitals, insurance companies, and governments.

Exemplary systems, apparatus, and methods shall be described with reference to FIGS. 1-21. It will be apparent to one skilled in the art that elements or processes from one embodiment may be used in combination with elements or processes of the other embodiments, and that the possible embodiments of such methods, apparatus, and systems using combinations of features set forth herein is not limited to the specific embodiments shown in the Figures and/or described herein. Further, it will be recognized that the embodiments described herein may include many elements that are not necessarily shown to scale. Still further, it will be recognized that timing of the processes and the size and shape of various elements herein may be modified but still fall within the scope of the present disclosure, although certain timings, one or more shapes and/or sizes, or types of elements, may be advantageous over others.

From unipolar electrocardiogram (ECG) recordings, electrical activation times can be detected or estimated in proximity of a reference location (e.g., which can be a chosen location for the left ventricle lead during implant).

Such electrical activation times may be measured and displayed, or conveyed, to an implanter by a system which acquires the ECG signals and generates the metric of electrical activation (e.g., q-LV) time. Examples of ECG template acquisition and ECG signal analysis methods are generally disclosed in U.S. Pat. No. 6,393,316 to Gillberg, et al., U.S. Pat. No. 7,062,315 to Koyrakh, et al., and U.S. Pat. No. 7,996,070 to van Dam et al., incorporated herein by reference in their entireties.

As described herein, at least in one or more embodiments, electromechanical mapping to select a lead placement site for cardiac resynchronization therapy may use an algorithm that uses q-LV data (e.g., electrical activation times) in conjunction with mechanical motion map timings to best select a site for a LV lead.

As described herein, various exemplary systems, methods, and interfaces may be configured to use electrode apparatus including external electrodes, imaging apparatus, display apparatus, and computing apparatus to noninvasively assist a user (e.g., a physician) in selecting one or more locations (e.g., implantation site regions) proximate a patient's heart for one or more implantable electrodes and/or to navigate one or more implantable electrodes to the selected location(s). An exemplary system 100 including electrode apparatus 110, imaging apparatus 120, display apparatus 130, and computing apparatus 140 is depicted in FIG. 1.

The electrode apparatus 110 as shown includes a plurality of electrodes incorporated, or included within a band wrapped around the chest, or torso, of a patient 14. The electrode apparatus 110 is operatively coupled to the computing apparatus 140 (e.g., through one or wired electrical connections, wirelessly, etc.) to provide electrical signals from each of the electrodes to the computing apparatus 140 for analysis. Exemplary electrode apparatus 110 will be described in more detail in reference to FIGS. 3A-3B.

The imaging apparatus 120 may be any type of imaging apparatus configured to image, or provide images of, at least a portion of the patient in a non-invasive manner. For example, the imaging apparatus 120 may not use any components or parts that may be located within the patient to provide images of at least a portion of the patient except non-invasive tools such as contrast solution. It is to be understood that the exemplary systems, methods, and interfaces described herein may noninvasively assist a user (e.g., a physician) in determining whether therapy such as CRT can be effective for a particular patient. Additionally, the system is helpful in selecting a location proximate a patient's heart for an implantable electrode, and after the exemplary systems, methods, and interfaces have provided noninvasive assistance, the exemplary systems, methods, and interfaces may then provide assistance to implant, or navigate, an implantable electrode into the patient, e.g., proximate the patient's heart.

For example, after the exemplary systems, methods, and interfaces have provided noninvasive assistance, the exemplary systems, methods, and interfaces may then provide image guided navigation that may be used to navigate leads including electrodes, leadless electrodes, wireless electrodes, catheters, etc., within the patient's body. Further, although the exemplary systems, methods, and interfaces are described herein with reference to a patient's heart, it is to be understood that the exemplary systems, methods, and interfaces may be applicable to any other portion of the patient's body.

The imaging apparatus 120 may be configured to capture, or take, x-ray images (e.g., two dimensional x-ray images, three dimensional x-ray images, etc.) of the patient 14. The imaging apparatus 120 may be operatively coupled (e.g., through one or wired electrical connections, wirelessly, etc.) to the computing apparatus 140 such that the images captured by the imaging apparatus 120 may be transmitted to the computing apparatus 140. Further, the computing apparatus 140 may be configured to control the imaging apparatus 120 to, e.g., configure the imaging apparatus 120 to capture images, change one or more settings of the imaging apparatus 120, etc.

It will be recognized that while the imaging apparatus 120 as shown in FIG. 1 may be configured to capture x-ray images, any other alternative imaging modality may also be used by the exemplary systems, methods, and interfaces described herein. For example, the imaging apparatus 120 may be configured to capture images, or image data, using isocentric fluoroscopy, bi-plane fluoroscopy, ultrasound, computed tomography (CT), multi-slice computed tomography (MSCT), magnetic resonance imaging (MRI), high frequency ultrasound (HIFU), optical coherence tomography (OCT), intra-vascular ultrasound (IVUS), two dimensional (2D) ultrasound, three dimensional (3D) ultrasound, four dimensional (4D) ultrasound, intraoperative CT, intraoperative MRI, etc. Further, it is to be understood that the imaging apparatus 120 may be configured to capture a plurality of consecutive images (e.g., continuously) to provide video frame data. In other words, a plurality of images taken over time using the imaging apparatus 120 may provide motion picture data. Additionally, the images may also be obtained and displayed in two, three, or four dimensions. In more advanced forms, four-dimensional surface rendering of the heart or other regions of the body may also be achieved by incorporating heart data or other soft tissue data from an atlas map or from pre-operative image data captured by MRI, CT, or echocardiography modalities. Image datasets from hybrid modalities, such as positron emission tomography (PET) combined with CT, or single photon emission computer tomography (SPECT) combined with CT, could also provide functional image data superimposed onto anatomical data to be used to confidently reach target locations within the heart or other areas of interest.

The display apparatus 130 and the computing apparatus 140 may be configured to display and analyze data such as, e.g., surrogate electrical activation data, image data, mechanical motion data, etc. gathered, or collected, using the electrode apparatus 110 and the imaging apparatus 120 to noninvasively assist a user in location selection of an implantable electrode. In at least one embodiment, the computing apparatus 140 may be a server, a personal computer, or a tablet computer. The computing apparatus 140 may be configured to receive input from input apparatus 142 and transmit output to the display apparatus 130. Further, the computing apparatus 140 may include data storage that may allow for access to processing programs or routines and/or one or more other types of data, e.g., for driving a graphical user interface configured to noninvasively assist a user in location selection of an implantable electrode, etc.

The computing apparatus 140 may be operatively coupled to the input apparatus 142 and the display apparatus 130 to, e.g., transmit data to and from each of the input apparatus 142 and the display apparatus 130. For example, the computing apparatus 140 may be electrically coupled to each of the input apparatus 142 and the display apparatus 130 using, e.g., analog electrical connections, digital electrical connections, wireless connections, bus-based connections, network-based connections, internet-based connections, etc. As described further herein, a user may provide input to the input apparatus 142 to manipulate, or modify, one or more graphical depictions displayed on the display apparatus 130 to view and/or select one or more target or candidate locations of a portion of a patient's heart as further described herein.

Although as depicted the input apparatus 142 is a keyboard, it is to be understood that the input apparatus 142 may include any apparatus capable of providing input to the computing apparatus 140 to perform the functionality, methods, and/or logic described herein. For example, the input apparatus 142 may include a mouse, a trackball, a touchscreen (e.g., capacitive touchscreen, a resistive touchscreen, a multi-touch touchscreen, etc.), etc. Likewise, the display apparatus 130 may include any apparatus capable of displaying information to a user, such as a graphical user interface 132 including graphical depictions of anatomy of a patient's heart, images of a patient's heart, graphical depictions of locations of one or more electrodes, graphical depictions of one or more target or candidate locations, alphanumeric representations of one or more values, graphical depictions or actual images of implanted electrodes and/or leads, etc. For example, the display apparatus 130 may include a liquid crystal display, an organic light-emitting diode screen, a touchscreen, a cathode ray tube display, etc.

The graphical user interfaces 132 displayed by the display apparatus 130 may include, or display, one or more regions used to display graphical depictions, to display images, to allow selection of one or more regions or areas of such graphical depictions and images, etc. As used herein, a "region" of a graphical user interface 132 may be defined as a portion of the graphical user interface 132 within which information may be displayed or functionality may be performed. Regions may exist within other regions, which may be displayed separately or simultaneously. For example, smaller regions may be located within larger regions, regions may be located side-by-side, etc. Additionally, as used herein, an "area" of a graphical user interface 132 may be defined as a portion of the graphical user interface 132 located with a region that is smaller than the region it is located within.

The processing programs or routines stored and/or executed by the computing apparatus 140 may include programs or routines for computational mathematics, matrix mathematics, decomposition algorithms, compression algorithms (e.g., data compression algorithms), calibration algorithms, image construction algorithms, signal processing algorithms (e.g., Fourier transforms, fast Fourier transforms, etc.), standardization algorithms, comparison algorithms, vector mathematics, or any other processing required to implement one or more exemplary methods and/or processes described herein. Data stored and/or used by the computing apparatus 140 may include, for example, image data from the imaging apparatus 120, electrical signal data from the electrode apparatus 110, graphics (e.g., graphical elements, icons, buttons, windows, dialogs, pull-down menus, graphic areas, graphic regions, 3D graphics, etc.), graphical user interfaces, results from one or more processing programs or routines employed according to the disclosure herein, or any other data that may be necessary for carrying out the one and/or more processes or methods described herein.

In one or more embodiments, the exemplary systems, methods, and interfaces may be implemented using one or more computer programs executed on programmable computers, such as computers that include, for example, processing capabilities, data storage (e.g., volatile or non-volatile memory and/or storage elements), input devices, and output devices. Program code and/or logic described herein may be applied to input data to perform functionality described herein and generate desired output information. The output information may be applied as input to one or more other devices and/or methods as described herein or as would be applied in a known fashion.

The one or more programs used to implement the systems, methods, and/or interfaces described herein may be provided using any programmable language, e.g., a high level procedural and/or object orientated programming language that is suitable for communicating with a computer system. Any such programs may, for example, be stored on any suitable device, e.g., a storage media, that is readable by a general or special purpose program running on a computer system (e.g., including processing apparatus) for configuring and operating the computer system when the suitable device is read for performing the procedures described herein. In other words, at least in one embodiment, the exemplary systems, methods, and/or interfaces may be implemented using a computer readable storage medium, configured with a computer program, where the storage medium so configured causes the computer to operate in a specific and predefined manner to perform functions described herein. Further, in at least one embodiment, the exemplary systems, methods, and/or interfaces may be described as being implemented by logic (e.g., object code) encoded in one or more non-transitory media that includes code for execution and, when executed by a processor, is operable to perform operations such as the methods, processes, and/or functionality described herein.

The computing apparatus 140 may be, for example, any fixed or mobile computer system (e.g., a controller, a microcontroller, a personal computer, minicomputer, tablet computer, etc.). The exact configuration of the computing apparatus 130 is not limiting, and essentially any device capable of providing suitable computing capabilities and control capabilities (e.g., graphics processing, etc.) may be used. As described herein, a digital file may be any medium (e.g., volatile or non-volatile memory, a CD-ROM, a punch card, magnetic recordable tape, etc.) containing digital bits (e.g., encoded in binary, trinary, etc.) that may be readable and/or writeable by computing apparatus 140 described herein. Also, as described herein, a file in user-readable format may be any representation of data (e.g., ASCII text, binary numbers, hexadecimal numbers, decimal numbers, graphically, etc.) presentable on any medium (e.g., paper, a display, etc.) readable and/or understandable by a user.

In view of the above, it will be readily apparent that the functionality as described in one or more embodiments according to the present disclosure may be implemented in any manner as would be known to one skilled in the art. As such, the computer language, the computer system, or any other software/hardware which is to be used to implement the processes described herein shall not be limiting on the scope of the systems, processes or programs (e.g., the functionality provided by such systems, processes or programs) described herein.

As used herein, mechanical motion data may be defined as data relating to the mechanical motion of one or more regions of a patient's heart such as portions of the walls of the patient's heart. It may be desirable for target locations in a patient's heart for implantable electrode placement to also have late mechanical motion timing (e.g., later motion than other portions of the patient's heart, motion that is later than a selected threshold value or time, etc.). Mechanical motion data may be measured and determined using the exemplary imaging apparatus 120 and the computing apparatus 140.

For example, a plurality of frames of image data may be captured using the imaging apparatus 120 and analyzed by the computing apparatus to determine mechanical motion information, or data, of one or more regions of a patient's heart.

Local 3D motion of the heart wall can be decomposed into two components: the first component expresses change of distances between neighboring points and is referenced as a strain (e.g., contraction, when distances decrease or expansion, when distances increase, etc.) and the second non-strain component may not involve change of distances between neighboring points and may involve translation and/or rotation. The strain may be anisotropic. Specifically, a circumferential strain when cross sections (segments) perpendicular to the long axis of a heart chamber change length may be differentiated from a longitudinal strain when lines substantially parallel to long axis change length. The exemplary imaging apparatus 120 described herein may be configured to provide image data to provide graphical depictions of contraction and expansion as a change in scale of a blood vessel tree, or in other words, as a change of distance between points, while rotation and translation are visualized without change of distances.

The imaging apparatus 120, which may be a computerized X-ray machine, may be directed at the patient's heart and activated to produce a time sequence of X-ray images of the heart area at the field of view. In order to expose blood vessels (e.g., such as the coronary vessels) at the heart area under view, the X-ray images may be preferably obtained under angiography procedure by injecting contrast agent to the patient. Where the vessels to be detected are the coronary veins, the angiography may be carried out after a balloon is inserted and inflated inside the vein, e. g., the coronary sinus, so as to prevent blood flow from dispersing the contrast agent before the images are taken.

For example, a time sequence of two-dimensional X-ray projection images may be captured by imaging apparatus of FIG. 1 and stored by the computing apparatus 140. The two-dimensional images may be angiograms taken after the patient has been injected with contrast agent. The time sequence may include "snapshots" (e.g., angiographic cine-runs) of the coronary vessel under the same projection angle during at least part of the cardiac cycle of the patient. Further, the projection direction may be selected to be substantially orthogonal to the surface of the heart at the region of interest or to the main velocity component thereof.

The blood vessels of interest may be tracked through the time sequence of images in order to identify the movements of the vessels through at least part of the cardiac cycle. Tracking of blood vessels through the time sequence of images may be performed by calculation of local area transformations from one frame to the next, or by tracking selected control points in the detected vessels. Yet, in accordance with some embodiments, tracking the vessels may be performed by a hybrid combination of the two methods.

Examples of systems and/or imaging apparatus configured to capture and determine mechanical motion information may be described in U.S. Pat. App. Pub. No. 2005/0008210 to Evron et al. published on Jan. 13, 2005, U.S. Pat. App. Pub. No. 2006/0074285 to Zarkh et al. published on Apr. 6, 2006, U.S. Pat. App. Pub. No. 2011/0112398 to Zarkh et al. published on May 12, 2011, U.S. Pat. App. Pub. No. 2013/0116739 to Brada et al. published on May 9, 2013, U.S. Pat. No. 6,980,675 to Evron et al. issued on Dec. 27, 2005, U.S. Pat. No. 7,286,866 to Okerlund et al. issued on Oct. 23, 2007, U.S. Pat. No. 7,308,297 to Reddy et al. issued on Dec. 11, 2011, U.S. Pat. No. 7,308,299 to Burrell et al. issued on Dec. 11, 2011, U.S. Pat. No. 7,321,677 to Evron et al. issued on Jan. 22, 2008, U.S. Pat. No. 7,346,381 to Okerlund et al. issued on Mar. 18, 2008, U.S. Pat. No. 7,454,248 to Burrell et al. issued on Nov. 18, 2008, U.S. Pat. No. 7,499,743 to Vass et al. issued on Mar. 3, 2009, U.S. Pat. No. 7,565,190 to Okerlund et al. issued on Jul. 21, 2009, U.S. Pat. No. 7,587,074 to Zarkh et al. issued on Sep. 8, 2009, U.S. Pat. No. 7,599,730 to Hunter et al. issued on Oct. 6, 2009, U.S. Pat. No. 7,613,500 to Vass et al. issued on Nov. 3, 2009, U.S. Pat. No. 7,742,629 to Zarkh et al. issued on Jun. 22, 2010, U.S. Pat. No. 7,747,047 to Okerlund et al. issued on Jun. 29, 2010, U.S. Pat. No. 7,778,685 to Evron et al. issued on Aug. 17, 2010, U.S. Pat. No. 7,778,686 to Vass et al. issued on Aug. 17, 2010, U.S. Pat. No. 7,813,785 to Okerlund et al. issued on Oct. 12, 2010, U.S. Pat. No. 7,996,063 to Vass et al. issued on Aug. 9, 2011, U.S. Pat. No. 8,060,185 to Hunter et al. issued on Nov. 15, 2011, and U.S. Pat. No. 8,401,616 to Verard et al. issued on Mar. 19, 2013, each of which are incorporated herein by reference in their entireties.

Figure 2:
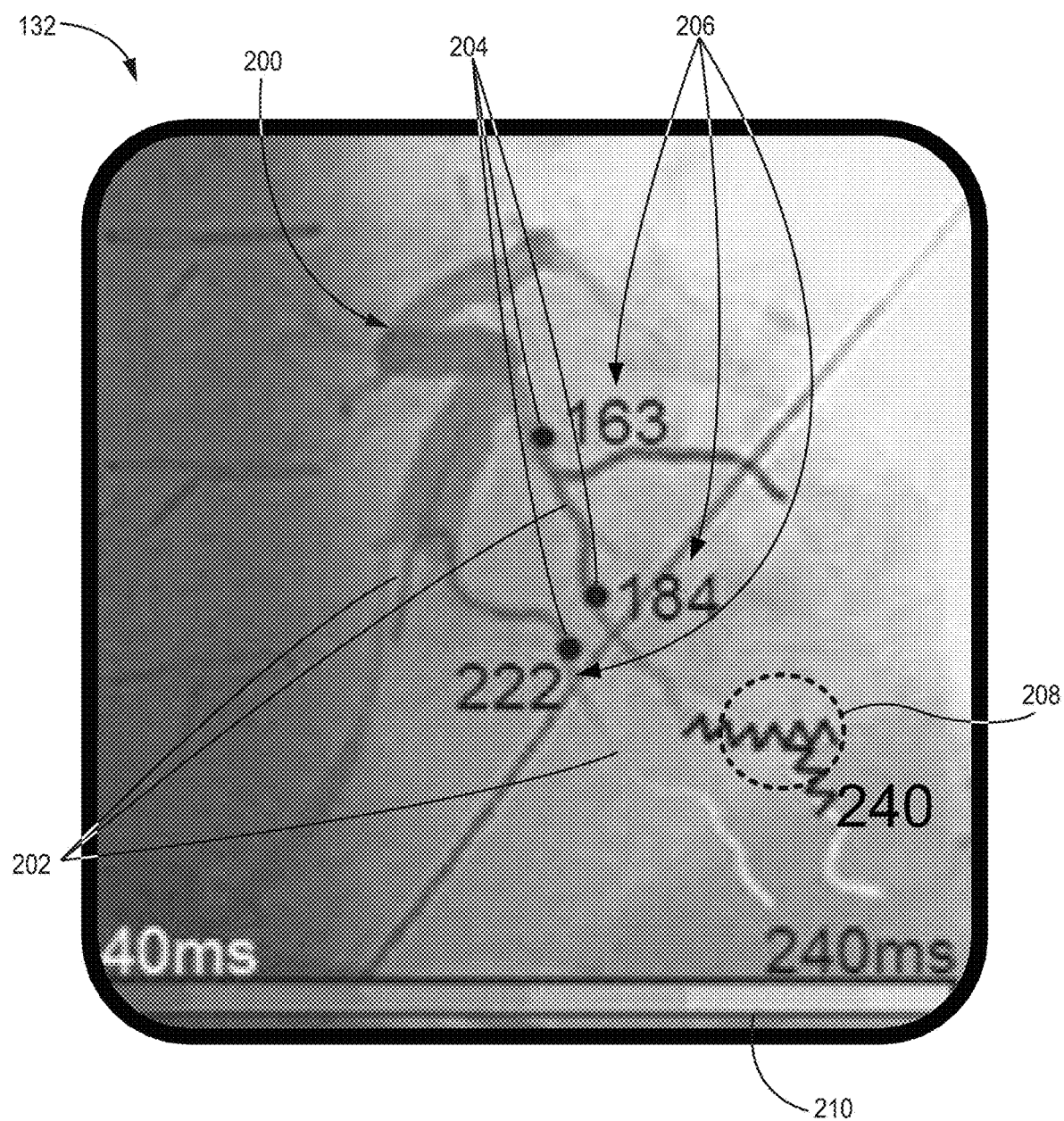
FIG. 2 is an exemplary graphical user interface depicting mechanical motion information of a portion of a patient's heart.

Mechanical motion data, or information, may be provided to a user to assist the user in selecting a location for an implantable electrode. An exemplary graphical user interface 132 depicting mechanical motion information of a portion of a patient's heart is shown in FIG. 2. The graphical user interface 132 is configured to depict at least a portion of blood vessel anatomy 200 of a patient's heart and mechanical motion information with respect to the blood vessel anatomy 200. As shown, the blood vessel anatomy 200 is the coronary sinus located proximate the left ventricle of a patient. The blood vessel anatomy 200 further includes a plurality of branches 202 of, e.g., the coronary sinus. Each branch, as well as multiple locations within each branch, may provide candidate site regions or locations for implantable electrodes. Implantable electrodes may be implanted in locations having the latest mechanical motion time. As used herein, mechanical motion time may be the time between the onset of contraction and a common fiducial point such as e.g., onset of QRS depolarization complex for that particular cardiac cycle on an external ECG lead.

As shown, the mechanical motion time may be represented by color/grey scaling, or coding, the blood vessel anatomy 200 according to a scale 210. As shown, the scale 210 extends from dark grey/colors, which correspond to about 40 milliseconds (ms), to light white/colors, which correspond to about 240 ms. As such, a user may view the graphical user interface 132 to see, or ascertain, the mechanical motions times of the different regions of the heart (e.g., different regions of the blood vessel anatomy). Additionally, the graphical user interface 132 may alphanumerically depict the mechanical motion times 206 for one or more regions 204 identified on blood vessel anatomy 200. Using the graphical user interface 132, a user may select a target, or candidate, location 208 for implantation that may have the latest, or near the latest, mechanical motion time. As shown, the target location 208 may have a mechanical motion time of 240 ms.

It may be desirable for target or candidate site regions or locations for implantable electrode placement to also have late electrical activation times, in addition to late mechanical motion times. In addition or alternatively, the electrical activation times can be used in place of the mechanical activation times.

Figure 3A:
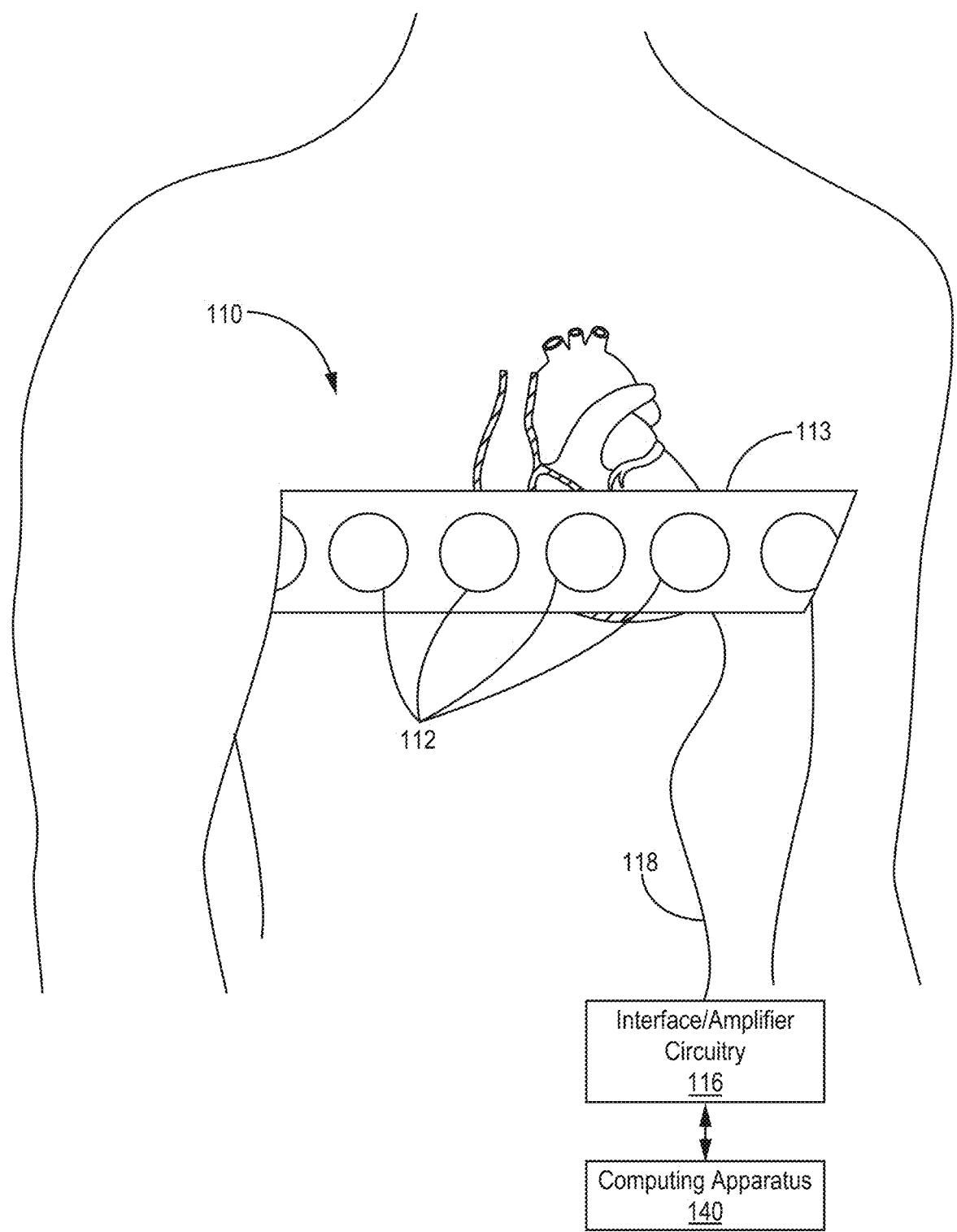
FIG. 3A is a schematic diagram of exemplary external electrode apparatus for measuring torso-surface potentials.
Figure 3B:
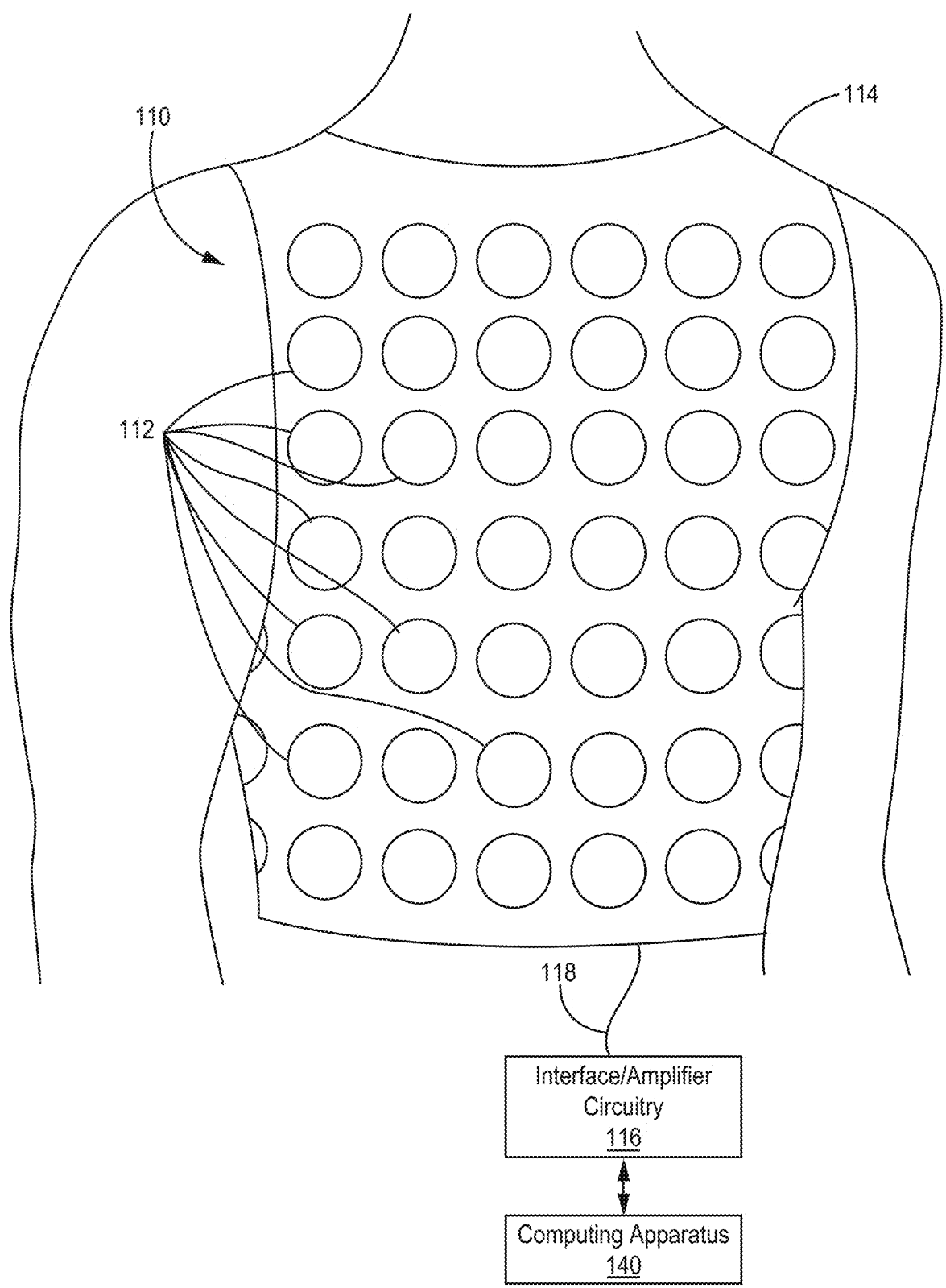
FIG. 3B is a schematic diagram of another exemplary external electrode apparatus for measuring torso-surface potentials.

Electrical activation data of one or more regions of a patient's heart may be determined using electrode apparatus 110 as shown in FIG. 1 and in FIGS. 3A-3B. The exemplary electrode apparatus 110 may be configured to measure body-surface potentials of a patient 14 and, more particularly, torso-surface potentials of a patient 14. As shown in FIG. 3A, the exemplary electrode apparatus 110 may include a set, or array, of electrodes 112, a strap 113, and interface/amplifier circuitry 116. The electrodes 112 may be attached, or coupled, to the strap 113 and the strap 113 may be configured to be wrapped around the torso of patient 14 such that the electrodes 112 surround the patient's heart. As further illustrated, the electrodes 112 may be positioned around the circumference of a patient 14, including the posterior, lateral, posterolateral, and anterior locations of the torso of patient 14.

Further, the electrodes 112 may be electrically connected to interface/amplifier circuitry 116 via wired connection 118. The interface/amplifier circuitry 116 may be configured to amplify the signals from the electrodes 112 and provide the signals to the computing apparatus 140. Other exemplary systems may use a wireless connection to transmit the signals sensed by electrodes 112 to the interface/amplifier circuitry 116 and, in turn, the computing apparatus 140, e.g., as channels of data.

Although in the example of FIG. 3A the electrode apparatus 110 includes a strap 113, in other examples any of a variety of mechanisms, e.g., tape or adhesives, may be employed to aid in the spacing and placement of electrodes 112. In some examples, the strap 113 may include an elastic band, strip of tape, or cloth. In other examples, the electrodes 112 may be placed individually on the torso of a patient 14. Further, in other examples, electrodes 112 (e.g., arranged in an array) may be part of, or located within, patches, vests, and/or other means of securing the electrodes 112 to the torso of the patient 14.

The electrodes 112 may be configured to surround the heart of the patient 14 and record, or monitor, the electrical signals associated with the depolarization and repolarization of the heart after the signals have propagated through the torso of patient 14. Each of the electrodes 112 may be used in a unipolar configuration to sense the torso-surface potentials that reflect the cardiac signals. The interface/amplifier circuitry 116 may also be coupled to a return or indifferent electrode (not shown) that may be used in combination with each electrode 112 for unipolar sensing. In some examples, there may be about 12 to about 50 electrodes 112 spatially distributed around the torso of patient. Other configurations may have more or fewer electrodes 112.

The computing apparatus 140 may record and analyze the torso-surface potential signals sensed by electrodes 112 and amplified/conditioned by the interface/amplifier circuitry 116. The computing apparatus 140 may be configured to analyze the signals from the electrodes 112 to provide surrogate electrical activation data such as surrogate electrical activation times, e.g., representative of actual, or local, electrical activation times of one or more regions of the patient's heart as will be further described herein. Measurement of activation times can be performed by picking an appropriate fiducial point (e.g., peak values, minimum values, minimum slopes, maximum slopes, zero crossings, threshold crossings, etc. of a near or far-field EGM) and measuring time between the onset of cardiac depolarization (e.g., onset of QRS complexes) and the appropriate fiducial point (e.g., within the electrical activity). The activation time between the onset of the QRS complex (or the peak Q wave) to the fiducial point may be referred to as q-LV time.

Additionally, the computing apparatus 140 may be configured to provide graphical user interfaces depicting the surrogate electrical activation times obtained using the electrode apparatus 110. Exemplary systems, methods, and/or interfaces may noninvasively use the electrical information collected using the electrode apparatus 110 to identify, select, and/or determine whether one or more regions of a patient's heart may be optimal, or desirable, for implantable electrode placement.

FIG. 3B illustrates another exemplary electrode apparatus 110 that includes a plurality of electrodes 112 configured to surround the heart of the patient 14 and record, or monitor, the electrical signals associated with the depolarization and repolarization of the heart after the signals have propagated through the torso of patient 14. The electrode apparatus 110 may include a vest 114 upon which the plurality of electrodes 112 may be attached, or to which the electrodes 112 may be coupled. In at least one embodiment, the plurality, or array, of electrodes 112 may be used to collect electrical information such as, e.g., surrogate electrical activation times. Similar to the electrode apparatus 110 of FIG. 3A, the electrode apparatus 110 of FIG. 3B may include interface/amplifier circuitry 116 electrically coupled to each of the electrodes 112 through a wired connection 118 and configured to transmit signals from the electrodes 112 to computing apparatus 140. As illustrated, the electrodes 112 may be distributed over the torso of patient 14, including, for example, the anterior, lateral, and posterior surfaces of the torso of patient 14.

The vest 114 may be formed of fabric with the electrodes 112 attached to the fabric. The vest 114 may be configured to maintain the position and spacing of electrodes 112 on the torso of the patient 14. Further, the vest 114 may be marked to assist in determining the location of the electrodes 112 on the surface of the torso of the patient 14. In some examples, there may be about 25 to about 256 electrodes 112 distributed around the torso of the patient 14, though other configurations may have more or fewer electrodes 112.

As described herein, the electrode apparatus 110 may be configured to measure electrical information (e.g., electrical signals) representing different regions of a patient's heart. More specifically, activation times of different regions of a patient's heart can be approximated from surface electrocardiogram (ECG) activation times measured using surface electrodes in proximity to surface areas corresponding to the different regions of the patient's heart.

Figure 4:
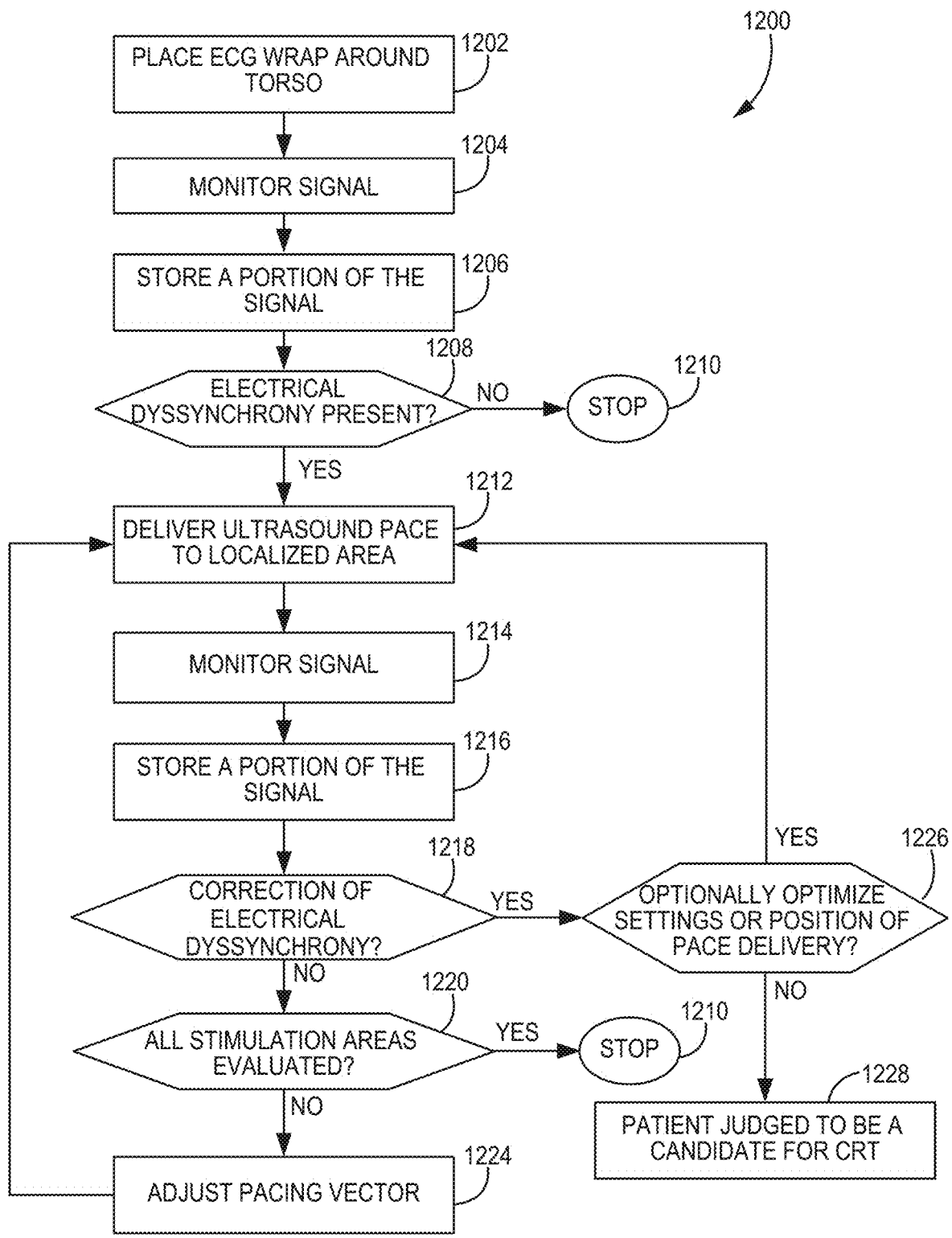
FIG. 4 is a flow diagram of depicting the steps involved in determining whether a patient is a candidate for cardiac resynchronization therapy.

FIG. 4 is a method 1200 for determining whether a patient is a candidate for CRT. At block 1202, the electrode apparatus 110 is placed over the torso of the patient. At block 1204, data is collected from unipolar signals acquired during intrinsic conduction from the electrode apparatus 110, as described in U.S. patent application Ser. No. 13/462,480 filed on May 2, 2012, ASSESSING INTRACARDIAC ACTIVATION PATTERNS, and assigned to the assignee of the present invention, the disclosure of which is incorporated by reference in its entirety herein. At block 1206, a portion of the signal is stored into memory. At block 1208, a determination is made as to whether electrical dyssynchrony is present. If electrical dyssynchrony is not present, the patient is not a candidate for CRT and the procedure is terminated at block 1210. Mechanical dyssynchrony can be established according to CardioGuide type imaging or according to ultrasonic strain imaging. Ultrasound strain imaging (via speckle tracking) can be used as a means to determine dyssynchrony (thus combining ultrasound imaging with HIFU for a completely ultrasound system). One or more embodiments, relate to determining dyssynchrony (i.e., the spread or standard deviation of strain in different locations) rather than focusing on the single location with the latest activation. If electrical dyssynchrony is present, then ultrasound energy (e.g. high intensity focused ultrasound (HIFU) is delivered to a localized tissue area at block 1212. The user can move the transducer over the skin in a location that the user would like to evaluate a location from which to pace. For example, HIFU at up to 3 MegaPascal (MPa) Sound Pressure Level (SPL) can be used to stimulate cardiac tissue. At block 1214, signals are monitored via electrical apparatus 110. The data collected from unipolar signals acquired during delivery of the ultrasonic energy is stored into memory at block 1216. At block 1218, a determination is made as to whether ultrasonic pace in the localized tissue corrected or minimized the electrical dyssynchrony. If the ultrasonic pacing did correct the electrical dyssynchrony, then the control of the logic is transferred to block 1226 which optionally optimizes pace control settings (A-V delay, V-V delay, pace output, etc.) and/or pacing location. In contrast, if the ultrasonic pacing did not correct the electrical dyssynchrony, then the control of the logic is transferred to block 1220, in which a determination is made as to whether another location from which to deliver pacing energy may be more appropriate. If all stimulation areas have been evaluated, then the control of the logic is transferred to block 1210 and the evaluation is stopped. The patient is not a CRT candidate. If all stimulation areas have not been evaluated, then the control of the logic is transferred to block 1224 such that another tissue location for stimulation is evaluated through processing blocks 1212 through 1220. A patient is judged to be a candidate for CRT at block 1228 once a determination is made that the ultrasonic pace corrects or minimizes the electrical dyssynchrony.

Figure 5:
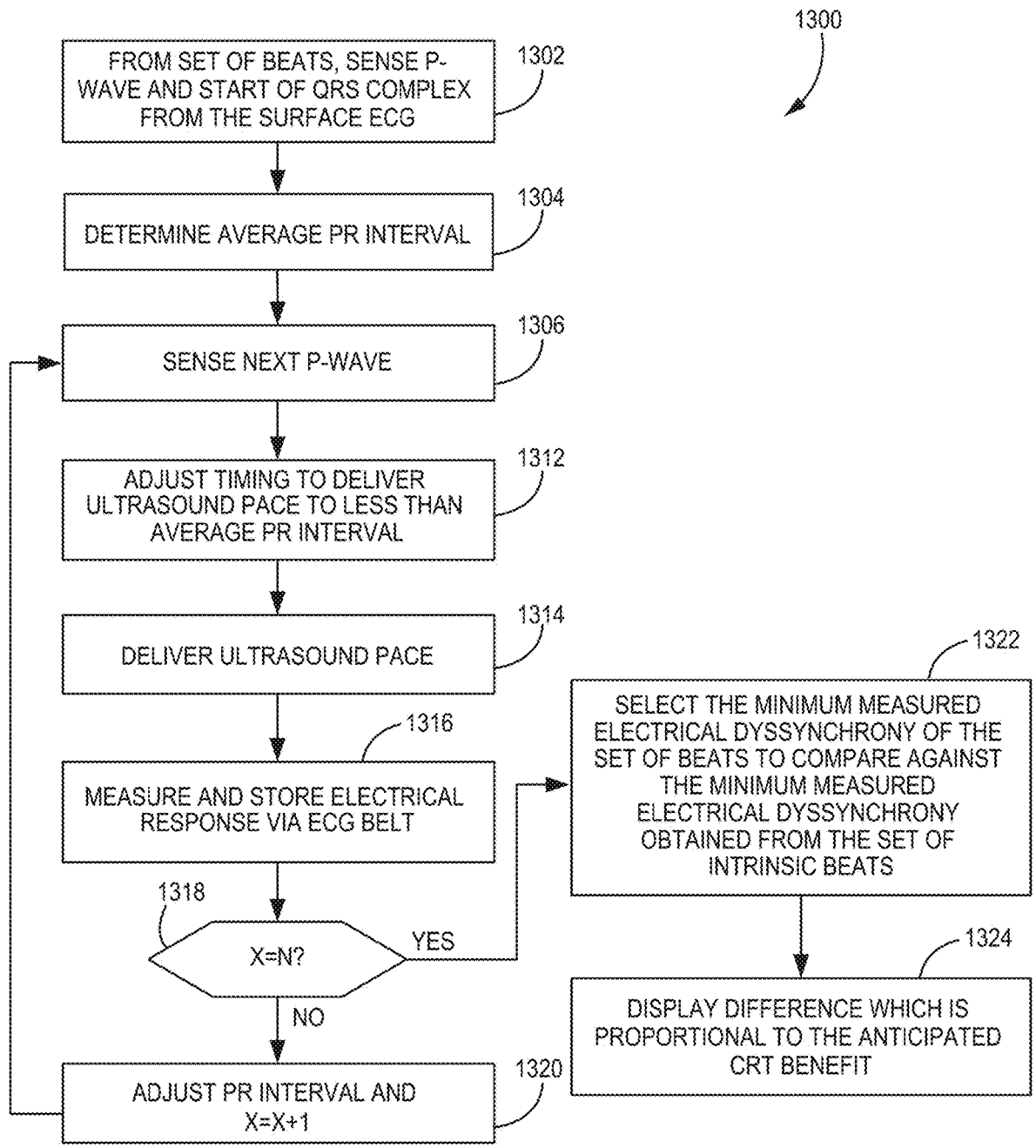
FIG. 5 is a flow diagram of an exemplary timing algorithm of an ultrasonic pace when a patient is not experiencing atrial fibrillation.

FIG. 5 is a flow diagram of an exemplary timing algorithm for delivering ultrasonic energy when a patient is not experiencing atrial fibrillation. At block 1302, from a small group of beats (e.g. 5 beats), sensing occurs of the P-wave and start of the QRS complex from the surface ECG. The goal is to determine the minimum electrical dyssynchrony possible from a given pacing location. This requires fusion of the paced depolarization with the intrinsic ventricular depolarization. Thus, timing of the ultrasound pace with respect to intrinsic depolarization of the ventricle is important. Therefore, the ultrasonic pacing and dyssynchrony measurements are conducted over a range of timings with respect to the expected or anticipated intrinsic ventricular depolarization. At block 1304, the average PR interval, referred to as the "expected PR interval", is determined from the small group of beats. The PR interval is the time required for the electrical impulse to leave the SA node and travel through the atria, AV node, the bundle branches, and the purkinje network. The PR interval includes the P-wave and a short flat line that follows the P-wave. At block 1306, the next P-wave is sensed through the electrical apparatus 110. The ultrasound pace is timed to be slightly less than the expected PR interval. At block 1312, the timing to deliver the ultrasonic pace is adjusted. For example, the timing to deliver the ultrasonic pace is less than the expected PR interval. At block 1314, the ultrasonic pace is delivered to the tissue. At block 1316, the electrical response of the tissue to the ultrasonic pace is measured and stored into memory. At block 1318, a determination is made as to whether all of the responses to each paced beats have been collected and stored. The total number of paced beats is represented by N while X serves as a counter that is initialized to zero before method 1300 has begun. If not, the control of the logic is transferred to block 1320 to increment the beat counter such that X=X+1. Additionally, the PR interval is adjusted. For example, a sweep of PR intervals evaluated over perhaps 6 beats, firing the ultrasound pace at, for example, expected PR-60 ms, expected PR-50, expected PR-40, expected PR-30, expected PR-20, expected PR-10. The dyssynchrony is measured and stored each time from the electrical apparatus 110 (e.g. ECG belt, vest etc.). The minimum measured electrical dyssynchrony of the 6 beats is then compared to the minimum electrical dyssynchrony of the stored 6 intrinsic beats. The difference between the minimum electrical dyssynchrony of the 6 paced beats to the minimum electrical dyssynchrony of the 6 intrinsic beats is proportional to the anticipated CRT benefit. At block 1324, the difference in minimum electrical dyssynchrony between the paced and intrinsic beats is displayed on the graphical user interface (GUI) of the computer. The GUI will display a number or a color visualization that either indicates that CRT is beneficial for a patient or is not beneficial. In either situation, more effective treatment is able to be delivered since each CRT candidate is more definitively identified. Additionally, healthcare costs are reduced by eliminating patients who may not be CRT candidates.

Figure 6:
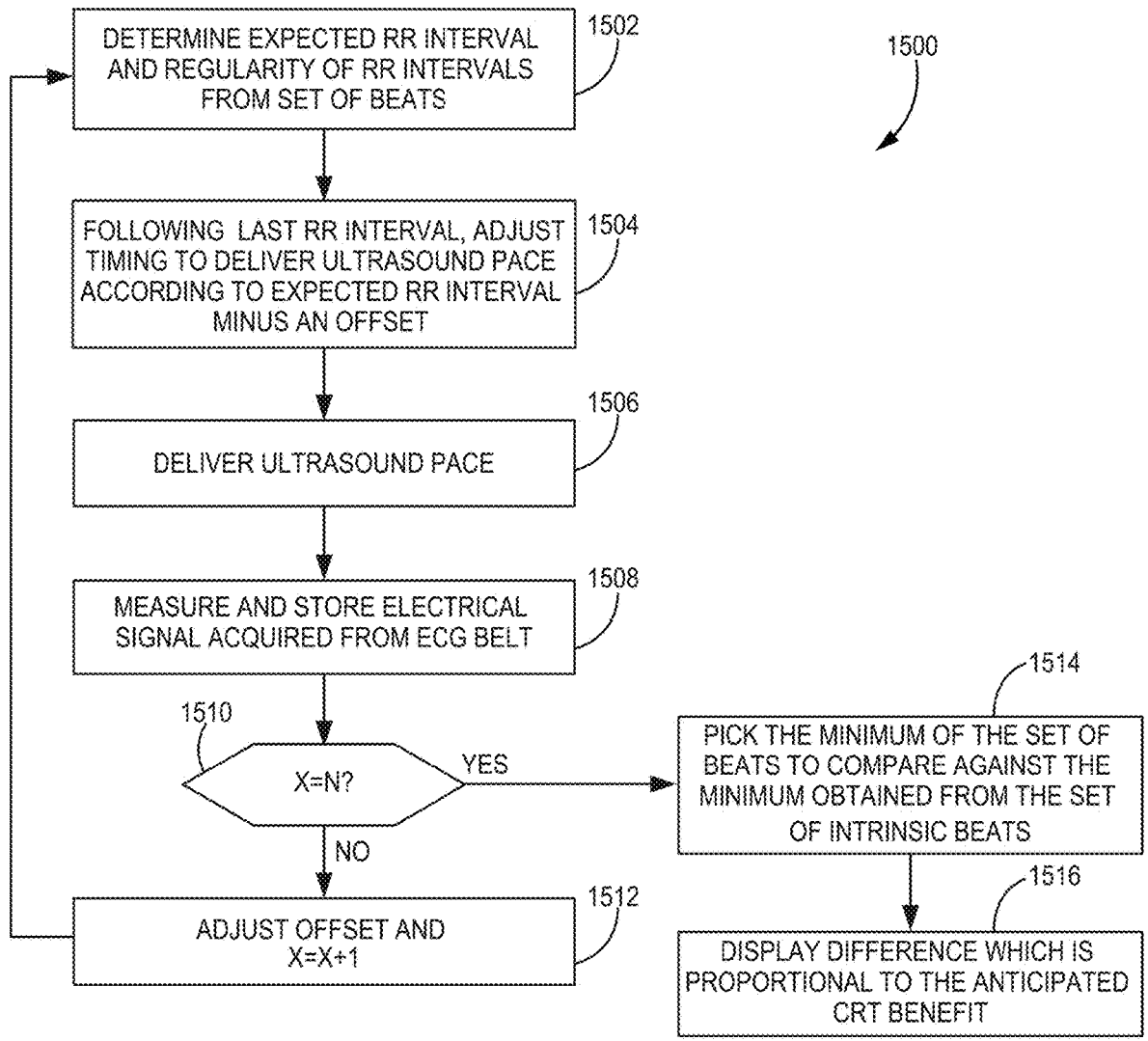
FIG. 6 is a flow diagram of yet another exemplary timing algorithm of an ultrasonic pace when a patient is not experiencing atrial fibrillation.

FIG. 6 is a flow diagram of another exemplary timing algorithm for delivering ultrasonic energy when a patient is not experiencing atrial fibrillation. Method 1500 begins at block 1502 in which a determination is made as to whether the expected RR interval and the regularity of RR intervals from a group of beats (e.g., 5 beats). The expected RR interval can be the average RR intervals for the total number of beats. Following the last RR interval, the delivery of the ultrasonic pace is timed according to the expected RR interval minus an offset (e.g., 60 ms) at block 1504. The offset could depend on the measured regularity, and if the regularity is too high, treat as if the patient is in AF as described below. At block 1506, the ultrasonic pace is delivered. The electrical response, acquired via the electrical apparatus 110, is measured and stored into memory at block 1508. At block 1510, a determination is made as to whether the total number N of pre-specified paced beats have been evaluated. If not, the beat counter X is incremented by 1 and the process of blocks 1502 through 1508 is repeated with a sweep of offset values (60 ms, 50 ms, 40 ms, 30 ms, 20 ms, 10 ms), and measure the dyssynchrony each time from the ECG belt. Again, pick the minimum electrical dyssynchrony associated with the 6 paced beats is compared minimum electrical dyssynchrony associated with the 6 intrinsic beats. The minimum electrical dyssynchrony difference between the paced and intrinsic beats is proportional to the anticipated CRT benefit.

With respect to the methods depicted in FIGS. 5-6, if an R-wave is sensed before the ultrasonic pace is delivered, inhibit the pace and start the measurement sequence over.

Figure 7:
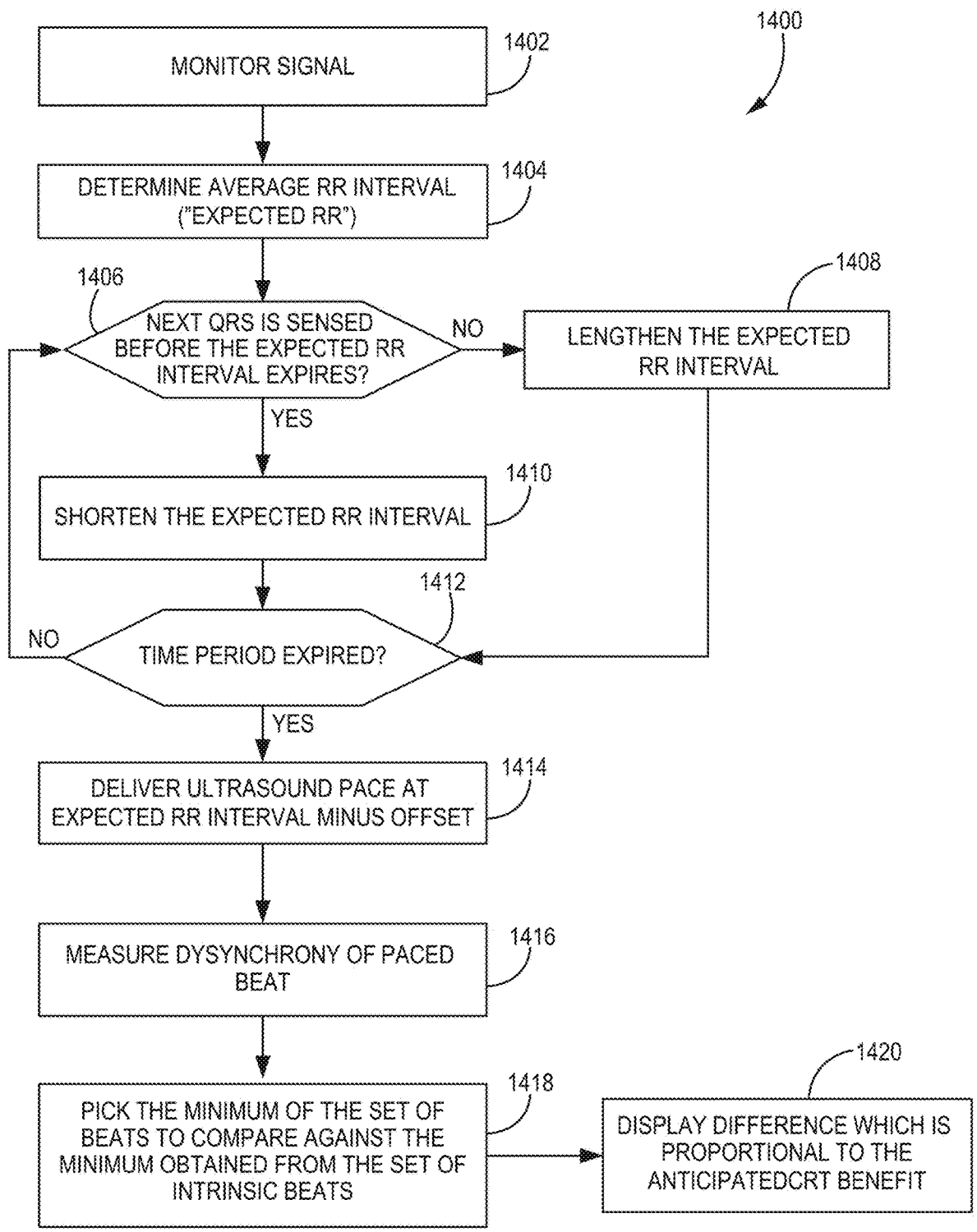
FIG. 7 is a flow diagram of yet another exemplary timing algorithm of an ultrasonic pace when a patient is not experiencing atrial fibrillation.

FIG. 7 depicts a timing algorithm method 1400 when the patient is in atrial fibrillation or, when the patient's rhythm is highly irregular. At block 1402, signals from electrical apparatus 110 are monitored in response to intrinsic beats. Thereafter, an AF response algorithm for a period of time (e.g. 30 seconds). For example, at block 1404, an average RR interval (e.g. average of 10 beats) is determined. The initial RR interval is also referred to as the "expected RR interval". At block 1406, if the next QRS is sensed before the expected RR interval expires, shorten the expected RR interval by e.g., 30 ms at block 1410. If the next QRS is longer than the expected RR interval, lengthen the expected RR interval by e.g., 30 ms at block 1408. Repeat blocks 1406 through 1410 for a pre-specified period of time e.g. 30 seconds at block 1412. At the end of time period at block 1412, trigger the ultrasonic pace at the expected RR interval minus an offset (like 50 ms) at block 1414. Continue the beat-to-beat updating of the expected RR interval and deliver the ultrasound pace at the expected RR interval (minus the 50 ms offset) every e.g. 10th beat. Repeat the process for a pre-specified number of paces (e.g. 10 paces) have been delivered, measuring the dyssynchrony of every paced beat. At block 1416, pick the minimum of the 10 paced beats to compare against the minimum obtained from 10 intrinsic beats. The difference is proportional to the anticipated CRT benefit.

The present disclosure establishes that HIFU and surface electrodes can be used to non-invasively determine whether a patient will derive benefit from the CRT prior to implantation of a cardiac rhythm device. Additionally, the present disclosure is able to determine optimal site for placement of one or more ventricular pacing leads. Moreover, programming of optimal device parameters is achieved. For example, electrodes on multi-polar right or left ventricular leads are selected. In addition, the optimal timing (e.g. A-V delay, V-V delay) of the pacing pulses delivered to the electrodes is selected using HIFU. However, optimally, pacing control parameters can be optimized by using the ECG belt.

Figure 8:
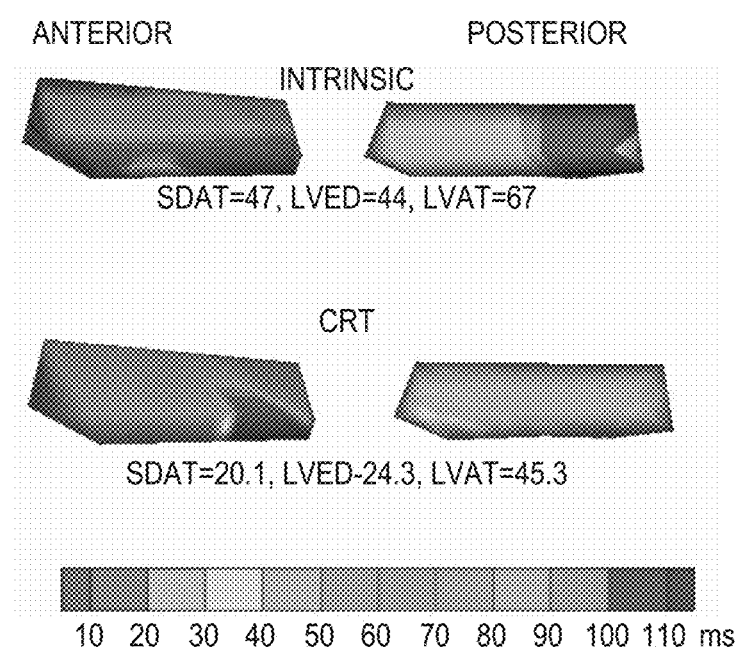
FIG. 8 is a series of simulated isochrone maps of torso-surface activation times for typical widened QRS intrinsic rhythm and a narrowed QRS after CRT pacing.

FIG. 8 depicts a series of simulated isochrone maps of torso-surface activation times for typical widened QRS intrinsic rhythm and a narrowed QRS after CRT pacing. Applying CRT is shown to narrow the QRS thereby improving the cardiac condition of the patient from the widened QRS.

Figure 9:
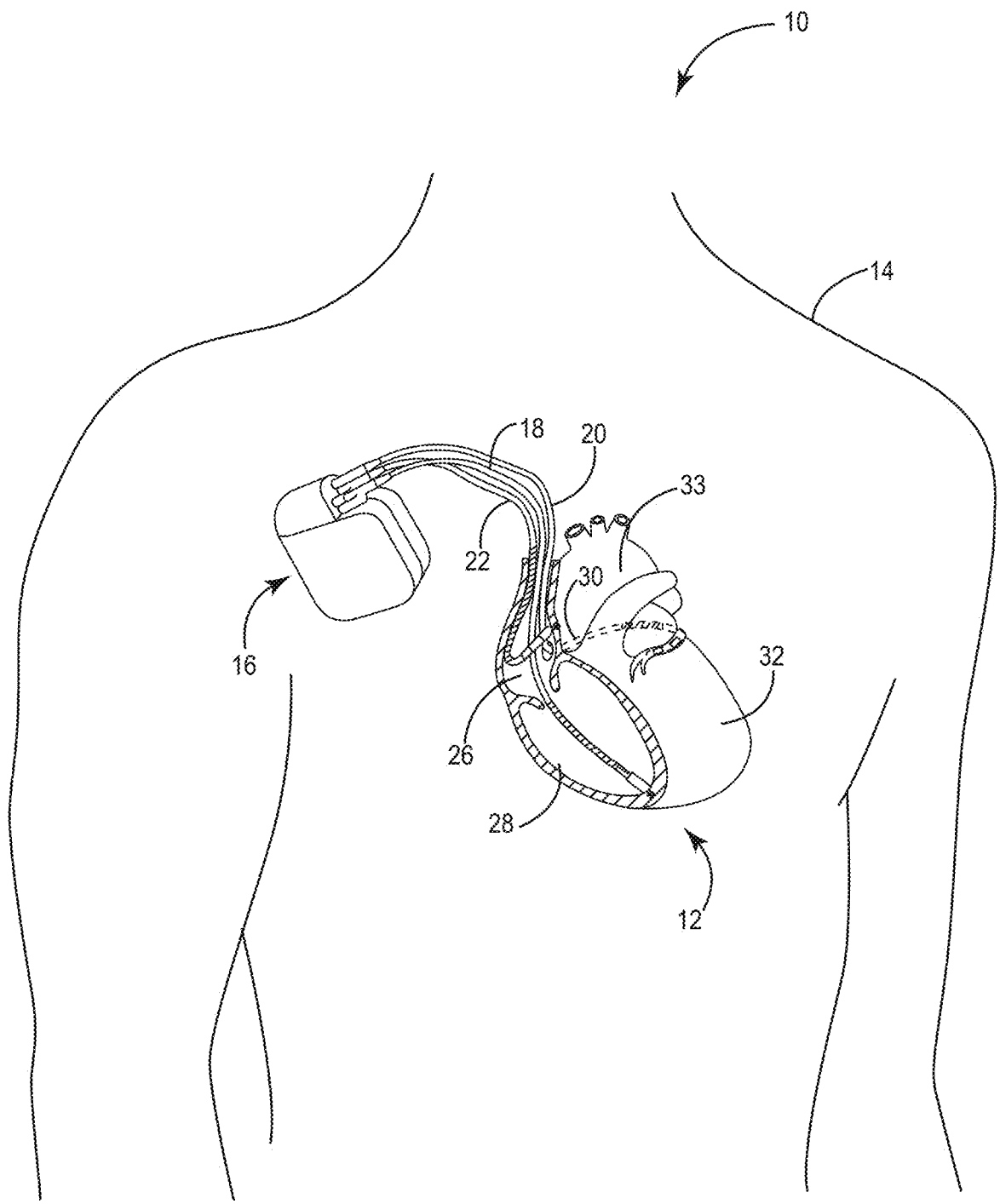
FIG. 9 is a diagram of an exemplary system including an exemplary implantable medical device (IMD).

FIG. 9 is a conceptual diagram illustrating an exemplary therapy system 10 that is subsequently implanted into a patient to deliver pacing therapy to a patient 14 after determining whether CRT is beneficial to a patient. For a variety of reasons, a medical electrical lead may need to be repositioned. For example, a medical electrical lead can migrate or move away from its position. Alternatively, tissue where the pacing electrode is placed may stop responding to paces delivered by the IMD. In either of these scenarios, the method disclosed herein can be used select a target location and determine whether it may be an optimal location from which to pace.

The therapy system 10 may include an implantable medical device 16 (IMD), which may be coupled to leads 18, 20, 22. The IMD 16 may be, e.g., an implantable pacemaker, cardioverter, and/or defibrillator, that provides electrical signals to the heart 12 of the patient 14 via electrodes coupled to one or more of the leads 18, 20, 22 (e.g., electrodes that may be implanted in accordance with the description herein, such as, with use of non-invasive selection of implantation site regions).

The leads 18, 20, 22 extend into the heart 12 of the patient 14 to sense electrical activity of the heart 12 and/or to deliver electrical stimulation to the heart 12. In the example shown in FIG. 9, the right ventricular (RV) lead 18 extends through one or more veins (not shown), the superior vena cava (not shown), and the right atrium 26, and into the right ventricle 28. The left ventricular (LV) coronary sinus lead 20 extends through one or more veins, the vena cava, the right atrium 26, and into the coronary sinus 30 to a region adjacent to the free wall of the left ventricle 32 of the heart 12. The right atrial (RA) lead 22 extends through one or more veins and the vena cava, and into the right atrium 26 of the heart 12.

The IMD 16 may sense, among other things, electrical signals attendant to the depolarization and repolarization of the heart 12 via electrodes coupled to at least one of the leads 18, 20, 22. The IMD 16 may be configured to determine or identify effective electrodes located on the leads 18, 20, 22 using the exemplary methods and processes described herein. In some examples, the IMD 16 provides pacing therapy (e.g., pacing pulses) to the heart 12 based on the electrical signals sensed within the heart 12. The IMD 16 may be operable to adjust one or more parameters associated with the pacing therapy such as, e.g., AV delay and other various timings, pulse wide, amplitude, voltage, burst length, etc. Further, the IMD 16 may be operable to use various electrode configurations to deliver pacing therapy, which may be unipolar, bipolar, quadripolaor, or further multipolar. For example, a multipolar lead may include several electrodes that can be used for delivering pacing therapy. Hence, a multipolar lead system may provide, or offer, multiple electrical vectors to pace from. A pacing vector may include at least one cathode, which may be at least one electrode located on at least one lead, and at least one anode, which may be at least one electrode located on at least one lead (e.g., the same lead, or a different lead) and/or on the casing, or can, of the IMD. While improvement in cardiac function as a result of the pacing therapy may primarily depend on the cathode, the electrical parameters like impedance, pacing threshold voltage, current drain, longevity, etc. may be more dependent on the pacing vector, which includes both the cathode and the anode. The IMD 16 may also provide defibrillation therapy and/or cardioversion therapy via electrodes located on at least one of the leads 18, 20, 22. Further, the IMD 16 may detect arrhythmia of the heart 12, such as fibrillation of the ventricles 28, 32, and deliver defibrillation therapy to the heart 12 in the form of electrical pulses. In some examples, IMD 16 may be programmed to deliver a progression of therapies, e.g., pulses with increasing energy levels, until a fibrillation of heart 12 is stopped.

Figure 10B:
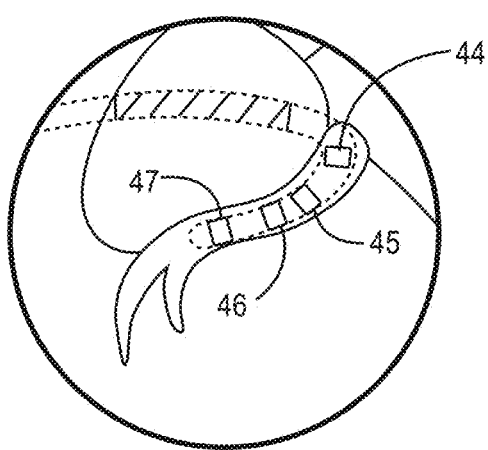
FIG. 10B is a diagram of an enlarged view of a distal end of the electrical lead disposed in the left ventricle of FIG. 16A.

FIG. 10A-10B are conceptual diagrams illustrating the IMD 16 and the leads 18, 20, 22 of therapy system 10 of FIG. 9 in more detail. The leads 18, 20, 22 may be electrically coupled to a therapy delivery module (e.g., for delivery of pacing therapy), a sensing module (e.g., for sensing one or more signals from one or more electrodes), and/or any other modules of the IMD 16 via a connector block 34. In some examples, the proximal ends of the leads 18, 20, 22 may include electrical contacts that electrically couple to respective electrical contacts within the connector block 34 of the IMD 16. In addition, in some examples, the leads 18, 20, 22 may be mechanically coupled to the connector block 34 with the aid of set screws, connection pins, or another suitable mechanical coupling mechanism.

Each of the leads 18, 20, 22 includes an elongated insulative lead body, which may carry a number of conductors (e.g., concentric coiled conductors, straight conductors, etc.) separated from one another by insulation (e.g., tubular insulative sheaths). In the illustrated example, bipolar electrodes 40, 42 are located proximate to a distal end of the lead 18. In addition, the bipolar electrodes 44, 45, 46, 47 are located proximate to a distal end of the lead 20 and the bipolar electrodes 48, 50 are located proximate to a distal end of the lead 22.

The electrodes 40, 44, 44, 45, 46, 47, 48 may take the form of ring electrodes, and the electrodes 42, 50 may take the form of extendable helix tip electrodes mounted retractably within the insulative electrode heads 52, 54, 56, respectively. Each of the electrodes 40, 42, 44, 45, 46, 47, 48, 50 may be electrically coupled to a respective one of the conductors (e.g., coiled and/or straight) within the lead body of its associated lead 18, 20, 22, and thereby coupled to respective ones of the electrical contacts on the proximal end of the leads 18, 20, 22.

Additionally, electrodes 44, 45, 46 and 47 may have an electrode surface area of about 5.3 mm$^2$ to about 5.8 mm$^2$. Electrodes 44, 45, 46, and 47 may also be referred to as LV1, LV2, LV3, and LV4, respectively. The LV electrodes (i.e., left ventricle electrode 1 (LV1) 44, left ventricle electrode 2 (LV2) 45, left ventricle electrode 3 (LV3) 46, and left ventricle 4 (LV4) 47 etc.) on the lead 20 can be spaced apart at variable distances. For example, electrode 44 may be a distance of, e.g., about 21 millimeters (mm), away from electrode 45, electrodes 45 and 46 may be spaced a distance of, e.g. about 1.3 mm to about 1.5 mm, away from each other, and electrodes 46 and 47 may be spaced a distance of, e.g. 20 mm to about 21 mm, away from each other.

The electrodes 40, 42, 44, 45, 46, 47, 48, 50 may further be used to sense electrical signals (e.g., morphological waveforms within electrograms (EGM)) attendant to the depolarization and repolarization of the heart 12. The sensed electrical signals may be used to determine which of the electrodes 40, 42, 44, 45, 46, 47, 48, 50 are the most effective in improving cardiac function. The electrical signals are conducted to the IMD 16 via the respective leads 18, 20, 22. In some examples, the IMD 16 may also deliver pacing pulses via the electrodes 40, 42, 44, 45, 46, 47, 48, 50 to cause depolarization of cardiac tissue of the patient's heart 12. In some examples, as illustrated in FIG. 10A, the IMD 16 includes one or more housing electrodes, such as housing electrode 58, which may be formed integrally with an outer surface of a housing 60 (e.g., hermetically-sealed housing) of the IMD 16 or otherwise coupled to the housing 60. Any of the electrodes 40, 42, 44, 45, 46, 47, 48 and 50 may be used for unipolar sensing or pacing in combination with housing electrode 58. In other words, any of electrodes 40, 42, 44, 45, 46, 47, 48, 50, 58 may be used in combination to form a sensing vector, e.g., a sensing vector that may be used to evaluate and/or analyze the effectiveness of pacing therapy. It is generally understood by those skilled in the art that other electrodes can also be selected to define, or be used for, pacing and sensing vectors. Further, any of electrodes 40, 42, 44, 45, 46, 47, 48, 50, 58, which are not being used to deliver pacing therapy, may be used to sense electrical activity during pacing therapy.

As described in further detail with reference to FIG. 10A, the housing 60 may enclose a therapy delivery module that may include a stimulation generator for generating cardiac pacing pulses and defibrillation or cardioversion shocks, as well as a sensing module for monitoring the patient's heart rhythm. The leads 18, 20, 22 may also include elongated electrodes 62, 64, 66, respectively, which may take the form of a coil. The IMD 16 may deliver defibrillation shocks to the heart 12 via any combination of the elongated electrodes 62, 64, 66 and the housing electrode 58. The electrodes 58, 62, 64, 66 may also be used to deliver cardioversion pulses to the heart 12. Further, the electrodes 62, 64, 66 may be fabricated from any suitable electrically conductive material, such as, but not limited to, platinum, platinum alloy, and/or other materials known to be usable in implantable defibrillation electrodes. Since electrodes 62, 64, 66 are not generally configured to deliver pacing therapy, any of electrodes 62, 64, 66 may be used to sense electrical activity (e.g., for use in determining electrode effectiveness, for use in analyzing pacing therapy effectiveness, etc.) and may be used in combination with any of electrodes 40, 42, 44, 45, 46, 47, 48, 50, 58. In at least one embodiment, the RV elongated electrode 62 may be used to sense electrical activity of a patient's heart during the delivery of pacing therapy (e.g., in combination with the housing electrode 58 forming a RV elongated coil, or defibrillation electrode-to-housing electrode vector).

The configuration of the exemplary therapy system 10 illustrated in FIGS. 9-11 is merely one example. In other examples, the therapy system may include epicardial leads and/or patch electrodes instead of or in addition to the transvenous leads 18, 20, 22 illustrated in FIG. 9. Further, in one or more embodiments, the IMD 16 need not be implanted within the patient 14. For example, the IMD 16 may deliver various cardiac therapies to the heart 12 via percutaneous leads that extend through the skin of the patient 14 to a variety of positions within or outside of the heart 12. In one or more embodiments, the system 10 may utilize wireless pacing (e.g., using energy transmission to the intracardiac pacing component(s) via ultrasound, inductive coupling, RF, etc.) and sensing cardiac activation using electrodes on the can/housing and/or on subcutaneous leads.

In other examples of therapy systems that provide electrical stimulation therapy to the heart 12, such therapy systems may include any suitable number of leads coupled to the IMD 16, and each of the leads may extend to any location within or proximate to the heart 12. For example, other examples of therapy systems may include three transvenous leads located as illustrated in FIGS. 9-11. Still further, other therapy systems may include a single lead that extends from the IMD 16 into the right atrium 26 or the right ventricle 28, or two leads that extend into a respective one of the right atrium 26 and the right ventricle 28.

Figure 11A:
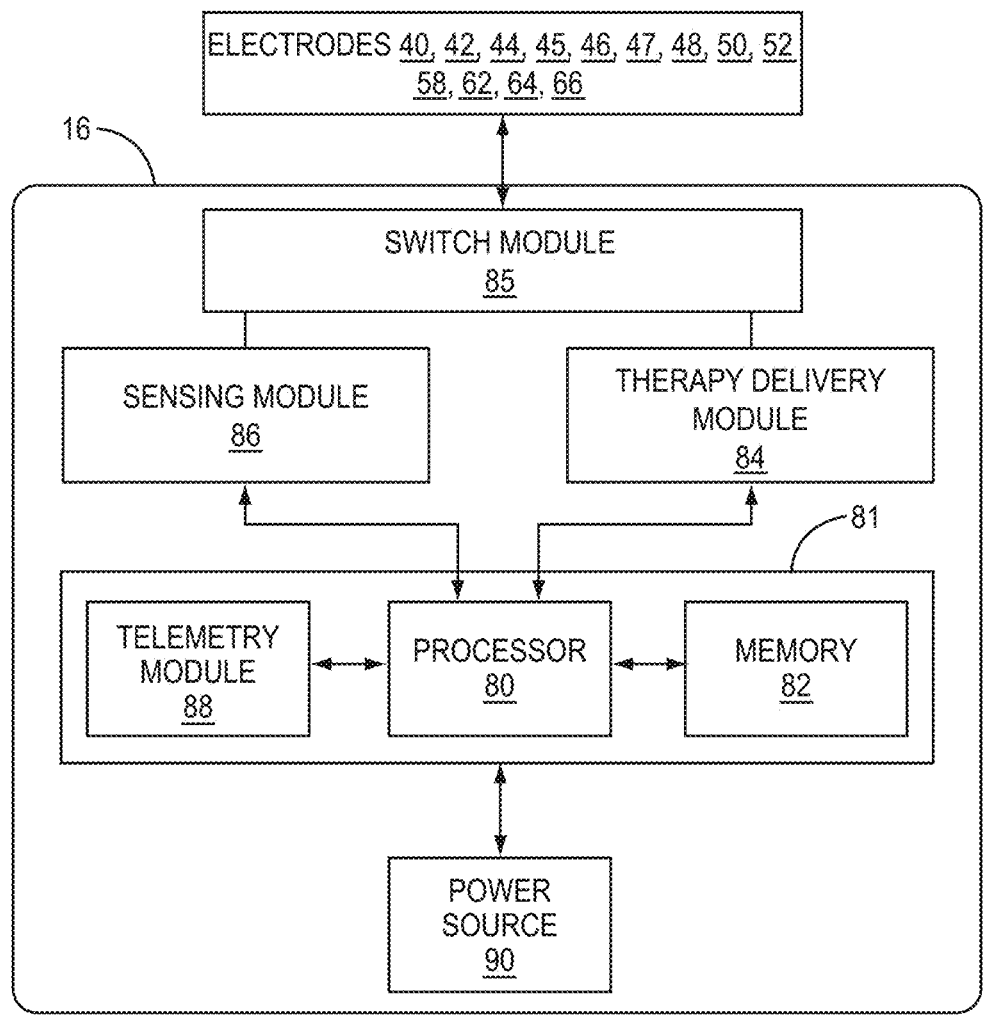
FIG. 11A is a block diagram of an exemplary IMD, e.g., the IMD of FIGS. 9-10.

FIG. 11A is a functional block diagram of one exemplary configuration of the IMD 16. As shown, the IMD 16 may include a control module 81, a therapy delivery module 84 (e.g., which may include a stimulation generator), a sensing module 86, and a power source 90.

The control module 81 may include a processor 80, memory 82, and a telemetry module 88. The memory 82 may include computer-readable instructions that, when executed, e.g., by the processor 80, cause the IMD 16 and/or the control module 81 to perform various functions attributed to the IMD 16 and/or the control module 81 described herein. Further, the memory 82 may include any volatile, non-volatile, magnetic, optical, and/or electrical media, such as a random access memory (RAM), read-only memory (ROM), non-volatile RAM (NVRAM), electrically-erasable programmable ROM (EEPROM), flash memory, and/or any other digital media. An exemplary capture management module may be the left ventricular capture management (LVCM) module described in U.S. Pat. No. 7,684,863 entitled "LV THRESHOLD MEASUREMENT AND CAPTURE MANAGEMENT" and issued Mar. 23, 2010, which is incorporated herein by reference in its entirety.

The processor 80 of the control module 81 may include any one or more of a microprocessor, a controller, a digital signal processor (DSP), an application specific integrated circuit (ASIC), a field-programmable gate array (FPGA), and/or equivalent discrete or integrated logic circuitry. In some examples, the processor 80 may include multiple components, such as any combination of one or more microprocessors, one or more controllers, one or more DSPs, one or more ASICs, and/or one or more FPGAs, as well as other discrete or integrated logic circuitry. The functions attributed to the processor 80 herein may be embodied as software, firmware, hardware, or any combination thereof.

The control module 81 may be used to determine the effectiveness of the electrodes 40, 42, 44, 45, 46, 47, 48, 50, 58, 62, 64, 66 using the exemplary methods and/or processes described herein according to a selected one or more programs, which may be stored in the memory 82. Further, the control module 81 may control the therapy delivery module 84 to deliver therapy (e.g., electrical stimulation therapy such as pacing) to the heart 12 according to a selected one or more therapy programs, which may be stored in the memory 82. More, specifically, the control module 81 (e.g., the processor 80) may control various parameters of the electrical stimulus delivered by the therapy delivery module 84 such as, e.g., AV delays, pacing pulses with the amplitudes, pulse widths, frequency, or electrode polarities, etc., which may be specified by one or more selected therapy programs (e.g., AV delay adjustment programs, pacing therapy programs, pacing recovery programs, capture management programs, etc.). As shown, the therapy delivery module 84 is electrically coupled to electrodes 40, 42, 44, 45, 46, 47, 48, 50, 58, 62, 64, 66, e.g., via conductors of the respective lead 18, 20, 22, or, in the case of housing electrode 58, via an electrical conductor disposed within housing 60 of IMD 16. Therapy delivery module 84 may be configured to generate and deliver electrical stimulation therapy such as pacing therapy to the heart 12 using one or more of the electrodes 40, 42, 44, 45, 46, 47, 48, 50, 58, 62, 64, 66.

For example, therapy delivery module 84 may deliver pacing stimulus (e.g., pacing pulses) via ring electrodes 40, 44, 45, 46, 47, 48 coupled to leads 18, 20, and 22, respectively, and/or helical tip electrodes 42 and 50 of leads 18 and 22. Further, for example, therapy delivery module 84 may deliver defibrillation shocks to heart 12 via at least two of electrodes 58, 62, 64, 66. In some examples, therapy delivery module 84 may be configured to deliver pacing, cardioversion, or defibrillation stimulation in the form of electrical pulses. In other examples, therapy delivery module 84 may be configured deliver one or more of these types of stimulation in the form of other signals, such as sine waves, square waves, and/or other substantially continuous time signals.

The IMD 16 may further include a switch module 85 and the control module 81 (e.g., the processor 80) may use the switch module 85 to select, e.g., via a data/address bus, which of the available electrodes are used to deliver therapy such as pacing pulses for pacing therapy, or which of the available electrodes are used for sensing. The switch module 85 may include a switch array, switch matrix, multiplexer, or any other type of switching device suitable to selectively couple the sensing module 86 and/or the therapy delivery module 84 to one or more selected electrodes. More specifically, the therapy delivery module 84 may include a plurality of pacing output circuits. Each pacing output circuit of the plurality of pacing output circuits may be selectively coupled, e.g., using the switch module 85, to one or more of the electrodes 40, 42, 44, 45, 46, 47, 48, 50, 58, 62, 64, 66 (e.g., a pair of electrodes for delivery of therapy to a pacing vector). In other words, each electrode can be selectively coupled to one of the pacing output circuits of the therapy delivery module using the switching module 85.

The sensing module 86 is coupled (e.g., electrically coupled) to sensing apparatus, which may include, among additional sensing apparatus, the electrodes 40, 42, 44, 45, 46, 47, 48, 50, 58, 62, 64, 66 to monitor electrical activity of the heart 12, e.g., electrocardiogram (ECG)/electrogram (EGM) signals, etc. The ECG/EGM signals may be used to measure or monitor activation times (e.g., ventricular activations times, etc.), heart rate (HR), heart rate variability (HRV), heart rate turbulence (HRT), deceleration/acceleration capacity, deceleration sequence incidence, T-wave alternans (TWA), P-wave to P-wave intervals (also referred to as the P-P intervals or A-A intervals), R-wave to R-wave intervals (also referred to as the R-R intervals or V-V intervals), P-wave to QRS complex intervals (also referred to as the P-R intervals, A-V intervals, or P-Q intervals), QRS-complex morphology, ST segment (i.e., the segment that connects the QRS complex and the T-wave), T-wave changes, QT intervals, electrical vectors, etc.

The switch module 85 may be also be used with the sensing module 86 to select which of the available electrodes are used, or enabled, to, e.g., sense electrical activity of the patient's heart (e.g., one or more electrical vectors of the patient's heart using any combination of the electrodes 40, 42, 44, 45, 46, 47, 48, 50, 58, 62, 64, 66). Likewise, the switch module 85 may be also be used with the sensing module 86 to select which of the available electrodes are not to be used (e.g., disabled) to, e.g., sense electrical activity of the patient's heart (e.g., one or more electrical vectors of the patient's heart using any combination of the electrodes 40, 42, 44, 45, 46, 47, 48, 50, 58, 62, 64, 66), etc. In some examples, the control module 81 may select the electrodes that function as sensing electrodes via the switch module within the sensing module 86, e.g., by providing signals via a data/address bus.

In some examples, sensing module 86 includes a channel that includes an amplifier with a relatively wider pass band than the R-wave or P-wave amplifiers. Signals from the selected sensing electrodes may be provided to a multiplexer, and thereafter converted to multi-bit digital signals by an analog-to-digital converter for storage in memory 82, e.g., as an electrogram (EGM). In some examples, the storage of such EGMs in memory 82 may be under the control of a direct memory access circuit.

In some examples, the control module 81 may operate as an interrupt driven device, and may be responsive to interrupts from pacer timing and control module, where the interrupts may correspond to the occurrences of sensed P-waves and R-waves and the generation of cardiac pacing pulses. Any necessary mathematical calculations may be performed by the processor 80 and any updating of the values or intervals controlled by the pacer timing and control module may take place following such interrupts. A portion of memory 82 may be configured as a plurality of recirculating buffers, capable of holding one or more series of measured intervals, which may be analyzed by, e.g., the processor 80 in response to the occurrence of a pace or sense interrupt to determine whether the patient's heart 12 is presently exhibiting atrial or ventricular tachyarrhythmia.

The telemetry module 88 of the control module 81 may include any suitable hardware, firmware, software, or any combination thereof for communicating with another device, such as a programmer. For example, under the control of the processor 80, the telemetry module 88 may receive downlink telemetry from and send uplink telemetry to a programmer with the aid of an antenna, which may be internal and/or external. The processor 80 may provide the data to be uplinked to a programmer and the control signals for the telemetry circuit within the telemetry module 88, e.g., via an address/data bus. In some examples, the telemetry module 88 may provide received data to the processor 80 via a multiplexer.

The various components of the IMD 16 are further coupled to a power source 90, which may include a rechargeable or non-rechargeable battery. A non-rechargeable battery may be selected to last for several years, while a rechargeable battery may be inductively charged from an external device, e.g., on a daily or weekly basis.

Figure 11B:
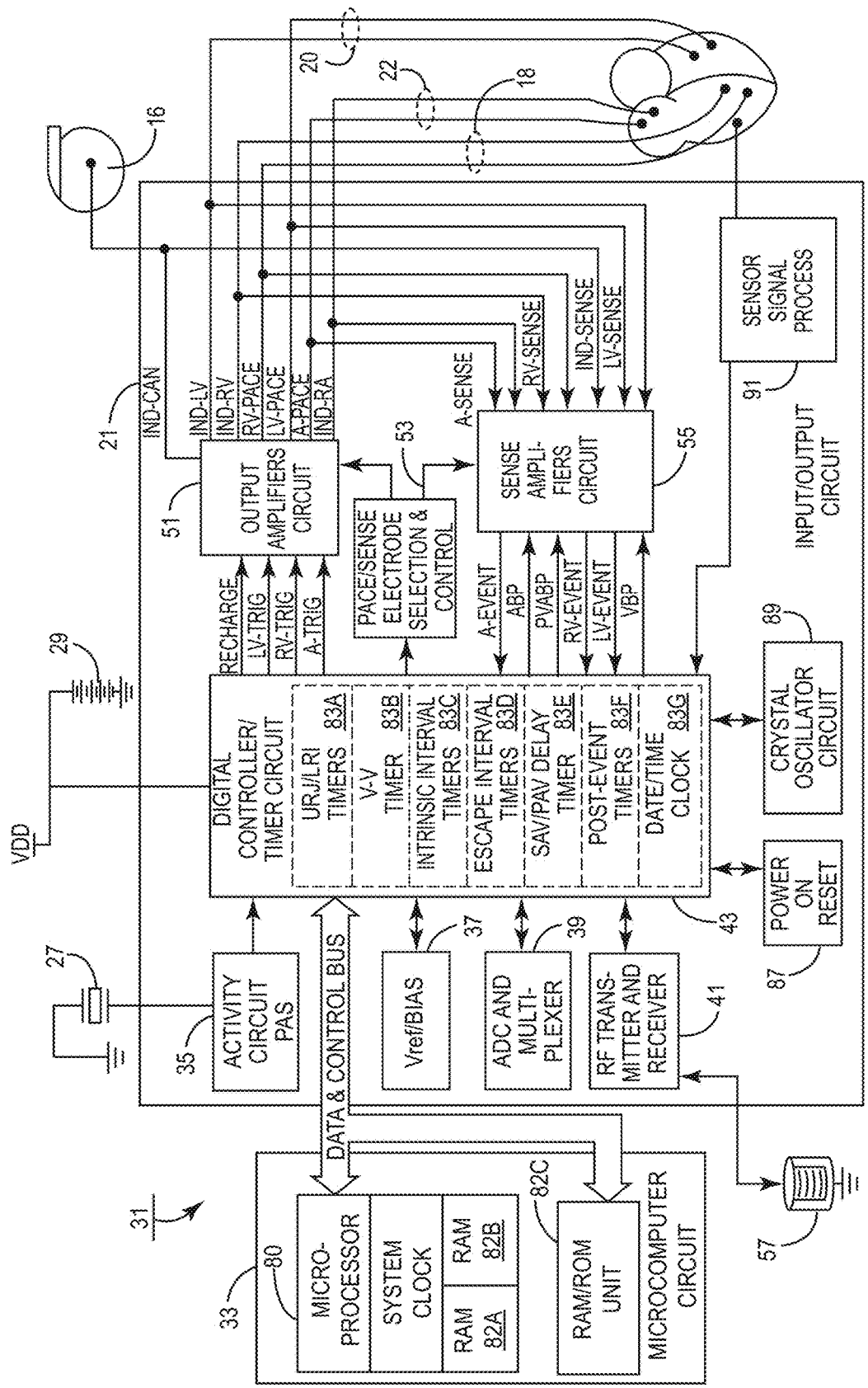
FIG. 11B is another block diagram of an exemplary IMD (e.g., an implantable pulse generator) circuitry and associated leads employed in the system of FIGS. 9-10 for providing three sensing channels and corresponding pacing channels.

FIG. 11B is another embodiment of a functional block diagram for IMD 16. FIG. 11B depicts bipolar RA lead 22, bipolar RV lead 18, and bipolar LV CS lead 20 without the LA CS pace/sense electrodes and coupled with an implantable pulse generator (IPG) circuit 31 having programmable modes and parameters of a biventricular DDD/R type known in the pacing art. In turn, the sensor signal processing circuit 91 indirectly couples to the timing circuit 83 and via data and control bus to microcomputer circuitry 33. The IPG circuit 31 is illustrated in a functional block diagram divided generally into a microcomputer circuit 33 and a pacing circuit 21. The pacing circuit 21 includes the digital controller/timer circuit 83, the output amplifiers circuit 51, the sense amplifiers circuit 55, the RF telemetry transceiver 41, the activity sensor circuit 35 as well as a number of other circuits and components described below.

Crystal oscillator circuit 89 provides the basic timing clock for the pacing circuit 21, while battery 29 provides power. Power-on-reset circuit 87 responds to initial connection of the circuit to the battery for defining an initial operating condition and similarly, resets the operative state of the device in response to detection of a low battery condition. Reference mode circuit 37 generates stable voltage reference and currents for the analog circuits within the pacing circuit 21, while analog to digital converter ADC and multiplexer circuit 39 digitizes analog signals and voltage to provide real time telemetry if cardiac signals from sense amplifiers 55, for uplink transmission via RF transmitter and receiver circuit 41. Voltage reference and bias circuit 37, ADC and multiplexer 39, power-on-reset circuit 87 and crystal oscillator circuit 89 may correspond to any of those presently used in current marketed implantable cardiac pacemakers.

If the IPG is programmed to a rate responsive mode, the signals output by one or more physiologic sensor are employed as a rate control parameter (RCP) to derive a physiologic escape interval. For example, the escape interval is adjusted proportionally to the patient's activity level developed in the patient activity sensor (PAS) circuit 35 in the depicted, exemplary IPG circuit 31. The patient activity sensor 27 is coupled to the IPG housing and may take the form of a piezoelectric crystal transducer as is well known in the art and its output signal is processed and used as the RCP. Sensor 27 generates electrical signals in response to sensed physical activity that are processed by activity circuit 35 and provided to digital controller/timer circuit 83. Activity circuit 35 and associated sensor 27 may correspond to the circuitry disclosed in U.S. Pat. No. 5,052,388 entitled "METHOD AND APPARATUS FOR IMPLEMENTING ACTIVITY SENSING IN A PULSE GENERATOR" and issued on Oct. 1, 1991 and U.S. Pat. No. 4,428,378 entitled "RATE ADAPTIVE PACER" and issued on Jan. 31, 1984, each of which are incorporated herein by reference in their entireties. Similarly, the exemplary systems, apparatus, and methods described herein may be practiced in conjunction with alternate types of sensors such as oxygenation sensors, pressure sensors, pH sensors and respiration sensors, all well known for use in providing rate responsive pacing capabilities. Alternately, QT time may be used as the rate indicating parameter, in which case no extra sensor is required. Similarly, the exemplary embodiments described herein may also be practiced in non-rate responsive pacemakers.

Data transmission to and from the external programmer is accomplished by way of the telemetry antenna 57 and an associated RF transceiver 41, which serves both to demodulate received downlink telemetry and to transmit uplink telemetry. Uplink telemetry capabilities will typically include the ability to transmit stored digital information, e.g. operating modes and parameters, EGM histograms, and other events, as well as real time EGMs of atrial and/or ventricular electrical activity and marker channel pulses indicating the occurrence of sensed and paced depolarizations in the atrium and ventricle, as are well known in the pacing art.

Microcomputer 33 contains a microprocessor 80 and associated system clock and on-processor RAM and ROM chips 82A and 82B, respectively. In addition, microcomputer circuit 33 includes a separate RAM/ROM chip 82C to provide additional memory capacity. Microprocessor 80 normally operates in a reduced power consumption mode and is interrupt driven. Microprocessor 80 is awakened in response to defined interrupt events, which may include A-TRIG, RV-TRIG, LV-TRIG signals generated by timers in digital timer/controller circuit 83 and A-EVENT, RV-EVENT, and LV-EVENT signals generated by sense amplifiers circuit 55, among others. The specific values of the intervals and delays timed out by digital controller/timer circuit 83 are controlled by the microcomputer circuit 33 by way of data and control bus from programmed-in parameter values and operating modes. In addition, if programmed to operate as a rate responsive pacemaker, a timed interrupt, e.g., every cycle or every two seconds, may be provided in order to allow the microprocessor to analyze the activity sensor data and update the basic A-A, V-A, or V-V escape interval, as applicable. In addition, the microprocessor 80 may also serve to define variable, operative AV delay intervals and the energy delivered to each ventricle.

In one embodiment, microprocessor 80 is a custom microprocessor adapted to fetch and execute instructions stored in RAM/ROM unit 82 in a conventional manner. It is contemplated, however, that other implementations may be suitable to practice the present invention. For example, an off-the-shelf, commercially available microprocessor or microcontroller, or custom application-specific, hardwired logic, or state-machine type circuit may perform the functions of microprocessor 80.

Digital controller/timer circuit 83 operates under the general control of the microcomputer 33 to control timing and other functions within the pacing circuit 320 and includes a set of timing and associated logic circuits of which certain ones pertinent to the present invention are depicted. The depicted timing circuits include URI/LRI timers 83A, V-V delay timer 83B, intrinsic interval timers 83C for timing elapsed V-EVENT to V-EVENT intervals or V-EVENT to A-EVENT intervals or the V-V conduction interval, escape interval timers 83D for timing A-A, V-A, and/or V-V pacing escape intervals, an AV delay interval timer 83E for timing the A-LVp delay (or A-RVp delay) from a preceding A-EVENT or A-TRIG, a post-ventricular timer 83F for timing post-ventricular time periods, and a date/time clock 83G.

The AV delay interval timer 83E is loaded with an appropriate delay interval for one ventricular chamber (e.g., either an A-RVp delay or an A-LVp delay as determined using known methods) to time-out starting from a preceding A-PACE or A-EVENT. The interval timer 83E triggers pacing stimulus delivery, and can be based on one or more prior cardiac cycles (or from a data set empirically derived for a given patient).

The post-event timer 83F time out the post-ventricular time period following an RV-EVENT or LV-EVENT or a RV-TRIG or LV-TRIG and post-atrial time periods following an A-EVENT or A-TRIG. The durations of the post-event time periods may also be selected as programmable parameters stored in the microcomputer 33. The post-ventricular time periods include the PVARP, a post-atrial ventricular blanking period (PAVBP), a ventricular blanking period (VBP), a post-ventricular atrial blanking period (PVARP) and a ventricular refractory period (VRP) although other periods can be suitably defined depending, at least in part, on the operative circuitry employed in the pacing engine. The post-atrial time periods include an atrial refractory period (ARP) during which an A-EVENT is ignored for the purpose of resetting any AV delay, and an atrial blanking period (ABP) during which atrial sensing is disabled. It should be noted that the starting of the post-atrial time periods and the AV delays can be commenced substantially simultaneously with the start or end of each A-EVENT or A-TRIG or, in the latter case, upon the end of the A-PACE which may follow the A-TRIG. Similarly, the starting of the post-ventricular time periods and the V-A escape interval can be commenced substantially simultaneously with the start or end of the V-EVENT or V-TRIG or, in the latter case, upon the end of the V-PACE which may follow the V-TRIG. The microprocessor 80 also optionally calculates AV delays, post-ventricular time periods, and post-atrial time periods that vary with the sensor based escape interval established in response to the RCP(s) and/or with the intrinsic atrial rate.

The output amplifiers circuit 51 contains a RA pace pulse generator (and a LA pace pulse generator if LA pacing is provided), a RV pace pulse generator, and a LV pace pulse generator or corresponding to any of those presently employed in commercially marketed cardiac pacemakers providing atrial and ventricular pacing. In order to trigger generation of an RV-PACE or LV-PACE pulse, digital controller/timer circuit 83 generates the RV-TRIG signal at the time-out of the A-RVp delay (in the case of RV pre-excitation) or the LV-TRIG at the time-out of the A-LVp delay (in the case of LV pre-excitation) provided by AV delay interval timer 83E (or the V-V delay timer 83B). Similarly, digital controller/timer circuit 83 generates an RA-TRIG signal that triggers output of an RA-PACE pulse (or an LA-TRIG signal that triggers output of an LA-PACE pulse, if provided) at the end of the V-A escape interval timed by escape interval timers 83D.

The output amplifiers circuit 51 includes switching circuits for coupling selected pace electrode pairs from among the lead conductors and the IND_CAN electrode 20 to the RA pace pulse generator (and LA pace pulse generator if provided), RV pace pulse generator and LV pace pulse generator. Pace/sense electrode pair selection and control circuit 53 selects lead conductors and associated pace electrode pairs to be coupled with the atrial and ventricular output amplifiers within output amplifiers circuit 51 for accomplishing RA, LA, RV and LV pacing.

The sense amplifiers circuit 55 contains sense amplifiers corresponding to any of those presently employed in contemporary cardiac pacemakers for atrial and ventricular pacing and sensing. High impedance P-wave and R-wave sense amplifiers may be used to amplify a voltage difference signal that is generated across the sense electrode pairs by the passage of cardiac depolarization wavefronts. The high impedance sense amplifiers use high gain to amplify the low amplitude signals and rely on pass band filters, time domain filtering and amplitude threshold comparison to discriminate a P-wave or R-wave from background electrical noise. Digital controller/timer circuit 83 controls sensitivity settings of the atrial and ventricular sense amplifiers 55.

The sense amplifiers are typically uncoupled from the sense electrodes during the blanking periods before, during, and after delivery of a pace pulse to any of the pace electrodes of the pacing system to avoid saturation of the sense amplifiers. The sense amplifiers circuit 55 includes blanking circuits for uncoupling the selected pairs of the lead conductors and the IND-CAN electrode 20 from the inputs of the RA sense amplifier (and LA sense amplifier if provided), RV sense amplifier and LV sense amplifier during the ABP, PVABP and VBP. The sense amplifiers circuit 55 also includes switching circuits for coupling selected sense electrode lead conductors and the IND-CAN electrode 20 to the RA sense amplifier (and LA sense amplifier if provided), RV sense amplifier and LV sense amplifier. Again, sense electrode selection and control circuit 53 selects conductors and associated sense electrode pairs to be coupled with the atrial and ventricular sense amplifiers within the output amplifiers circuit 51 and sense amplifiers circuit 55 for accomplishing RA, LA, RV and LV sensing along desired unipolar and bipolar sensing vectors.

Right atrial depolarizations or P-waves in the RA-SENSE signal that are sensed by the RA sense amplifier result in a RA-EVENT signal that is communicated to the digital controller/timer circuit 83. Similarly, left atrial depolarizations or P-waves in the LA-SENSE signal that are sensed by the LA sense amplifier, if provided, result in a LA-EVENT signal that is communicated to the digital controller/timer circuit 83. Ventricular depolarizations or R-waves in the RV-SENSE signal are sensed by a ventricular sense amplifier result in an RV-EVENT signal that is communicated to the digital controller/timer circuit 83. Similarly, ventricular depolarizations or R-waves in the LV-SENSE signal are sensed by a ventricular sense amplifier result in an LV-EVENT signal that is communicated to the digital controller/timer circuit 83. The RV-EVENT, LV-EVENT, and RA-EVENT, LA-SENSE signals may be refractory or non-refractory, and can inadvertently be triggered by electrical noise signals or aberrantly conducted depolarization waves rather than true R-waves or P-waves.

The techniques described in this disclosure, including those attributed to the IMD 16, the computing apparatus 140, and/or various constituent components, may be implemented, at least in part, in hardware, software, firmware, or any combination thereof. For example, various aspects of the techniques may be implemented within one or more processors, including one or more microprocessors, DSPs, ASICs, FPGAs, or any other equivalent integrated or discrete logic circuitry, as well as any combinations of such components, embodied in programmers, such as physician or patient programmers, stimulators, image processing devices, or other devices. The term "module," "processor," or "processing circuitry" may generally refer to any of the foregoing logic circuitry, alone or in combination with other logic circuitry, or any other equivalent circuitry.

Such hardware, software, and/or firmware may be implemented within the same device or within separate devices to support the various operations and functions described in this disclosure. In addition, any of the described units, modules, or components may be implemented together or separately as discrete but interoperable logic devices. Depiction of different features as modules or units is intended to highlight different functional aspects and does not necessarily imply that such modules or units must be realized by separate hardware or software components. Rather, functionality associated with one or more modules or units may be performed by separate hardware or software components, or integrated within common or separate hardware or software components.

When implemented in software, the functionality ascribed to the systems, devices and techniques described in this disclosure may be embodied as instructions on a computer-readable medium such as RAM, ROM, NVRAM, EEPROM, FLASH memory, magnetic data storage media, optical data storage media, or the like. The instructions may be executed by one or more processors to support one or more aspects of the functionality described in this disclosure.

As indicated above, to facilitate evaluating the whether a patient is a candidate for CRT based on the monitored output, the one or more indications of cardiac electrical dyssynchrony, e.g., indices or graphical indications, may be determined based on torso-surface activation times during both intrinsic conduction of the heart, and during CRT. Differences between the indications during intrinsic conduction and CRT may indicate that CRT would provide benefit for the patient, e.g., that the patient is a candidate for CRT. Furthermore, during noninvasive evaluation to determine whether a patient is a CRT candidate, implantation or a follow-up visit, the one or more indications of cardiac electrical dyssynchrony may be determined for each of a plurality of lead positions, electrode configurations, or other parameter values based on torso-surface activation times resulting from delivery of CRT at the positions, or with the electrode configurations or parameter values. In this manner, differences between cardiac electrical dyssynchrony indications associated with various locations, electrode configurations, or parameter values may be compared to determine preferred locations, configurations, or values.

Figure 12:
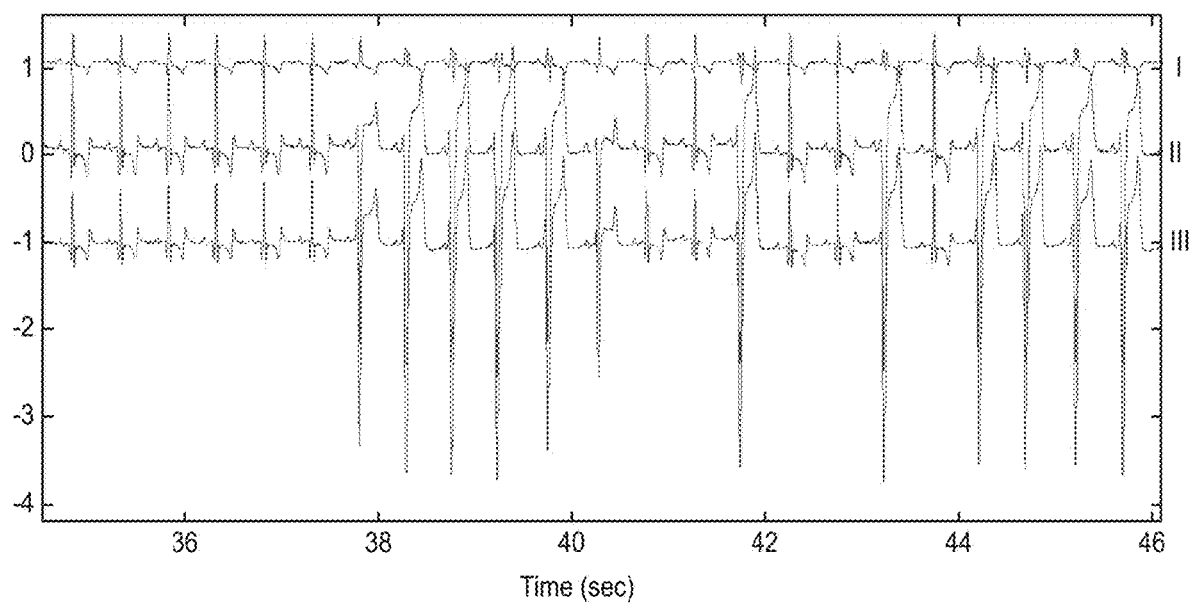
FIG. 12 depicts a mixture of intrinsic complexes and monomorphic paced complexes in response to delivery of ultrasound paces.
Figure 13:
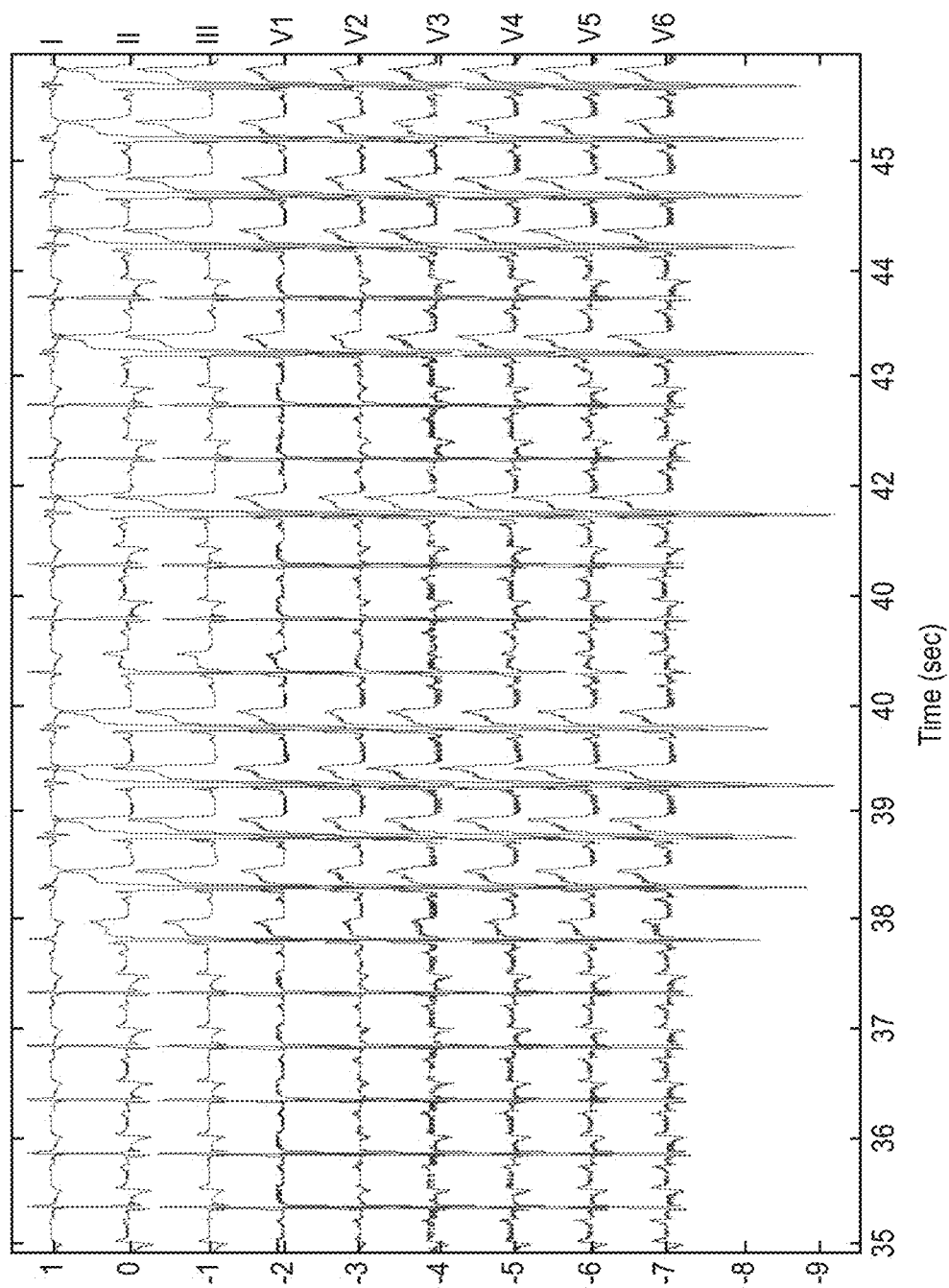
FIG. 13 depicts another mixture of intrinsic complexes and monomorphic paced complexes in response to delivery of ultrasound paces.
Figure 14:
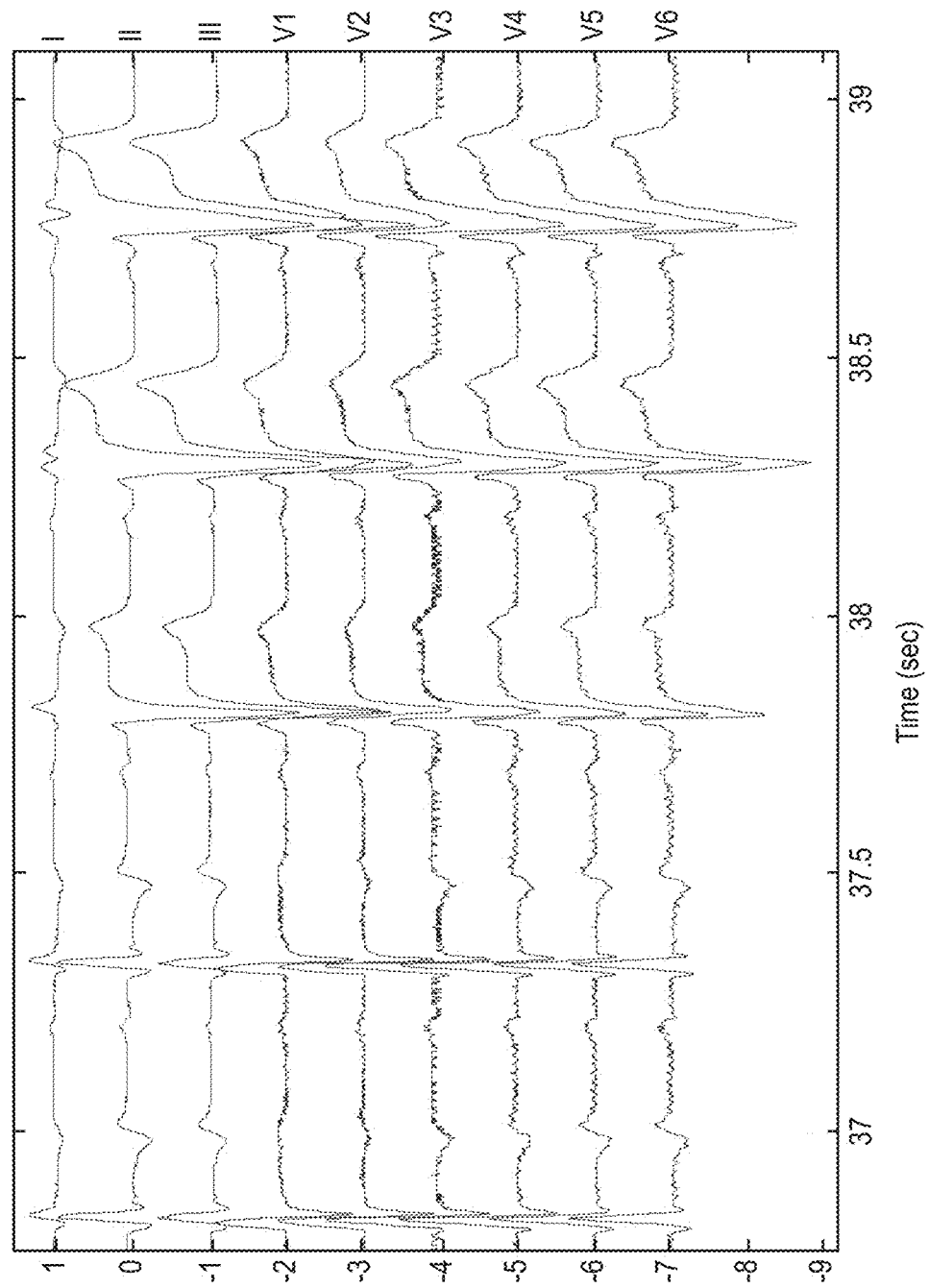
FIG. 14 depicts another mixture of intrinsic complexes and monomorphic paced complexes in response to delivery of ultrasound paces.

A set of experiments established that triggered noninvasive pacing can be accomplished with ultrasound applied on or close to the skin. When combined with a system to assess electrical heterogeneity, such ultrasound paces could be used to determine whether a patient would benefit from CRT. Performing noninvasive assessments helps reduce costs to the health care system. FIGS. 12-14 are associated with the first experiment while FIGS. 15-21 are related to the second experiment.

Figure 15:
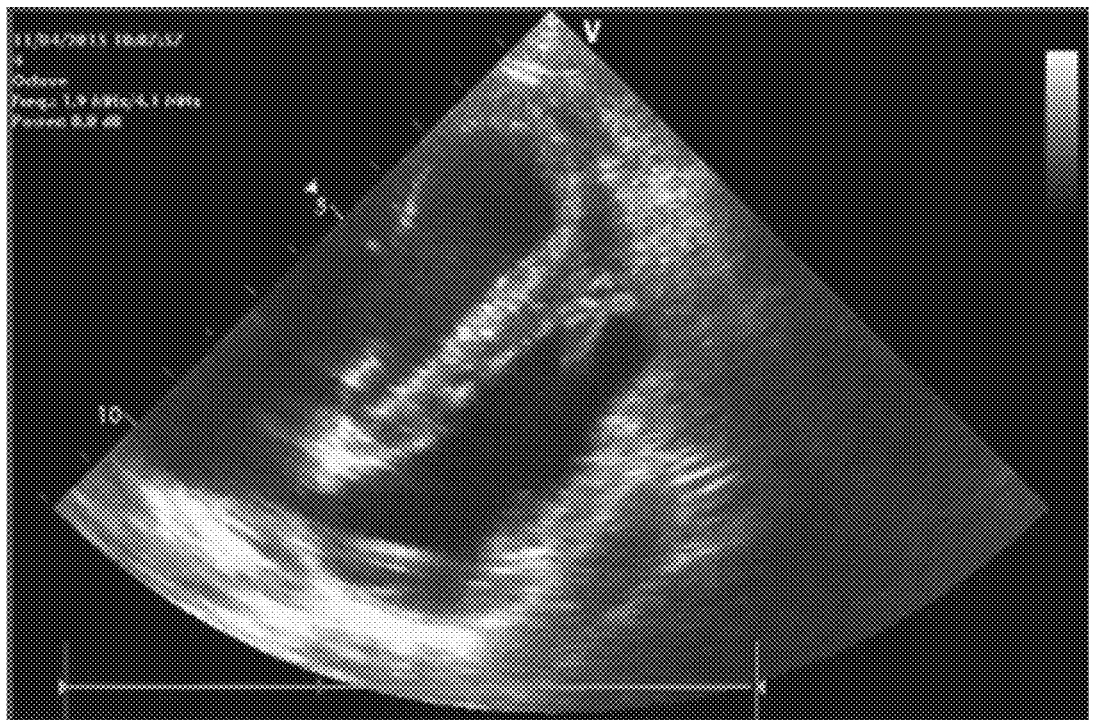
FIG. 15 depicts an image of a canine heart with markers on the left side of the heart.

In the first canine experiment that was performed on a closed chest, a 200 kHz transducer was placed on the skin over the apex. A 2-D ultrasound image shown in FIG. 15 depicts an apex of heart (i.e. near the top of the image) while the ventricular septum is generally located in the middle of the image with the LV to the left and RV to the right. The same acoustic window was used for both experiments. The depth markers (in cm) are depicted on the left side of the image. A variety of transducers with a variety of frequencies and/or variety of probe diameters were employed to test delivery of the ultrasound pace through the skin to the cardiac tissue. A piston transducer was used in the first experiment; however, skilled artisans understand that a variety of other transducers can be used. For example, a transducer phased array which is a lot of small transducers can also be used.

The timing of the delivery of the pace is based off of the atrium (i.e. detection of the P-wave signal or pulse). When the atrium is activated or fires, a delay is added. The delay can be swept over a range of values, like 50 ms to 200 ms, to achieve different degrees of fusion between the left ventricular pace and the intrinsic activation of the ventricles. After the delay expired, the ultrasound pace was delivered to the cardiac tissue (e.g. ventricle). After the ultrasound pace is delivered, a determination is made as to whether capture of the cardiac tissue has occurred. Stimuli (e.g. ultrasound paces) that cause the ventricle to respond are commonly referred to as capturing cardiac tissue.

Contrast (e.g. LUMASON™ commercially available from Bracco Diagnostics located in Milan, Italy, or microbubbles) was injected intravenously to enhance mechanical stimulation of the heart in response to ultrasound. LUMASON™ is an ultrasound contrast agent used in patients to opacify the left ventricular chamber and to improve the delineation of the left ventricular endocardial border. In this experiment, contrast was injected 4 minutes and 33 seconds before the time reference of zero (not shown). A transducer produced 700 KPa pressure, 50 ms pulse width, at a frequency of 200 kHz. The transducer was triggered at 20 ms after sensing the P-wave (via Medtronic 5076 lead located in the right atrium (RA)). FIGS. 12-14 show intermittent pacing was achieved, depending on minor movements of the transducer and motion due to breathing. FIG. 12 depicts the cardiac response to delivery of an ultrasound pace (i.e. HIFU pace). The X-axis is the time in seconds while the Y-axis is in millivolts for each ECG vector of three ECG vectors (designated as I, II, and III) on the skin of the canine. The paced complexes are monomorphic which indicates that a consistent location of activation is occurring in response to the HIFU paces.

FIG. 13 depicts the cardiac response to delivery of an ultrasound pace such as a HIFU pace. Leads were applied to the skin in order to determine where pacing is occurring (i.e. which part of the heart is starting to pace). The X-axis is the time in seconds while the Y-axis is in millivolts for each vector of the nine lead ECG (designated as I, II, III, V1-V6) on the skin of the canine. FIG. 14 is an enlarged portion of FIG. 13.

Figure 16:
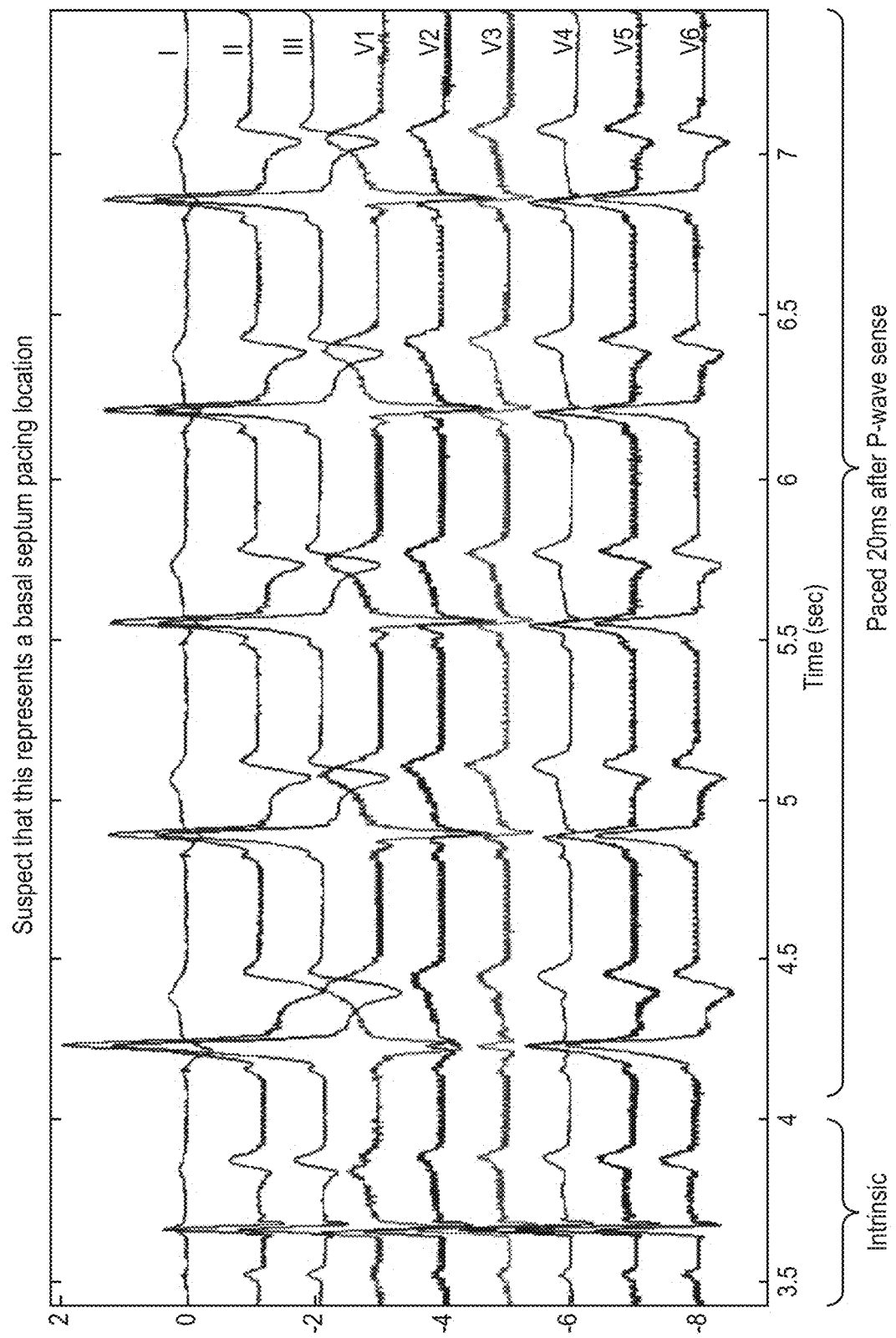
FIG. 16 depicts a single intrinsic beat followed by consistent pacing at a basal septum pacing location, in which the transducer uses a frequency of 200 KHz, and pulse width of 1 ms.

FIGS. 16-21 relate to a second experiment which confirms the results from the first experiment. Three different ultrasound frequencies and two different transducer probe diameters were employed. FIG. 16 shows consistent pacing was achieved at a basal septum pacing location using a frequency of 200 KHz, and 1 ms pulse widths. In the second experiment, contrast was continuously delivered instead of the delivery of a single bolus of contrast as was done in the first experiment. It is believed that the ECG results shown in FIG. 16 represent a basal septum pacing location. The ECG vectors and V1-V6 are from electrodes placed directly on the skin of the canine. The intrinsic rhythm is shown as having occurred between about 3.5 and 4 seconds. The ultrasound pace was delivered 20 ms after the P-wave was detected or sensed. As is shown in the plot, consistent pacing occurred at the basal septum location.

Figure 17C:
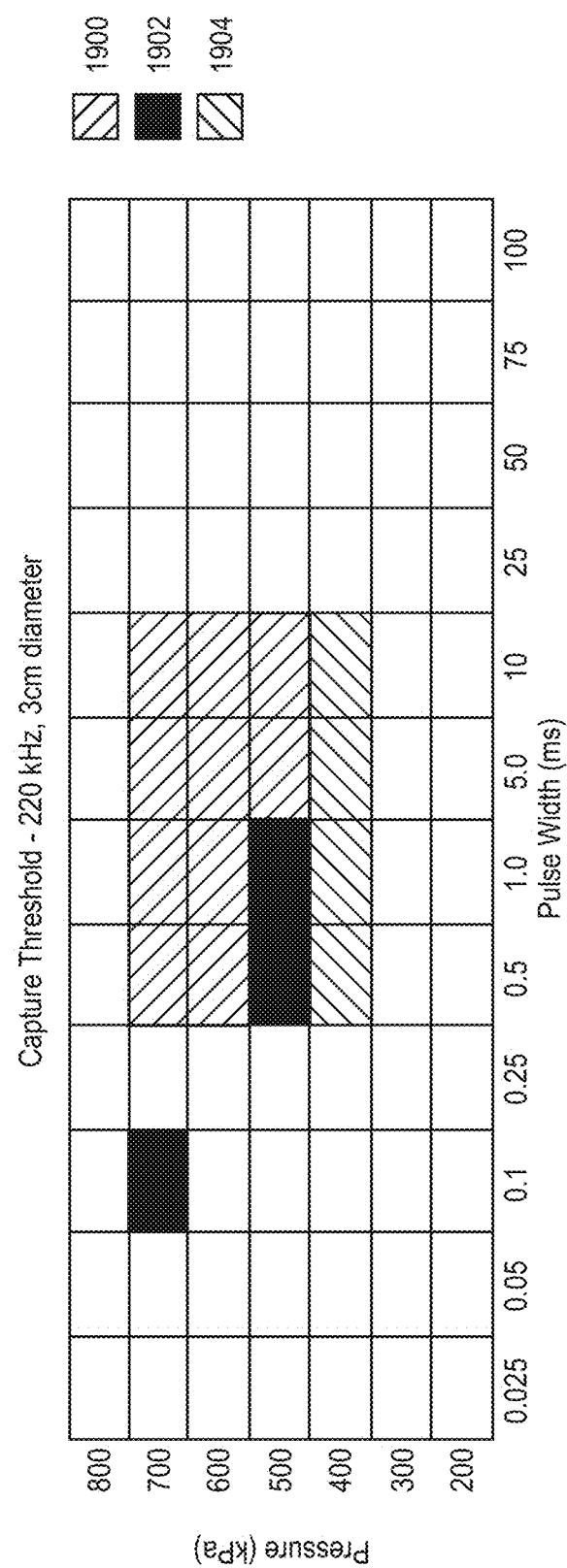
FIG. 17C depicts a strength-duration curve, showing cardiac capture occurring at various ultrasound amplitudes and pulse widths in response to stimuli being delivered by an ultrasound transducer probe having a diameter of 3 cm and a frequency of 220 kHz.
Figure 18A:
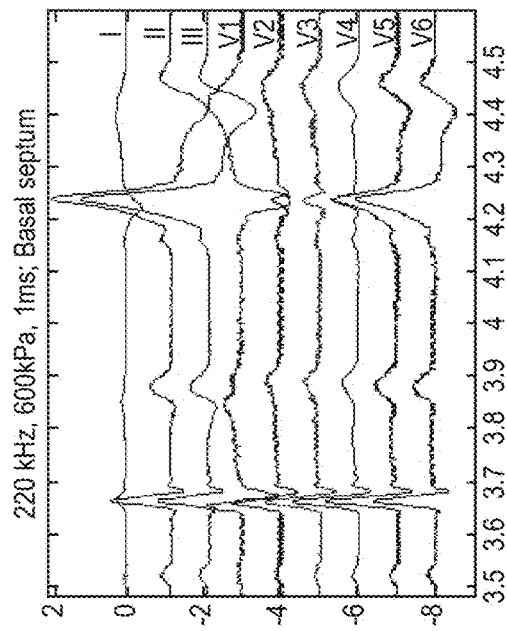
FIG. 18A depicts one intrinsic beat followed by capture occurring at the Apex in response to an ultrasound stimuli being delivered.
Figure 18C:
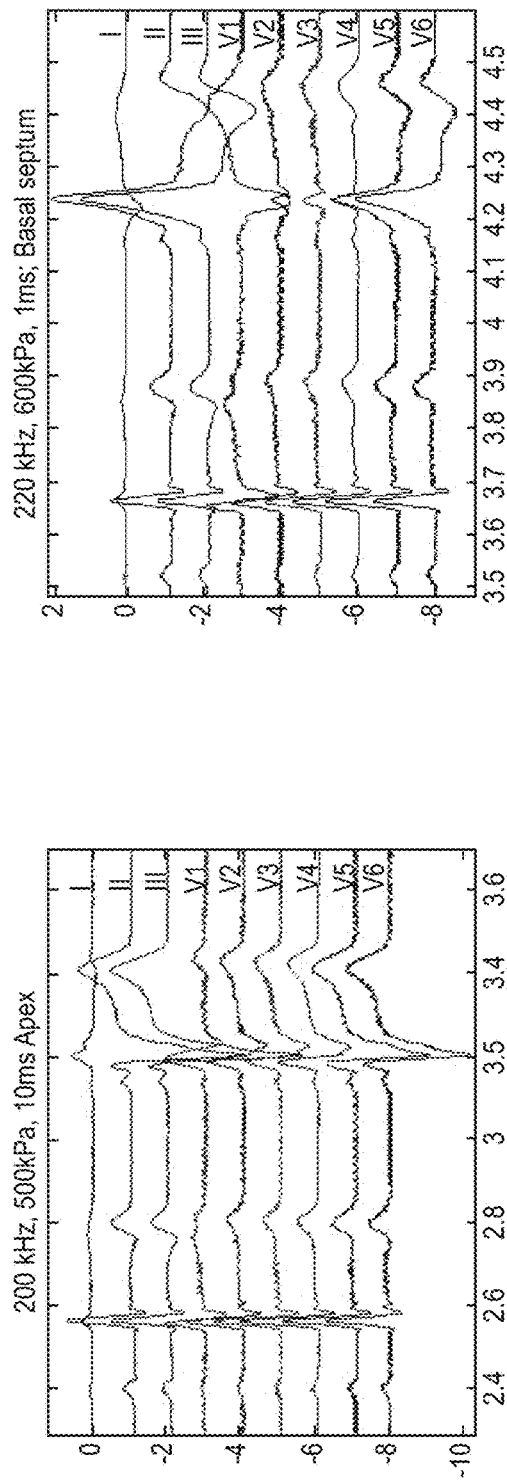
FIG. 18C depicts one intrinsic beat followed by capture occurring at an area believed to be the basal septum in response to an ultrasound stimuli being delivered.
Figure 18B:
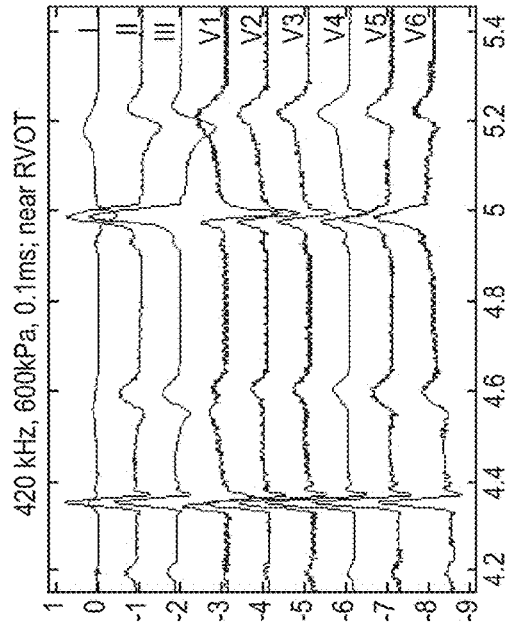
FIG. 18B depicts one intrinsic beat followed by capture occurring in response to an ultrasound stimuli being delivered.

FIGS. 17A-17C show capture occurred at varying frequencies (i.e. 200 kHz, 420 KHz and 220 kHz.) and probe diameters (e.g. 3 cm, 5 cm). FIGS. 17A-17C depict the pulse width (ms) along the X-axis and the pressure (KPa) along the Y-axis. A 200 KHz and 5 cm transducer was employed for the data represented in FIG. 17A. For example, a transducer using a frequency of 200 KHz and a 5 cm diameter was employed. Capture occurred at boxes 1900 whereas capture rarely occurred at boxes 1902. No capture occurred at boxes 1904 of FIG. 17A. Effective capture generally occurred at ultrasound pressures above 400 KPa. No effective capture occurred at or below 300 KPa. Exemplary methods for determining effective capture is shown and described in U.S. Pat. No. 8,750,998 issued Jun. 10, 2014, and assigned to the assignee of the present invention, the disclosure of which is incorporated by reference in its entirety herein. The term "effective capture test," employs elements parsed from a signal sensed from the ventricle. A sensed signal from a ventricle includes a maximum amplitude (Max), a maximum time (Tmax) associated with the maximum amplitude (Max), a minimum amplitude (Min), and a minimum time (Tmin) associated with the minimum amplitude. The effective capture test is based upon one or more of:

$$T\max - T\min > 30 \text{ ms} \quad (1)$$

$$0.2 < |\text{Max} - a \text{ baseline}(BL)|/|BL - \text{Min}| < 5; \quad (2)$$

$$(\text{Max} - BL|/|\text{Min} - BL| \leq LL \text{ and } BL < |\text{Min}/8|) \quad (3)$$

$$T\min < 60 \text{ ms; and} \quad (4)$$

$$\text{Max} - \text{Min} > 3.5 \text{ mV}. \quad (5)$$

The effective capture test determines whether effective capture of a ventricle is occurring before, while and/or after the medical device has been implanted in a patient. The effective capture test uses ideal pace timing conditions for a few beats during the effective capture test. Ideal pace timing conditions means that the normal pace timing is modified to increase the chances of effective capture. If effective capture is not achieved during ideal pace timing conditions, then effective capture cannot be achieved during normal daily monitoring to pace therapy.

Effective capture is achieved by delivering ultrasound pacing stimuli at sufficient energy and at the proper timing to tissue, which provides beneficial results over known capture management algorithms. While capture management algorithms are able to artificially modify the timing (i.e., overdrive pace or use very short SAV/PAV), the main focus of capture management algorithms is on sufficient energy delivery of a pacing stimulus. Capture management algorithms generally do not address proper timing and cannot be used to assess effective capture during normal device operation.

Referring to FIG. 17B, a 420 KHz transducer with 3 cm diameter was employed. Capture occurred at boxes 1900; capture rarely occurred at boxes 1902; and no capture occurred at boxes 1904 of FIG. 17B. Effective capture generally occurred at 500 kPa or greater when the pulse width was between 0.1 and 50 ms. No capture occurred at or below 300 kPa.

Referring to FIG. 17D, a 220 KHz and 3 cm transducer was employed. Capture occurred at boxes 1900; capture rarely occurred at boxes 1902; and no capture occurred at boxes 1904 of FIG. 17D. Effective capture generally occurred between 0.5 and 10 ms along the X-axis at or above 600 KPa of pressure. No capture occurred at or below 400 KPa.

FIGS. 18A-18C and FIGS. 19A-19C establish that various areas of the heart effectively respond to delivery of the HIFU pace. The data generated in FIG. 18A relied upon a transducer that employed 200 KHz frequency. Ultrasound was delivered at 500 KPa amplitude at 10 ms pulse width to the cardiacapex. The data generated in FIG. 18B relied upon a transducer that employed 220 KHz frequency. The ultrasound was delivered at 700 KPa amplitude at 5 ms pulse width. The data generated in FIG. 18C relied upon a transducer that employed 220 KHz frequency, with 600 KPa amplitude and 1.0 ms pulse width for the area believed to be the basal septum.

Figure 19A:
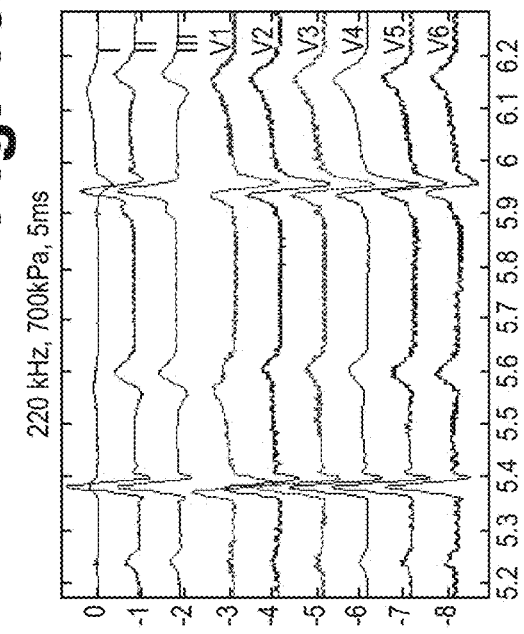
FIG. 19A depicts an intrinsic beat followed by capture occurring at an area believed to be the RVOT in response to an ultrasound pace being delivered.
Figure 19C:
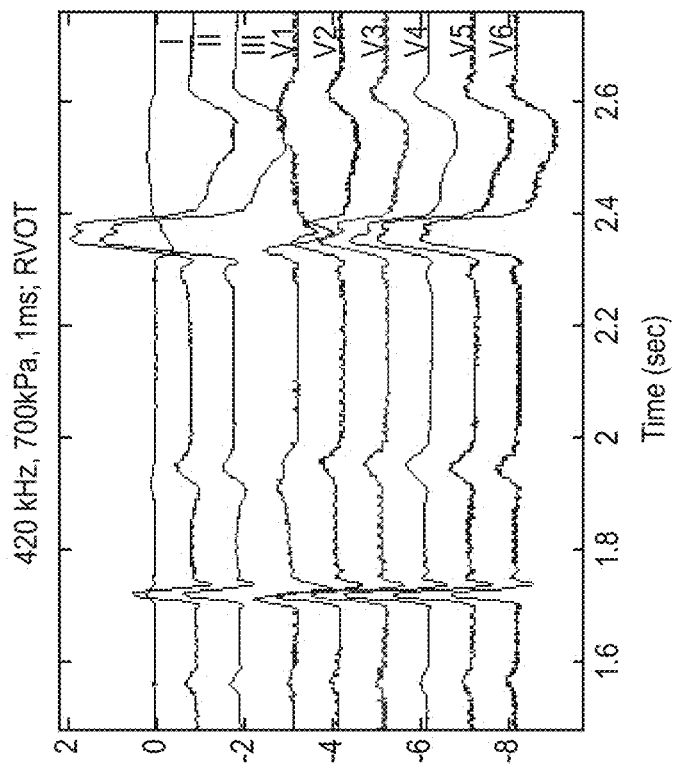
FIG. 19C depicts an intrinsic beat followed by capture occurring at an area believed to be the RVOT in response to an ultrasound pace being delivered.
Figure 19B:
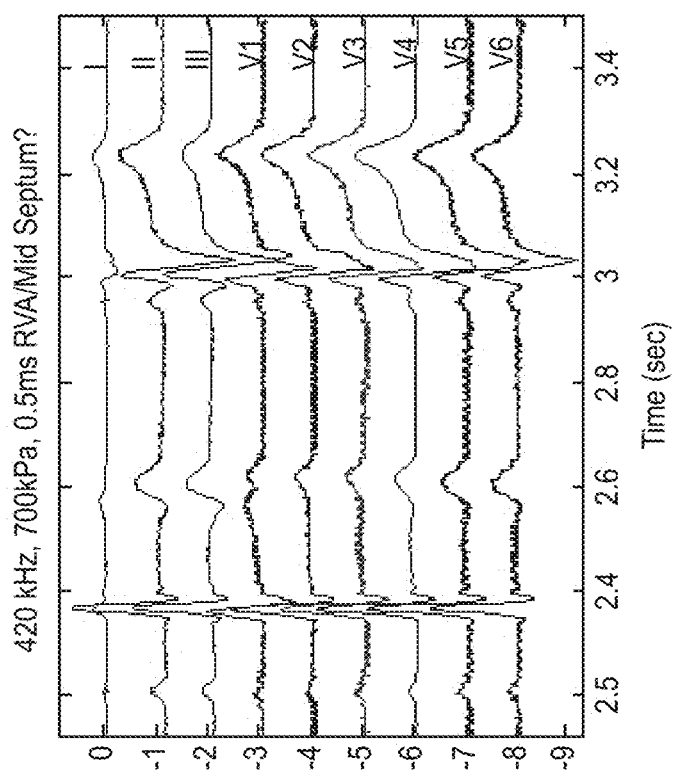
FIG. 19B depicts an intrinsic beat followed by capture occurring at an area believed to be the RVA/mid-septum in response to an ultrasound pace being delivered.
Figure 20:
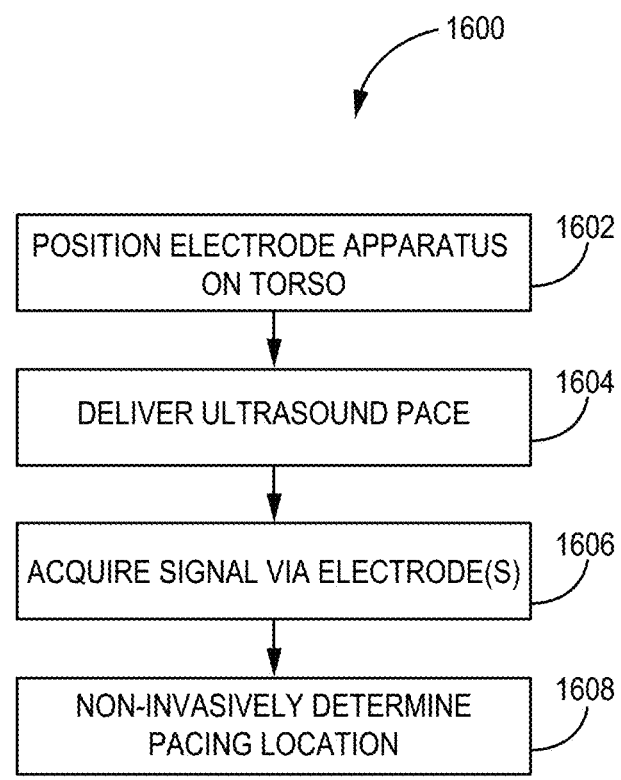
FIG. 20 is a flow diagram of an exemplary algorithm to determine an optimal coronary sinus branch to place a medical electrical lead.

The data generated for the plots of FIGS. 19A-19C all used a transducer having a frequency of 420 KHz. Data presented in FIG. 19A involved ultrasound delivery at 600 KPa amplitude and 0.10 ms pulse width, delivered to the area believed to the right ventricular outflow tract (RVOT). Data presented in FIG. 19B involved ultrasound delivery at 700 KPa amplitude and 0.50 ms pulse width, delivered to the RVA/mid-septum. Data presented in FIG. 19C involved ultrasound delivery at 700 KPa amplitude and 1 ms pulse width, delivered to the area believed to be the RVOT. Method 1600, depicted in FIG. 20, can employ non-invasive and/or invasive techniques for determining the best LV pacing location or best coronary sinus (CS) branch to cannulate when placing a medical electrical lead. Selection of the optimal CS branch can occur prior to and/or during the process of implanting the lead. Generally, method 1600 involves determining the optimal CS branch by sensing the cardiac response to non-invasive pacing pulses delivered by the ultrasound transducer through skin to a target cardiac tissue location. The ultrasound transducer can be configured to deliver ultrasound through the skin of a patient at a pre-specified pressure to capture cardiac tissue. Exemplary pressures that can be employed by the transducer include 300 kPa to 1 MPa. In one or more embodiments, pressures that can be employed by the transducer include 500 to 800 KPa.

Cardiac activity in response to the ultrasound transducer is sensed via the electrode apparatus 110 that is placed around the torso. At block 1604, an ultrasound transducer is placed on the skin and over the cardiac tissue. The transducer then delivers ultrasound paces to the cardiac tissue. At block 1606, signals are acquired by the processor of system 100 from the electrode(s) associated with the electrode apparatus 110.

At block 1608, a non-invasive determination is made as to the best location from which to pace tissue is made. For example, after the signal(s) are acquired from the set of electrodes spatially set apart in electrode apparatus 110. The determination is made through the processor acquiring the data from the sensed signals and using the data in LVAT and/or SDAT equations, as described herein. Thereafter, pacing parameters can be adjusted in response to the acquired signals (e.g. ECG signals and/or signals from implanted electrodes). For example, delivery of pacing pulses can be adjusted in response to detected P-waves as described herein.

Figure 21:
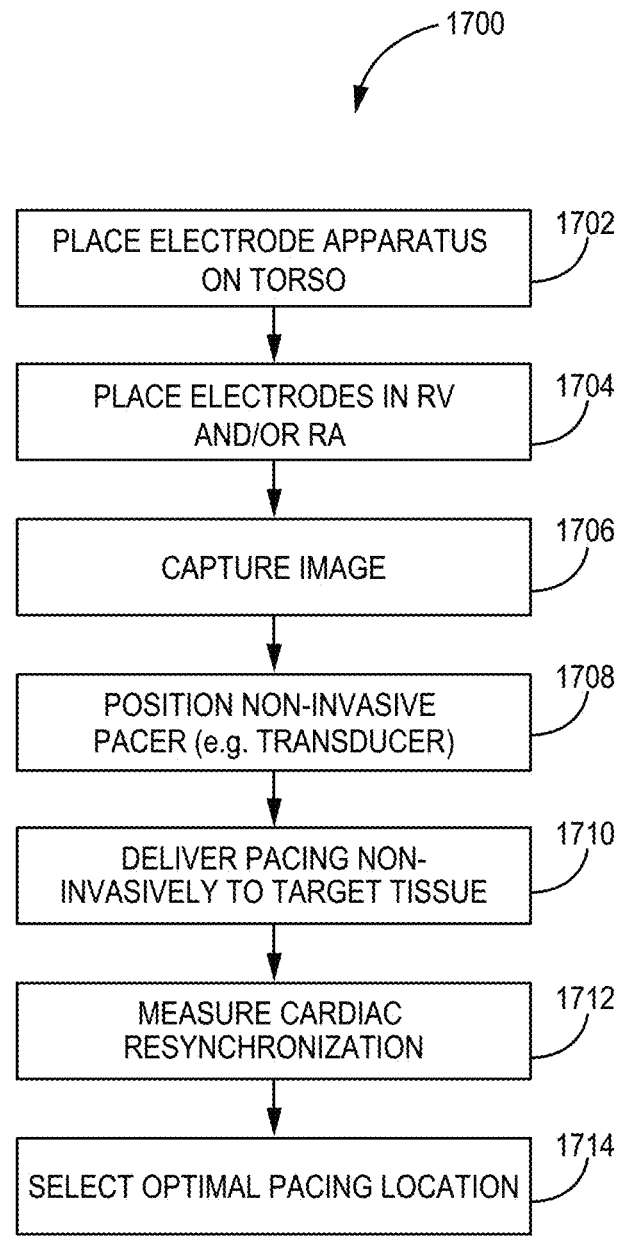
FIG. 21 is a flow diagram of an exemplary timing algorithm of an ultrasonic pace when a patient is not experiencing atrial fibrillation.

Method 1700, depicted in FIG. 21, can be used separately or in conjunction with method 1600. Method 1700 begins at block 1702 in which the electrode apparatus 110 is placed on or around a patient's torso. At block 1704, implanted electrodes (e.g. electrodes on a RV lead, subcutaneous electrodes, electrodes placed substernally etc.) are used for sensing cardiac activity. The electrodes could have been previously implanted or implanted immediately before determining an optimum location to place a pacing electrode(s) in or on the left ventricle.

The isochrone maps acquired during the detection of cardiac response are then matched to maps acquired during actual placement of the lead by the physician. For example, the map, acquired during the noninvasive measurements (i.e. ECG belt only) that provided the most optimal response to the ultrasound pacing pulses from an optimal location is used as a template to match with the maps acquired during real-time placement of the medical electrical lead. Once the previously stored and real-time maps or map data are substantially matched, the optimal position of the pacing electrode(s) are properly positioned. Substantially matched maps (or map data) means that 10% or less difference exists between the stored and real-time acquired activation time maps). The physician then attaches the lead or other pacing device in its location.

Evaluation method 1700 can be performed in a clinical setting (e.g. EP laboratory, health clinic, hospital etc.) using system 100 depicted in FIG. 1. Method 1700 starts at block 1702 when the electrode apparatus 110 is placed on or around all or a portion of the torso of the patient before delivering pacing pulses to tissue. In particular, the electrodes 112 of electrode apparatus 110 may be positioned around the circumference of a patient 14, including the posterior, lateral, posterior lateral, and anterior locations of the torso of patient 14.

At block 1704, the RV and/or RA lead are positioned in or on the right ventricle 28 and/or right atrium 26, respectively, using conventional techniques. The RV lead 18 extends through one or more veins (not shown), the superior vena cava (not shown), and the right atrium 26, and into the right ventricle 28. The RA lead 22 extends through one or more veins and the vena cava, and into the right atrium 26 of the heart 12. At block 1706, a CS venogram is captured using conventional techniques. Target branches (i.e. lateral vein) are identified via the CS venogram. Based upon the CS venogram, the physician may wish to evaluate two or three target CS branch locations (e.g. lateral branches) for the best lateral branch to cannulate for pacing tissue. The CS branches can be close e.g. 2 centimeters or further apart. At block 1708, the ultrasound transducer is placed on the skin near the target location (i.e. a target branch that is selected from a set of branches) and used by the physician to non-invasively pace the cardiac tissue (e.g. LV). At block 1710, after pacing pulses are delivered to pace the LV from a target branch, the change in cardiac resynchronization is measured at block 1712, as described herein. Exemplary methods for measuring the change in cardiac resynchronization include standard deviation of the activation-times (SDAT) and/or left ventricle activation times (LVAT) from the electrode apparatus 110 and/or implantable electrodes. Each target site of the set of target sites are evaluated for locating electrode(s) (e.g. lead, subcutaneous electrodes etc.). In one or more embodiments, the best location (e.g. location that provides the best or most optimal resynchronization (i.e. largest resynchronization for SDAT and/or LVAT) is selected amongst the set of target sites at block 1714. In one or more other embodiments, a large change (i.e. 10% or more change in SDAT and/or LVAT etc. or 15% or more change of other criteria for cardiac resynchronization (CRT)), then, according to one or more embodiments, the evaluation of target sites ends with a large change (e.g. 10% or greater of SDAT and/or LVAT or other CRT criteria) being achieved. SDAT of some or all of electrodes 112 on the surface of the torso of patient 14 may be calculated using the estimated cardiac activation times over the surface of a model heart. Alternatively or additionally, LVATs can also be acquired from electrodes (e.g. electrodes from apparatus 110 and/or implanted electrodes). The electrodes can be located on a medical electrical lead. The electrodes can also be subcutaneous.

SDAT employs the following exemplary equations:
a) Calculate mean of valid channels:

$$\text{mean}_{AT} = \frac{\sum_{n=\text{valid channels}} \text{Activation\_time}_i}{\text{Number\_of\_valid\_channels}}$$

"n" refers to a particular electrode of a set of electrodes (e.g. first electrode out of four electrodes on a left ventricular lead etc.)
  i) N is the total number of surface electrodes on the belt that provide a valid ECG signal. The electrode apparatus 110 (e.g. ECG belt may have some reference limb leads that are not part of SDAT calculation. Additionally, if any electrodes are not in contact with the surface, the electrode data is considered 'invalid' because valid ECG signals are not produced.
b) Calculate the squared_STD (for i=1 to Number_of_valid_channels)

$$\text{squared}_{STD} = \frac{1}{N} * (\text{Activation}_{time_i} - \text{mean}_{AT})^2$$

STD refers to standard deviation.
c) Calculate standard deviation (SDAT)

$$\text{SDAT} = \sqrt{\text{squared}_{STD}}$$

The equation for LVAT is directed to the mean of the LV activation times. For example, the LVAT equation is as follows:

$$LVAT = \frac{\sum_{n=LV \text{ valid channels}} \text{Activation\_time}_i}{\text{Number\_of\_LV\_valid\_channels}}$$

One of the indices of electrical dyssynchrony may be a standard deviation index computed as the standard deviation of the activations-times (SDAT) of some or all of electrodes 112 on the surface of the torso of patient 14. In some examples, the SDAT may be calculated using the estimated cardiac activation times over the surface of a model heart. Exemplary methods for measuring change in resynchronization may be seen with respect to U.S. Pat. No. 8,972,228 issued May 3, 2015, and assigned to the assignee of the present invention, the disclosure of which is incorporated by reference in its entirety herein.

After non-invasively determining the optimal CS branch to cannulate, the physician then starts to insert the medical electrical lead through the CS branch. The isochrone maps of torso-surface activation times that were periodically saved into memory of the imaging 120 and/or computing apparatus 140 during pacing a target location serve as a reference point for the physician. The images (i.e. isochrone maps and/or two dimensional ultrasound images) are not only helpful for visualizing the CS vein branches, the images are also helpful guidance since the physician can match the activation times of the previously saved images to the activation times of the maps acquired while moving the medical electrical lead through the target CS branch. Matching the isochrone maps or images acquired during placement of the lead to the previously stored maps that were stored during noninvasively pacing tissue shows how the electrode position, on the lead or other medical device, is titrated to the proper location within the CS branch. For example, a target location is paced by aiming the ultrasound pulse transducer at the target tissue. When excitation of the target tissue occurs, the lead is placed by using the isochrone maps as a reference to continuously measure and adjust the position of the lead until the map data stored in memory and the map data acquired while placing the lead substantially match. The one or more electrodes (e.g. located on a lead, subcutaneously placed, etc.) are positioned to match the response (i.e. isochrone map) that provide the optimal resynchronization.

One or more other embodiments involve the option of pacing the RV simultaneously or sequentially (i.e. RV pacing from the RV lead, LV pacing from ultrasound transducer) with a nominal AV timing or AV timing=70% of patients intrinsic PR interval where atrial sensing is performed from the RA lead). Different VV delays are then tested for each CS branch location. Preferably, different VV delays are tested for each CS branch location if LV only pacing (referred to as fusion pacing) or biventricular pacing (i.e. simultaneous pacing of the does not produce adequate (at least 10%) change in SDAT and/or LVAT.

Cannulate the branch with the best resynchronization (i.e. largest improvement in SDAT/LVAT). Exemplary optimization of cardiac resynchronization exhibited in the largest improvements SDAT and/or LVAT are selected for placement of the lead Specifically, the pacing vector (i.e. on the lead, subcutaneous electrode(s) etc.) are placed in response to determining the location of the pacing vector that provides the best cardiac resynchronization results.

Method 1700, depicted in FIG. 21, can be performed in a clinical setting (e.g. EP laboratory, health clinic, hospital etc.) using system 100 depicted in FIG. 1. Method 1700 starts at block 1702 when the electrode apparatus 110 is placed on or around all or a portion of the torso of the patient before delivering pacing pulses to tissue. In particular, the electrodes 112 of electrode apparatus 110 may be positioned around the circumference of a patient 14, including the posterior, lateral, posterior lateral, and anterior locations of the torso of patient 14.

At block 1702, signals are acquired from the electrode apparatus 110 (i.e. same signal acquired from the surface ECG e.g. ECG belt for processing) thereby allowing the processor to obtain periodic automatic detection of the intrinsic PR interval. At block 1704, automatic sensing occurs of the p-wave from the ECG signal. The ECG signal can be acquired from a Lewis lead which is known for acquiring larger P-waves. The timing of the ultrasound pacing can be adjusted in response sensing of the P-wave at block 1704. For example, the timing of the ultrasound pacing could be adjusted in the following manner. First, detect a p-wave, then time the ultrasound pace to be PR minus a pre-specified time period (e.g. PR-50 ms, PR-40 ms, PR-30 ms, PR-20 ms etc.) following the P-wave, on successive beats. By timing the ultrasound pacing according to different PR minus a pre-specified time period, the timing of the ultrasound pacing can be evaluated through various degrees of fusion with intrinsic activation. In one or more embodiments, the ultrasonic delivery of pacing pulses can be combined with a 2-D ultrasound imaging phased array. An image can then be collected. The ultrasound transducer could be pointed in the direction for pacing delivery, and then fire pacing in the desired direction. The image guidance would help to pace in good locations.

Through this disclosure, a determination can be effectively and noninvasively made as to whether a patient can benefit from CRT therapy that may reduce overall health care costs. Methods 1600 and/or 1700 can be used in a variety of ways. Not only can method 1600 or 1700 be used for lead placement, method 1600 can also be employed for lead revision to find the best location from which to pace. The present disclosure provides useful features for physicians. For example, periodic automatic detection of the intrinsic PR interval from surface ECG (i.e. same signal that is sent to the ECG belt for processing) can be performed. The present disclosure also provides for automatic sensing of the p-wave from the ECG signal (i.e. same signal that is sent to the ECG belt for processing. Timing of the ultrasound pacing can be configured responsive to detection of the P-wave. For example, after a P-wave is detected, the ultrasound pace is timed to be delivered at one of PR-50 ms, PR-40 ms, PR-30 ms, PR-20 ms following the P-wave, on successive beats. This is a way of scanning the timing of the ultrasound pacing through various degrees of fusion with intrinsic activation.

In one or more embodiments, ultrasonic delivery of pacing pulses can be combined with a 2-D ultrasound imaging phased array. An image can be collected. The ultrasound transducer is pointed in the direction for pacing delivery. The ultrasound transducer fires the pacing pulses in the desired direction. The image guidance data is recorded thereby helping to pace in optimal locations.

While specific examples have been described in the specification and illustrated in the drawings, it will be understood by those of ordinary skill in the art that various changes may be made and equivalents may be substituted for elements thereof without departing from the scope of the present disclosure as defined in the claims. Furthermore, the mixing and matching of features, elements and/or functions between various examples is expressly contemplated herein so that one of ordinary skill in the art would appreciate from this disclosure that features, elements and/or functions of one example may be incorporated into another example as appropriate, unless described otherwise, above. Moreover, many modifications may be made to adapt a particular situation or material to the teachings of the present disclosure without departing from the essential scope thereof. For example, while ultrasound, via the ultrasound transducer can be employed to guide the ultrasound pulses, a phased array can be used to focus on different target locations in close proximity. A phased array can be used to model different target locations in close proximity. In particular, the phased array can be used to fine tune the best CS branch location to deliver a left ventricular lead.

In one or more other embodiments, the ECG belt, maybe combined with limb leads to identify the approximate location of the pacing. In this manner, the ECG belt could indicate the pacing location that produced the best LVAT or SDAT. This would allow the ultrasound pacing to be delivered randomly in a shotgun-like approach, and the ECG belt would indicate which beat produced the best synchronization and where the pacing occurred.

Exemplary Embodiments

The following paragraphs enumerated consecutively from 1 through 38 provide for various aspects of the present invention. In one embodiment, in a first paragraph (1), the present invention provides:

Embodiment 1 is a method of comprising:

delivering noninvasively ultrasonic energy to cardiac tissue;

in response to delivering ultrasonic energy to the cardiac tissue, receiving, with a processing unit, a torso-surface potential signal from each of a plurality of electrodes distributed on a torso of a patient;

for at least a subset of the plurality of electrodes, calculating, with the processing unit, a torso-surface activation time based on the signal sensed from the electrode; and presenting, by the processing unit, to a user, an indication of a degree of dyssynchrony of the torso-surface activation times via a display.

Embodiment 2 is a method of embodiment 1 wherein the ultrasonic energy is high intensity focused ultrasound (HIFU).

Embodiment 3 is a method of embodiment 11 wherein receiving the torso-surface potential signals and calculating the torso-surface activation times comprises receiving first torso-surface potential signals and calculating first torso-surface activation times a first time during intrinsic conduction of a heart of the patient and receiving second torso-surface potential signals and calculating second torso-surface activation times a second time during CRT pacing of the heart, and wherein presenting the indication of the degree of dyssynchrony comprises presenting an indication of a change in dyssynchrony from the intrinsic conduction to the CRT pacing of the heart.

Embodiment 4 is a method of any of embodiments 1-3, wherein the ultrasonic energy being delivered at up to 3 megaPascal (MPa) sound pressure level (SPL) for pacing of cardiac tissue.

Embodiment 5 is a method of any of embodiments 1-4, wherein the ultrasonic energy being delivered to at least one localized area on a left ventricular wall.

Embodiment 6 is a method of any of embodiments 1-5 wherein the ultrasonic energy being delivered for noninvasive cardiac resynchronization therapy involving ultrasonic stimulation of at least one right ventricular site and at least one left ventricular site with the delivery of stimulation timed relative to P-wave on the surface ECG.

Embodiment 7 is a method of any of embodiments 1-6, wherein the ultrasonic energy being used to evaluate electrical stimulation to affect cardiac resynchronization therapy.

Embodiment 8 is a method of any of embodiments 1-6, wherein the ultrasound pace is delivered at a variety of timings with respect to anticipated intrinsic ventricular depolarization.

Embodiment 9 is a method of any of embodiments 1-6, wherein the delivery of the ultrasonic pace may be timed at a certain time interval after an onset of the surface ECG P-wave such that the time-interval may be 80 ms shorter than the intrinsic P-R interval, 60 ms shorter than the intrinsic P-R interval, 50 ms shorter than the intrinsic P-R interval, 40 ms shorter than the intrinsic P-R interval, 30 ms shorter than the intrinsic P-R interval, 20 ms shorter than the intrinsic P-R interval, 10 ms shorter than the intrinsic P-R interval.

Embodiment 10 is a system comprising:
means for noninvasively delivering ultrasonic energy to cardiac tissue;
in response to delivering ultrasonic energy to the cardiac tissue, means for receiving, with a processing unit, a torso-surface potential signal from each of a plurality of electrodes distributed on a torso of a patient;
for at least a subset of the plurality of electrodes, processing means for calculating, with the processing unit, a torso-surface activation time based on the signal sensed from the electrode; and
means for presenting, by the processing unit, to a user, an indication of a degree of dyssynchrony of the torso-surface activation times via a display.

Embodiment 11 is system according to embodiment 10 wherein the ultrasonic energy is high intensity focused ultrasound (HIFU).

Embodiment 12 is a system of embodiments 10-11 wherein HIFU is delivered by a transducer.

Embodiment 13 is a system of embodiments 10-13,
wherein receiving the torso-surface potential signals and calculating the torso-surface activation times comprises receiving first torso-surface potential signals and calculating first torso-surface activation times a first time during intrinsic conduction of a heart of the patient and receiving second torso-surface potential signals and calculating second torso-surface activation times a second time during CRT pacing of the heart, and wherein presenting the indication of the degree of dyssynchrony comprises presenting an indication of a change in dyssynchrony from the intrinsic conduction to the CRT pacing of the heart.

Embodiment 14 is a system of embodiments 10-12, wherein the ultrasonic energy being delivered at up to 3 megaPascal (MPa) sound pressure level (SPL) for pacing of cardiac tissue.

Embodiment 15 is a system of embodiments 10-1, wherein the ultrasonic energy being delivered to at least one localized area on a left ventricular wall.

Embodiment 16 is a system of embodiments 10-16 wherein the ultrasonic energy being delivered for noninvasive cardiac resynchronization therapy involving ultrasonic stimulation of at least one right ventricular site and at least one left ventricular site with the delivery of stimulation timed relative to P-wave on the surface ECG.

Embodiment 17 is a system of embodiment of embodiment 16, wherein the ultrasonic energy being used to evaluate electrical stimulation to affect cardiac resynchronization therapy.

Embodiment 18 is a system of embodiment 16 wherein the ultrasound pace is delivered at a variety of timings with respect anticipated intrinsic ventricular depolarization.

Embodiment 19 wherein the delivery of the ultrasonic pace may be timed at a certain time interval after an onset of the surface ECG P-wave such that the time-interval may be 80 ms shorter than the intrinsic P-R interval, 60 ms shorter than the intrinsic P-R interval, 50 ms shorter than the intrinsic P-R interval, 40 ms shorter than the intrinsic P-R interval, 30 ms shorter than the intrinsic P-R interval, 20 ms shorter than the intrinsic P-R interval, 10 ms shorter than the intrinsic P-R interval.

Embodiment 20 is a method comprising:
delivering noninvasively ultrasonic energy to cardiac tissue;
in response to delivering ultrasonic energy to the cardiac tissue, receiving, with a processing unit, a torso-surface potential signal from each of a plurality of electrodes distributed on a torso of a patient;
for at least a subset of the plurality of electrodes, calculating, with the processing unit, a torso-surface activation time based on the signal sensed from the electrode; and
presenting, by the processing unit, to a user, an indication of a degree of dyssynchrony of the torso-surface activation times via a display, wherein the ultrasonic energy is high intensity focused ultrasound (HIFU),
wherein receiving the torso-surface potential signals and calculating the torso-surface activation times comprises receiving first torso-surface potential signals and calculating first torso-surface activation times a first time during intrinsic conduction of a heart of the patient and receiving second torso-surface potential signals and calculating second torso-surface activation times a second time during CRT pacing of the heart, and wherein presenting the indication of the degree of dyssynchrony comprises presenting an indication of a change in dyssynchrony from the intrinsic conduction to the CRT pacing of the heart.

Embodiment 21 is a method comprising:
delivering ultrasonic energy to cardiac tissue;
in response to delivering ultrasonic energy to the cardiac tissue, receiving, with a processing unit, a torso-surface potential signal from each of a plurality of electrodes distributed on a torso of a patient;

for at least a subset of the plurality of electrodes, calculating, with the processing unit, a torso-surface activation time based on the signal sensed from the electrode; and presenting, by the processing unit, to a user, an indication of a degree of dyssynchrony of the torso-surface activation times via a display, wherein receiving the torso-surface potential signals and calculating the torso-surface activation times comprises receiving first torso-surface potential signals and calculating first torso-surface activation times a first time during intrinsic conduction of a heart of the patient and receiving second torso-surface potential signals and calculating second torso-surface activation times a second time during CRT pacing of the heart, and wherein presenting the indication of the degree of dyssynchrony comprises presenting an indication of a change in dyssynchrony from the intrinsic conduction to the CRT pacing of the heart.

Embodiment 23 is a method of embodiment 22 further comprising:

(k) introducing the medical electrical lead to a coronary sinus; and (l) moving the medical electrical lead to the coronary sinus branch that facilitates optimal cardiac resynchronization.

Embodiment 24 is a method of one of embodiments 22-23 wherein the first tissue site and the another tissue site are a first coronary sinus branch and a second coronary sinus branch.

Embodiment 25 is a method of one of embodiments 22-24 further comprising:

capturing one or more images of a set of coronary sinus branches in a venogram; and presenting, by the processing unit, to a user, the set of coronary sinus branches via a display.

Embodiment 26 is a method comprising:

delivering noninvasively ultrasound pacing to cardiac tissue;

in response to delivering ultrasonic energy to the cardiac tissue, receiving, with a processing unit, a torso-surface potential signal from each of a plurality of electrodes distributed on a torso of a patient;

acquiring P-wave signals in response to delivering ultrasonic energy to the cardiac tissue;

timing the ultrasound pacing to PR minus a pre-specified time period following the P-wave, on successive beats; and presenting, by the processing unit, to a user, an indication of a degree of dyssynchrony of the torso-surface activation times via a display.

Embodiment 27 is a method of embodiment 25-26 wherein the PR minus a pre-specified time period being one of PR-50 ms, PR-40 ms, PR-30 ms, and PR-20 ms.

Embodiment 28 is a method of embodiment 25 or 26 further comprising:

employing different PR minus a pre-specified time period in order to evaluate various degrees of fusion with intrinsic activation.

Embodiment 29 is a method of the preceding embodiments further comprising:

delivering pacing pulses through a pacing electrode on the RV lead at a pre-specified interval to determine one of timing cardiac resynchronization therapy and VV delay.

Embodiment 31 is a method of embodiment 29 wherein the pre-specified interval is used to determine timing delays for sequential biventricular pacing.

Embodiment 32 is a method of embodiment 30 wherein pre-specified interval is one of 10 ms, 20 ms, 30 ms, 40 ms, 50 ms, 60 ms, 70 ms and 80 ms.

Embodiment 33 is a method comprising:

(a) applying an electrode apparatus having a plurality of electrodes to a torso of a patient;

(b) introducing one of a right ventricular (RV) lead to a right ventricle or a right atrial (RA) lead to a right atrium;

(c) delivering noninvasively ultrasonic energy to a target tissue selected from a set of target tissues;

(d) in response to delivering ultrasonic energy to the cardiac tissue, receiving, with a processing unit, a torso-surface potential signal from each of a plurality of electrodes distributed on a torso of a patient for the target tissue;

(e) sensing signals from one of the RA lead and the RV lead in response to delivering ultrasonic energy;

(f) for at least a subset of the plurality of electrodes, calculating, with the processing unit, a torso-surface activation time based on the signal sensed from the electrode;

(g) repeating steps (c) through (f) for another tissue site to obtain cardiac resynchronization data;

(i) determining whether the tissue site or the another tissue site provides optimal cardiac resynchronization;

(j) in response step (i), selecting one of the tissue site and the another tissue site that provides optimal cardiac resynchronization for locating a medical electrical lead;

(k) introducing the medical electrical lead to a target area in a ventricle, wherein the target area is one of the endocardium and epicardium; and (l) moving the medical electrical lead to the target area in the ventricle that facilitates optimal cardiac resynchronization.

It is intended that the present disclosure not be limited to the particular examples illustrated by the drawings and described in the specification as the best mode presently contemplated for carrying out this disclosure, but that the scope of the present disclosure will include any embodiments falling within the foregoing description and the appended claims.

What is claimed is:

1. A method comprising:
   (a) applying an electrode apparatus having a plurality of electrodes to a torso of a patient;
   (b) introducing one of a right ventricular (RV) lead to a right ventricle or a right atrial (RA) lead to a right atrium;
   (c) delivering noninvasively ultrasonic energy to a target tissue selected from a set of target tissues;
   (d) in response to delivering ultrasonic energy to the cardiac tissue, receiving, with a processing unit, a torso-surface potential signal from each of a plurality of electrodes distributed on a torso of a patient for the target tissue;
   (e) sensing signals from one of the RA lead and the RV lead in response to delivering ultrasonic energy;
   (f) for at least a subset of the plurality of electrodes, calculating, with the processing unit, a torso-surface activation time based on the signal sensed from the electrode;
   (g) repeating steps (c) through (f) for another tissue site to obtain cardiac resynchronization data;
   (i) determining whether the tissue site or the another tissue site provides optimal cardiac resynchronization; and
   (j) in response step (i), selecting one of the tissue site and the another tissue site that provides optimal cardiac resynchronization for locating a medical electrical lead.

2. A method of claim 1 further comprising:
(k) introducing the medical electrical lead to a coronary sinus; and
(l) moving the medical electrical lead to the coronary sinus branch that facilitates optimal cardiac resynchronization.

3. A method of claim 1 wherein the first tissue site and the another tissue site are a first coronary sinus branch and a second coronary sinus branch.

4. A method of claim 1 further comprising:
capturing one or more images of a set of coronary sinus branches in a venogram; and
presenting, by the processing unit, to a user, the set of coronary sinus branches via a display.

5. The method of claim 4, further comprising:
acquiring P-wave signals in response to delivering ultrasonic energy to the cardiac tissue; and
timing the ultrasonic energy to PR minus a pre-specified time period following the P-wave, on successive beats.

6. A method of claim 5 wherein the PR minus a pre-specified time period being one of PR-50 ms, PR-40 ms, PR-30 ms, and PR-20 ms.

7. A method of claim 5 further comprising:
employing different PR minus a pre-specified time period in order to evaluate various degrees of fusion with intrinsic activation.

8. A method comprising:
(a) applying an electrode apparatus having a plurality of electrodes to a torso of a patient;
(b) introducing one of a right ventricular (RV) lead to a right ventricle or a right atrial (RA) lead to a right atrium;
(c) delivering noninvasively ultrasonic energy to a target tissue selected from a set of target tissues;
(d) in response to delivering ultrasonic energy to the cardiac tissue, receiving, with a processing unit, a torso-surface potential signal from each of a plurality of electrodes distributed on a torso of a patient for the target tissue;
(e) sensing signals from one of the RA lead and the RV lead in response to delivering ultrasonic energy;
(f) for at least a subset of the plurality of electrodes, calculating, with the processing unit, a torso-surface activation time based on the signal sensed from the electrode;
(g) repeating steps (c) through (f) for another tissue site to obtain cardiac resynchronization data;
(i) determining whether the tissue site or the another tissue site provides optimal cardiac resynchronization; and
(j) in response step (i), selecting one of the tissue site and the another tissue site that provides optimal cardiac resynchronization for locating a medical electrical lead.

9. The method of claim 8 further comprising:
delivering pacing pulses through a pacing electrode on the RV lead at a pre-specified interval following a P-wave to determine one of timing cardiac resynchronization therapy and VV delay.

10. The method of claim 9 wherein the pre-specified interval is used to determine timing delays for sequential biventricular pacing.

11. The method of claim 9 wherein pre-specified interval is one of 10 ms, 20 ms, 30 ms, 40 ms, 50 ms, 60 ms, 70 ms and 80 ms.

12. A method comprising:
(a) applying an electrode apparatus having a plurality of electrodes to a torso of a patient;
(b) introducing one of a right ventricular (RV) lead to a right ventricle or a right atrial (RA) lead to a right atrium;
(c) delivering noninvasively ultrasonic energy to a target tissue selected from a set of target tissues;
(d) in response to delivering ultrasonic energy to the cardiac tissue, receiving, with a processing unit, a torso-surface potential signal from each of a plurality of electrodes distributed on a torso of a patient for the target tissue;
(e) sensing signals from one of the RA lead and the RV lead in response to delivering ultrasonic energy;
(f) for at least a subset of the plurality of electrodes, calculating, with the processing unit, a torso-surface activation time based on the signal sensed from the electrode;
(g) repeating steps (c) through (f) for another tissue site to obtain cardiac resynchronization data;
(i) determining whether the tissue site or the another tissue site provides optimal cardiac resynchronization;
(j) in response step (i), selecting one of the tissue site and the another tissue site that provides optimal cardiac resynchronization for locating a medical electrical lead;
(k) introducing the medical electrical lead to a target area in a ventricle, wherein the target area is one of the endocardium and epicardium; and
(l) moving the medical electrical lead to the target area in the ventricle that facilitates optimal cardiac resynchronization.

* * * * *